(12) United States Patent
Jaroskova et al.

(10) Patent No.: US 9,776,965 B2
(45) Date of Patent: Oct. 3, 2017

(54) PYRROLIDIN-2-ONE AND PIPERIDIN-2-ONE DERIVATIVES AS 11-BETA HYDROXYSTEROID DEHYDROGENASE INHIBITORS

(71) Applicant: Janssen Pharmaceutica N.V., Beerse (BE)

(72) Inventors: Libuse Jaroskova, Vosselaar (BE); Joannes Theodorus Maria Linders, Eindhoven (NL); Christophe Francis Robert Nestor Buyck, Hamme (BE); Louis Jozef Elisabeth Van Der Veken, Vosselaar (BE); Vladimir Dimtchev Dimitrov, Sofia (BG); Theo Teofanov Nikiforov, San Jose, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 15/051,717

(22) Filed: Feb. 24, 2016

(65) Prior Publication Data
US 2016/0168094 A1   Jun. 16, 2016

Related U.S. Application Data

(62) Division of application No. 14/656,752, filed on Mar. 13, 2015, now Pat. No. 9,302,987, which is a division
(Continued)

(30) Foreign Application Priority Data

May 7, 2004   (EP) ..................................... 04101991

(51) Int. Cl.
C07D 211/76   (2006.01)
C07D 207/26   (2006.01)
(Continued)

(52) U.S. Cl.
CPC .......... *C07D 211/76* (2013.01); *C07D 207/26* (2013.01); *C07D 207/267* (2013.01); *C07D 405/06* (2013.01)

(58) Field of Classification Search
CPC  C07D 207/26; C07D 207/267; C07D 211/76; C07D 405/06
(Continued)

(56) References Cited

U.S. PATENT DOCUMENTS 2,510,945  A   6/1950   Badgett et al.
2,524,643  A   10/1950  Walter et al.
(Continued)

FOREIGN PATENT DOCUMENTS

CA   2017287 A1   11/1990
DE   1959898 A1   6/1970
(Continued)

OTHER PUBLICATIONS

Tsukada et al. "Inhibitory acti . . . " J. Pestiside Sci. 26, p. 143-148 (2001).*
(Continued)

*Primary Examiner* — Celia Chang
(74) *Attorney, Agent, or Firm* — Porzio, Bromberg & Newman P.C.

(57) ABSTRACT

The N-oxide forms, the pharmaceutically acceptable addition salts and the stereochemically isomeric forms thereof, wherein
  n is 1 or 2;
  L represents a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl, hydroxy, $C_{1-3}$alkyloxy- or phenyl-$C_{1-4}$alkyl;
  M represents a direct bond or a $C_{1-3}$alkyl linker optionally substituted with one or two substituents selected from hydroxy, $C_{1-4}$alkyl or $C_{1-4}$alkyloxy;
  $R^1$ and $R^2$ each independently represent hydrogen, halo, cyano, hydroxy,
  $C_{1-4}$alkyl optionally substituted with halo,
  $C_{1-4}$alkyloxy- optionally substituted with one or where possible two or three substituents selected from hydroxy, $Ar^1$ and halo;
  or $R^1$ and $R^2$ taken together with the phenyl ring to which they are attached form naphtyl or 1,3-benzodioxolyl, wherein said naphtyl or 1,3-benzodioxolyl are optionally substituted with halo;
  $R^3$ represents hydrogen, halo, $C_{1-4}$alkyl, $C_{1-4}$alkyloxy-, cyano or hydroxy;
  $R^4$ represents hydrogen, halo, $C_{1-4}$alkyl, $C_{1-4}$alkyloxy-, cyano or hydroxy;
  $R^5$ represents hydrogen, $C_{1-4}$alkyl or $Ar^2$—$C_{1-4}$alkyl-;
  $R^6$ represents hydrogen, halo, $C_{1-4}$alkyl or $C_{1-4}$alkyoxy-;
  $Ar^1$ and $Ar^2$ each independently represent phenyl or naphtyl wherein said phenyl and naphtyl are optionally substituted with $C_{1-4}$alkyl, $C_{1-4}$alkyloxy-, or phenyl-$C_{1-4}$alkyl;
for use as a medicine.

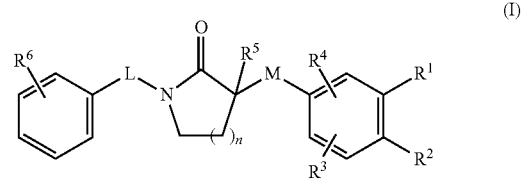

(I)

6 Claims, No Drawings

Related U.S. Application Data of application No. 11/632,675, filed as application No. PCT/EP2005/051968 on Apr. 29, 2005, now Pat. No. 9,012,494.

(51) Int. Cl.
  *C07D 207/267* (2006.01)
  *C07D 405/06* (2006.01)

(58) Field of Classification Search
  USPC ......... 514/327, 422, 424; 546/216; 548/526, 548/543
  See application file for complete search history.

(56) References Cited

U.S. PATENT DOCUMENTS

| | | |
|---|---|---|
| 3,201,466 A | 8/1965 | Dubrovin |
| 3,211,544 A | 10/1965 | Dubrovin |
| 3,277,171 A | 10/1966 | Hopkins |
| 3,328,156 A | 6/1967 | Hopkins |
| 3,526,656 A | 9/1970 | Butler |
| 3,622,567 A | 11/1971 | Razdan |
| 3,919,313 A | 11/1975 | Villani |
| 5,356,907 A | 10/1994 | Clemence et al. |
| 5,395,843 A | 3/1995 | Clemence et al. |
| 5,541,343 A | 7/1996 | Himmelsbach et al. |
| 5,559,130 A | 9/1996 | Clemence et al. |
| 5,776,959 A | 7/1998 | Covey et al. |
| 6,194,406 B1 | 2/2001 | Kane et al. |
| 6,211,199 B1 | 4/2001 | Kane et al. |
| 6,555,572 B2 | 4/2003 | Lauener et al. |
| 7,332,524 B2 | 2/2008 | Linders et al. |
| 7,687,644 B2 | 3/2010 | Jaroskova et al. |
| 7,968,601 B2 | 6/2011 | Linders et al. |
| 2001/0034343 A1 | 10/2001 | Maynard et al. |
| 2003/0087952 A1 | 5/2003 | Wood et al. |
| 2005/0245534 A1 | 11/2005 | Link et al. |
| 2008/0064693 A1 | 3/2008 | Jaroskova et al. |
| 2008/0214597 A1 | 9/2008 | Jaroskova et al. |

FOREIGN PATENT DOCUMENTS

| | | |
|---|---|---|
| DE | 2624290 A | 4/1997 |
| EP | 117462 A2 | 9/1984 |
| EP | 0 399 814 A2 | 11/1990 |
| EP | 437120 B2 | 8/1995 |
| EP | 0481522 B1 | 12/1997 |
| EP | 1127883 A | 8/2001 |
| EP | 873336 B1 | 3/2003 |
| FR | 1399615 | 4/1965 |
| FR | 2714495 A | 6/1995 |
| GB | 1065533 | 4/1967 |
| GB | 2136801 A | 12/1984 |
| JP | 59 164779 | 9/1984 |
| JP | 59 175472 A | 10/1984 |
| JP | 03 086853 | 4/1991 |
| JP | 9 501650 | 2/1997 |
| JP | 11-506471 | 6/1999 |
| WO | WO 95/00493 A1 | 1/1995 |
| WO | WO 96/04254 A | 2/1996 |
| WO | WO 97/19074 A1 | 5/1997 |
| WO | WO 97/22604 A1 | 6/1997 |
| WO | WO 98/11073 A1 | 3/1998 |
| WO | WO 99/26927 A2 | 6/1999 |
| WO | WO 01/23399 | 4/2001 |
| WO | WO 01/90090 A1 | 11/2001 |
| WO | WO 03/065983 A2 | 8/2003 |
| WO | WO 03/104207 A2 | 12/2003 |
| WO | WO 2004/056744 A | 7/2004 |
| WO | WO 2004/056745 A2 | 7/2004 |
| WO | WO 2004/065351 A | 8/2004 |
| WO | WO 2004/075847 A | 9/2004 |
| WO | WO 2004/089415 A2 | 10/2004 |
| WO | WO 2004/089416 A2 | 10/2004 |
| WO | WO 2004/089470 | 10/2004 |

OTHER PUBLICATIONS

"Incyte's Selective Oral Inhibitor of 11beta-HSD1 Demonstrates Improvements in Insuling Sensivity and Lowers Cholesterol levels in Type 2 Diabetics.", About Incyte: Press Release, Incyte Corporation website, http://investor.incyte.com, Jun. 9, 2008.

Aicher et al., "Kappa Opioid Receptor (KOR) and GAD67 Immunoreactivity Are Found in Off and Neutral Cells in the Rostral Ventromedial Medulla.", J. Neurophysiol, 2006, pp. 3465-3473, vol. 96.

Amgen-Investors-Pipeline; http://www.amgen.com/investors/pipe_AMG221.html (1 page), 2008.

Apria-Resources-news; http://www.apria.com/resources/1,2725,494-769212,00.html (4 pages), 2008.

Arzel et al., "An easy acess to (S)-pyrrolidinones and -pyrrolidines from chiral benzylic malonates.", Tetrahedron *Asymmetry*, 1999, pp. 3877-3881, vol. 10(20), XP001203518.

Avdyunina et al., "N-Adamantylamides of benzimidazoline-3-acetic acids: synthesis and pharmacological properties.", Khimiko-Farmatsevticheskii Zhurnal, 1988, pp. 819-822, vol. 22(7), coden: Khfzan; ISSN: 0023-1134, XP008042581.

Badman et al., "The Gut and Energy Balance, Visceral Allies in the Obesity Wars.", Science, Mar. 25, 2005, pp. 1909-1014, vol. 307.

Baussane et al., "Asymmetric synthesis of 3-substituted pyrrolidones via α-alkylation of a chiral non-racemic γ-lactam.", Tetrahedron: Assymetry, 1998, pp. 797-804, vol. 9(5).

Blommaert et al., "Mono and Sequential BIS Solid Phase Alkylations of a (R)-Phenylglycinol Derived Pyrrolidinone Scaffold.", Heterocycles, 2001, pp. 2273-2278, vol. 55(12).

Bonnekessel et al., "Beilstein Institut zur Foerderung der Chemischen Wissenschaften Frankfurt am Main, DE". *Chem. Ber.* 1973, pp. 2890-2903, vol. 106, XP002248049.

Boyle, Craig D., "Recent advances in the discovery of 11β-HSD1 inhibitors.", Current Opinion in Drug Discovery & Development, 2008, pp. 495-511, vol. 11(4), The Thompson Corporation.

Caglioti et al., "Beilstein Institut zur Foerderung der Chemischen Wissenschaften Frankfurt am Main, DE.", *J. Org. Chem.*, 1968, pp. 2979-2981, vol. 33(7), XP002248043.

Camps, R., "Beilstein Institut zur Foerderung der Chemischen Wissenschaften, Frankfurt am Main, DE.", *Arch. Pharm.*, 1902, p. 358, vol. 240, XP002248047.

Chapman et al., "11β-HSD1, Inflammation, Metabolic Disease and Age-related Cognitive (dys)Function.", Neurochemical Research, 2008, pp. 624-636, vol. 33, Springer Science + Business media.

Chemical Abstract: Database Beilstein, Database accession No. 1481016, and 1481024, Amano, 1966.

Chemical Abstract: Database Beilstein, Database accession No. 5949999, Schmitz, E. et al (1982).

Chemical Abstract: Database Caplus, Database accession No. 1966:71362 Amano, T. 1966.

Chemical Abstract: Database Chemcats (Apr. 23, 2004) Database accession No. 2001:711911; XP002316807.

Chemical Abstract: Database Chemcats (Apr. 25, 2003) Database accession No. 2001:2280339; XP002316809.

Chemical Abstract: Database Chemcats (Aug. 11, 2003) Database accession No. 2001:1353682; XP002316808.

Chemical Abstract: Database Chemcats (Oct. 20, 2003) Database accession No. 2002:1350205 XP002316810.

Chemical Abstract: Database Chemcats (Oct. 20, 2003) Database accession No. 2002:1350218; XP002316811.

Chemical Abstract: Database Chemcats an 2002: 1350644; Oct. 2003; XP002354668, Abstract.

Division of Medical Chemistry Abstracts—234th ACS National Meeting Boston, MA, Aug. 19-23, 2007.

Forster, A., "Beilstein Institut zur Foerderung der Chemischen Wissenschaften Frankfurt am Main, DE.", *J. Chem. Soc.* 1904, pp. 1190, vol. 85, XP-002248034.

Garcia-Valverde et al., "A Diastereoselective Approach to Enantiopure 3-Substituted Pyrrolidines from Masked Lithium Homoenolates Derived from Norephedrine.", Tetrahedron, 1996, pp. 10761-10770, vol. 52(32).

(56) References Cited

OTHER PUBLICATIONS

Giuliano, L., "Beilstein Institut zur Foerderung der Chemischen Wissenschaften Frankfurt am Main, DE.", *Farmaco*, 1952, pp. 29-32, vol. 7, XP002248051.

Gryszkiewicz-T., "Beilstein Institut zur Foerderung der Chemischen Wissenschaften Frankfurt am Main, DE.", *Rocz. Chem*, 1934, pp. 335-337, vol. 14, XP002248048.

Huges et al., "11-Beta-hydroxysteroid dehydrogenase type 1 (11β-HSD1) inhibitors in Type 2 diabetes mellitus and obesity.", *Expert Opinion, Investig. Drugs*, 2008, pp. 481-496, vol. 17(4), Informa Healthcare, UK.

Jones et al., "Beilstein Institut zur Foerderung der Chemischen Wissenschaften Frankfurt am Main, DE.", *Tetrahedron*, 1965, pp. 2961-2966, vol. 21, XP002279296.

Katritzky et al., "Novel syntheses of enantiopure hexahydroimidazo[1,5-b]isoquinolines and tetrahydroimidazo[1,5-b]isoquinolin-1(5H)-ones via iminium cation cyclizations.", J. Org. Chem., vol. 67, 2002, pp. 8224-8229.

Kitagawa et al., "Beilstein Institut zur Foerderung der Chemischen Wissenschaften Frankfurt am Main, DE.", *Tetrahedron Lett.*, 1999, pp. 8827-8832, vol. 40(50), XP002279294.

Knunjanz, G. "Beilstein Institut zur Foerderung der Chemischen Wissenschaften Frankfurt am Main, DE.", IASKA6, 1958, pp. 1219-1221, XP002248040.

Koenig et al., "Beilstein Institut zur Foerderung der Chemischen Wissenschaften Frankfurt am Main, DE.", *Chem. Ber.*, 1965, p. 3712-3723, vol. 98, XP002248046.

Koetz, M., "Beilstein Institut zur Foerderung der Chemischen Wissenschaften Frankfurt am Main, DE.", *J. Prakt. Chem.*; 1926, p. 74, vol. 113, XP002248036.

Kuehne et al., "Beilstein Institut zur Foerderung der Chemischen Wissenschaften Frankfurt am Main, DE.", *J. Org. Chem.*, 1977, pp. 2082-2087, vol. 42(12), XP002248045.

Larsen et al., "A Modified Bischler-Napieralski Procedure for the Synthesis of 3-Aryl-3,4-dihydroisoquinolines.", Journal of Organic Chemistry, 1991, pp. 6034-6038, vol. 56(21), American Chemical Society.

Latypov et al., "Determination of the absolute stereochemistry of alcohols and amines by NMR of the group directly linked to the chiral derivatizing reagent.", *Tetrahedron*, 2001, pp. 2231-2236, vol. 57(11), XP004230761.

Lavrova et al., "Synthesis of 2-aminoadamantane and its N-substituted derivatives.", *Zhurnal Organicheskoi Khimii* (1974), pp. 761-765, vol. 10(4).

Markownikow, "Beilstein Institut zur Foerderung der Chemischen Wissenschaften, Frankfurt am Main, DE.", *Chem. Ber.*, 1892, p. 3357, vol. 25, XP002248050.

Masuzaki et al., "A Transgenic Model of Visceral Obesity and the Metabolic Syndrome.", Science, Dec. 7, 2001, pp. 2166-2170, vol. 294.

Mizuno, K., "Beilstein Institut zur Foerderung der Chemischen Wissenschaften Frankfurt am Main, DE.", *J. Chem. Soc. Chem. Commun.*, 1975, p. 308, XP002248042.

Montague et al., "Perspective in Diabetes. The Perils of Portliness, Causes and Consequences of Visceral Adiposity.", Diabetes, Jun. 2000, pp. 883-888, vol. 49.

Murahashi, S., "Synthesis of Phthalimidines from Schiff Bases and Carbon Monoxide.", J. Am. Chem. Soc., 1955, pp. 6403-6404, vol. 77.

Nikiforov et al., "Synthesis and Absolute Configuration of Diastereomeric 3-Substituted 1-[1'(S)-Phenylethyl]-2-Pyrrolidinones.", Doklady Bolgarskoi Akademii Nauk, 1986, vol. 39(3), pp. 73-76.

Oda et al., "An efficient route to chiral, non-racemic 3-alkyl-3-arylpyrrolidines. Improved stereoselectivity in alkylation of bicyclic lactams and the effect of leaving groups.", Tetrahedron Letters, pp. 8193-8197, 2000, vol. 41(43).

Olah et al., "Beilstein Institut zur Foerderung der Chemischen Wissenschaften Frankfurt am Main, DE.", *Synthesis*, 1979, pp. 274-276, XP002248039.

Olsen, C. E., "Beilstein Institut zur Foerderung der Chemischen Wissenschaften Frankfurt am Main, DE.", *Acta Chem. Scand. Ser. B.*, 1975, pp. 953-962, XP002248044.

Pharmas-Cutting-Edge; http://pharmaweblog.com/blog/category/rd/preclinical (1 page),2007.

Pop et al., "Versatile Acylation of N-Nucleophiles Using a New Polymer-Supported 1-Hydroxybenzotriazole Derivative.", *J. Org. Chem.*, 1997, pp. 2594-2603, vol. 62.

Rauz et al., "Expression and Putative Role of 11β-Hydroxysteroid Dehydrogenase Isozymes within the Human Eye.", Invest. Ophtalmol. Vis. Science, Aug. 2001, pp. 2037-2042, vol. 42(9).

Rufer et al., "Neue Acylierte 2-(4-Aminiophenyl)-Propionsaeurenals Potentiele Antiplogistica.", European Journal of Medicinal Chemistry, Editions Scientifique Elsevier,Paris, FR, vol. 13, No. 2, Mar. 1978 (Mar. 1978), pp. 193-198, XP001068547 ISSN: 0223-5234 compounds 6A-7.

Sabri et al., "Synthesis and antibacterial activity of some new N-(3-methyl-2-quinoxaloyl) amino alcohols and amine 1,4-dioxides.", *J. Chem.*, Eng. Data, 1984, pp. 229-231, vol. 29(2), XP002279298.

Schroth et al., "Beilstein Institut zur Foerderung der Chemischen Wissenschaften Frankfurt am Main, DE.", *J. Prakt. Chem.*, 1983, pp. 787-802, vol. 325(5), XP002248035.

Starnes et al., "Beilstein Institut zur Foerderung der Chemischen Wissenschaften Frankfurt am Main, DE.", *J. Amer. Chem. Soc.*, 2001, pp. 4659-4669, vol. 123(20), XP002248037.

Stewart et al., "Cortisol, 11β-hydroxysteroid dehydrogenase type 1 and central obesity.", Trends. Endocrin. Metabol., 2002, pp. 94-96, vol. 13.

Sugasawa et al., "Beilstein Institut zur Foerderung der Chemischen Wissenschaften Frankfurt am Main, DE.", 1952, p. 7461, vol. 72, XP002248038.

Takahashi, T., "Synthesis of analgesics. XX. Camphane derivatives. 2.", *Chem. Abst.*, 1959, pp. 162-166, vol. 79, XP002248033.

Terauchi et al., "Beilstein Institut zur Foerderung der Chemischen Wissenschaften Frankfurt am Main, DE.", *Tetrahedron*, 2003, pp. 587-592, vol. 14(5), XP002279295.

Treatment of Dementia: Anything New ?; http://www.medscape.com/viewarticle/547499_print (8 pages), 2006.

Wamil et al., "Inhibition of 11β-hydroxysteriod dehydrogenase type 1 as a promising therapeutic target.", *Drug Discovery Today*, Jul. 2007, pp. 504-520, vol. 12(13/14), Elsevier.

Yamato et al., "Beilstein Institut zur Foerderung der Chemischen Wissenschaften Frankfurt am Main, DE.", *Chem. Pharm. Bull.*, 1988, p. 3453-3461, vol. 36(9), XP002279297.

Yau et al., "Targeting 11β-hydroxysteroid dehydrogenase type 1 in brain: therapy for cognitive aging?", *Expert Review of Endrocrinology & Metabolism*, 2006, pp. 527-536, vol. 1(4), Future Drugs Ltd.

Young, C., "Beilstein Institut zur Foerderung der Chemischen Wissenschaften, Frankfurt am Main, DE.", *J. Chem. Soc.*, 1898, p. 365, vol. 73, XP-002248041.

Zhou et al., "Glucocorticoid effects on extracellular matrix proteins and integrins in bovine trabecular meshwork cells in relation to glaucoma.", *Int. J. Mol. Med.*, 1998, vol. 1, pp. 339-346.

International Search Report relating to International Patent Application No. PCT/EP2005/051968. Date of mailing of International Search Report, Aug. 17, 2005.

Written Opinion relating to International Patent Application No. PCT/EP2005/051968. Date of mailing of International Written Opinion, Aug. 17, 2005.

\* cited by examiner

PYRROLIDIN-2-ONE AND PIPERIDIN-2-ONE DERIVATIVES AS 11-BETA HYDROXYSTEROID DEHYDROGENASE INHIBITORS

CROSS REFERENCE TO RELATED APPLICATIONS

This application is a divisional application of U.S. application Ser. No. 14/656,752, filed Mar. 13, 2015, which is a divisional application of U.S. application Ser. No. 11/632,675, filed Jan. 10, 2008, which is the national stage of Application No. PCT/EP2005/051968, filed Apr. 29, 2005, which application claims priority from European Patent Appl. No. 04101991.0, filed May 7, 2004.

The metabolic syndrome is a disease with increasing prevalence not only in the Western world but also in Asia and developing countries. It is characterised by obesity in particular central or visceral obesity, type 2 diabetes, hyperlipidemia, hypertension, arteriosclerosis, coronary heart diseases and eventually chronic renal failure (C. T. Montague et al. (2000), Diabetes, 49, 883-888).

Glucocorticoids and 11β-HSD1 are known to be important factors in differentiation of adipose stromal cells into mature adipocytes. In the visceral stromal cells of obese patients, 11β-HSD1 mRNA level is increased compared with subcutaneous tissue. Further, adipose tissue over-expression of 11β-HSD1 in transgenic mice is associated with increased corticosterone levels in the adipose tissue, visceral obesity, insulin sensitivity, Type 2 diabetes, hyperlipidemia and hyperphagia (H. Masuzaki et al (2001), Science, 294, 2166-2170). Therefore, 11β-HSD1 is most likely be involved in the development of visceral obesity and the metabolic syndrome.

Inhibition of 11β-HSD1 results in a decrease in differentiation and an increase in proliferation of adipose stromal cells. Moreover, glucocorticoid deficiency (adrenalectomy) enhances the ability of insulin and leptin to promote anorexia and weight loss, and this effect is reversed by glucocorticoid administration (P. M. Stewart et al (2002), Trends Endocrin. Metabol, 13, 94-96). These data suggest that enhanced reactivation of cortisone by 11β-HSD1 may exacerbate obesity and it may be beneficial to inhibit this enzyme in adipose tissue of obese patients.

Obesity is also linked to cardiovascular risks. There is a significant relationship between cortisol excretion rate and HDL cholesterol in both men and women, suggesting that glucocorticoids regulate key components of cardiovascular risk. In analogy, aortic stiffness is also associated with visceral adiposity in older adults.

Glucocorticoids and Glaucoma

Glucocorticoids increase the risk of glaucoma by raising the intraocular pressure when administered exogenously and in certain conditions of increased production like in Cushing's syndrome. Corticosteroid-induced elevation of intra ocular pressure is caused by increased resistance to aqueous outflow due to glucocorticoid induced changes in the trabecular meshwork and its intracellular matrix. Zhou et al. (Int J Mol Med (1998) 1, 339-346) also reported that corticosteroids increase the amounts of fibronectin as well as collagen type I and type IV in the trabecular meshwork of organ-cultured bovine anterior segments.

11β-HSD1 is expressed in the basal cells of the corneal epithelium and the non-pigmented epithelial cells. Glucocorticoid receptor mRNA was only detected in the trabecular meshwork, whereas in the non-pigmented epithelial cells mRNA for the glucocorticoid-, mineralocorticoid receptor and 11β-HSD1 was present. Carbenoxolone administration to patients resulted in a significant decrease in intra-ocular pressure (S. Rauz et al. (2001), Invest. Ophtalmol. Vis. Science, 42, 2037-2042), suggesting a role for HSD1-inhibitors in treating glaucoma.

Accordingly, the underlying problem to be solved by the present invention was to identify potent 11β-HSD inhibitors, with a high selectivity for 11β-HSD1, and the use thereof in treating pathologies associated with excess cortisol formation such as obesity, diabetes, obesity related cardiovascular diseases, and glaucoma. As shown hereinbelow, the 3-substituted 2-pyrrolidinone derivatives of formula (I) were found to be useful as a medicine, in particular in the manufacture of a medicament for the treatment of pathologies associated with excess cortisol formation.

Blommaert A. et al. (Heterocycles (2001), 55(12), 2273-2278) provides the preparation of piperidine- and pyrrolidinone-like polymer supported (R)-phenylglycinol-derived scaffolds and in particular discloses 2-Pyrrolidinone, 1-[(1R)-2-hydroxy-1-phenylethyl]-3-methyl-3-(phenylmethyl)- and 2-Pyrrolidinone, 1-[(1R)-2-hydroxy-1-phenylethyl]-3-(phenylmethyl)-, (3R).

Bausanne I. et al. (Tetrahedron: Assymetry (1998), 9(5), 797-804) provides the preparation of 3-substituted pyrrolidinones via α-alkylation of a chiral non-racemic γ-lacton and in particular discloses 1-(2-hydroxy-1-phenylethyl)-3-benzylpyrrolidin-2-one.

US 2001/034343; U.S. Pat. No. 6,211,199; U.S. Pat. No. 6,194,406; WO 97/22604 and WO 97/19074 are a number of patent applications filed by Aventis Pharmaceuticals Inc. providing 4-(1H-benzimidazol-2-yl)[1,4]diazepanes useful for the treatment of allergic diseases. In these applications the 3-substituted pyrrolidinones of the present invention are disclosed as intermediates in the synthesis of said 4-(1H-benzimidazol-2-yl)[1,4]diazepanes. These applications in particular disclose; 2-Pyrrolidinone, 3-[(4-fluorophenyl)methyl]-1-[(1S)-1-phenylethyl]- and 2-Pyrrolidinone, 3-[(4-fluorophenyl)methyl]-1-[(1R)-1-phenylethyl]-.

The general synthesis and absolute configuration of diastereomeric 3-substituted 1-[1'-(S)-phenylethyl]-2-pyrrolidinones is provided by Nikiforov T. T. and Simeonov E. E. in Doklady Bolgarskoi Academii Nauk (1986), 39(3), 73-76. It exemplifies the synthesis of 2-Pyrrolidinone, 3-methyl-3-[(4-methylphenyl)methyl]-1-(1-phenylethyl)-, [S—(R*,R*)]; 2-Pyrrolidinone, 3-methyl-3-[(4-methylphenyl)methyl]-1-(1-phenylethyl)-, [S—(R*, S*)]; 2-Pyrrolidinone, 3-[(4-methylphenyl)methyl]-1-(1-phenylethyl)-, [S—(R*, R*)] and 2-Pyrrolidinone, 3-[(4-methylphenyl)methyl]-1-(1-phenylethyl)-, [S—(R*, S*)].

However, in none of the cited documents the therapeutic application of the 3-substituted 2-pyrrolidinone derivatives of the present invention has been disclosed. Accordingly, in a first aspect this invention concerns compounds of formula (I)

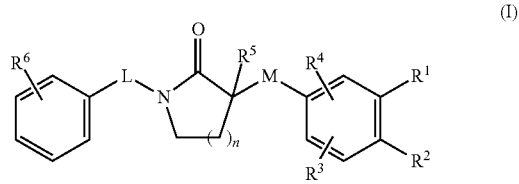

the N-oxide forms, the pharmaceutically acceptable addition salts and the stereochemically isomeric forms thereof, wherein n is 1 or 2;

L represents a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl, hydroxy, $C_{1-3}$alkyloxy- or phenyl-$C_{1-4}$alkyl;

M represents a direct bond or a $C_{1-3}$alkyl linker optionally substituted with one or two substituents selected from hydroxy, $C_{1-4}$alkyl or $C_{1-4}$alkyloxy;

$R^1$ and $R^2$ each independently represent hydrogen, halo, cyano, hydroxy, $C_{1-4}$alkyl optionally substituted with halo, $C_{1-4}$alkyloxy- optionally substituted with one or where possible two or three substituents selected from hydroxy, $Ar^1$ and halo;

or $R^1$ and $R^2$ taken together with the phenyl ring to which they are attached form naphtyl or 1,3-benzodioxolyl, wherein said naphtyl or 1,3-benzodioxolyl are optionally substituted with halo;

$R^3$ represents hydrogen, halo, $C_{1-4}$alkyl, $C_{1-4}$alkyloxy-, cyano or hydroxy;

$R^4$ represents hydrogen, halo, $C_{1-4}$alkyl, $C_{1-4}$alkyloxy-, cyano or hydroxy;

$R^5$ represents hydrogen, $C_{1-4}$alkyl or $Ar^2$—$C_{1-4}$alkyl;

$R^6$ represents hydrogen, halo, $C_{1-4}$alkyl or $C_{1-4}$alkyoxy-;

$Ar^1$ and $Ar^2$ each independently represent phenyl or naphtyl wherein said phenyl and naphtyl are optionally substituted with $C_{1-4}$alkyl, $C_{1-4}$alkyloxy-, or phenyl-$C_{1-4}$alkyl;

for use as a medicine.

As used in the foregoing definitions and hereinafter, halo is generic to fluoro, chloro, bromo and iodo; $C_{1-3}$alkyl defines straight and branched chain saturated hydrocarbon radicals having from 1 to 4 carbon atoms such as, for example, methyl, ethyl, propyl, 1-methylethyl and the like; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-4}$alkyloxy defines straight or branched saturated hydrocarbon radicals having form 1 to 3 carbon atoms such as methoxy, ethoxy, propyloxy, 1-methylethyloxy and the like; $C_{1-4}$alkyloxy defines straight or branched saturated hydrocarbon radicals having form 1 to 4 carbon atoms such as methoxy, ethoxy, propyloxy, butyloxy, 1-methylethyloxy, 2-methylpropyloxy and the like.

The pharmaceutically acceptable addition salts as mentioned hereinabove are meant to comprise the therapeutically active non-toxic acid addition salt forms, which the compounds of formula (I), are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I), are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I), as well as the salts thereof, are able to form. Such solvates are for example hydrates, alcoholates and the like.

The term stereochemically isomeric forms as used hereinbefore defines the possible different isomeric as well as conformational forms which the compounds of formula (I), may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I), both in pure form or in admixture with each other are intended to be embraced within the scope of the present invention.

The N-oxide forms of the compounds of formula (I), are meant to comprise those compounds of formula (I) wherein one or several nitrogen atoms are oxidized to the so-called N-oxide.

An interesting group of compounds consists of those compounds of formula (I) wherein one or more of the following restrictions apply:

(i) n is 1 or 2; in particular n is 1

(ii) L represents a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl, hydroxy, $C_{1-3}$alkyloxy- or phenyl-$C_{1-4}$alkyl; in particular L represents a $C_1$-linker optionally substituted with $C_{1-4}$alkyl; preferably L represents a $C_1$-linker substituted with $C_{1-4}$alkyl, more preferably a $C_1$-linker substituted with methyl;

(iii) M represents a direct bond or a $C_{1-2}$alkyl optionally substituted with one or two substituents selected from hydroxy, $C_{1-4}$alkyl or $C_{1-4}$alkyloxy-; in particular M represents a $C_{1-2}$alkyl optionally substituted with one or two substituents selected from hydroxy, $C_{1-4}$alkyl or $C_{1-4}$alkyloxy-; preferably M represents a $C_1$-linker optionally substituted with $C_{1-4}$alkyl;

(iv) $R^1$ represents hydrogen, hydroxy, halo, $C_{1-4}$alkyl, $C_{1-4}$alkyloxy-, or $C_{1-4}$alkyloxy substituted with halo;

(v) $R^2$ represents hydrogen, halo, $C_{1-4}$alkyl, $C_{1-4}$alkyloxy- or $Ar^1$—$C_{1-4}$alkyloxy-;

(vi) $R^3$ represents hydrogen, halo, $C_{1-4}$alkyl, $C_{1-4}$alkyloxy- or cyano;

(vii) $R^4$ represents hydrogen, halo, $C_{1-4}$alkyl or $C_{1-4}$alkyloxy-;

(viii) $R^5$ represents hydrogen, $C_{1-4}$alkyl or $Ar^2$—$C_{1-4}$alkyl; in particular hydrogen;

(ix) $R^6$ represents hydrogen, halo, or $C_{1-4}$alkyloxy; in particular hydrogen, chloro, fluoro, bromo or methoxy;

(x) $Ar^1$ represents phenyl;

(xi) $Ar^2$ represents phenyl or naphtyl;

Another group of compounds consists of those compounds of formula (I) wherein one or more of the following restrictions apply:

(i) n is 1;

(ii) L represents a $C_{2-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl, hydroxy, $C_{1-3}$alkyloxy- or phenyl-$C_{1-4}$alkyl;
(iii) M represents a $C_{2-3}$alkyl linker optionally substituted with one or two substituents selected from hydroxy, $C_{1-4}$alkyl or $C_{1-4}$alkyloxy;
(iv) $R^5$ represents $Ar^2$—$C_{1-4}$alkyl;
(v) $R^6$ represents halo, $C_{1-4}$alkyl or $C_{1-4}$alkyloxy-.

Another group of interesting compounds consists of those compounds of formula (I) wherein one or more of the following restrictions apply:
(i) n is 1;
(ii) L represents a $C_{1-3}$alkyl linker optionally substituted with ethyl or methyl, in particular L represents a $C_1$-linker substituted with ethyl or methyl;
(iii) M represents a $C_1$-linker optionally substituted methyl;
(iv) $R^1$ and $R^2$ represent $C_{1-4}$alkyloxy, in particular methoxy or $R^1$ and $R^2$ taken together with the phenyl ring to which they are attached form 1,3-benzodioxolyl substituted with halo;
(v) $R^3$ represents chloro, fluoro, methyl or hydrogen;
(vi) $R^4$ represents chloro, fluoro or methyl;
(vii) $R^5$ represents hydrogen;
(viii) $R^6$ represents hydrogen.

A further group of compounds according to the present invention are those compounds wherein $R^6$ is at the para position, L represents a $C_2$-alkyl linker and M represents a $C_1$-linker.

Another interesting group of compounds are those compounds of formula (I) wherein L represents a $C_1$-linker substituted with a $C_{1-4}$alkyl, $C_{1-4}$alkyloxy$C_{1-4}$alkyl-, hydroxy$C_{1-4}$alkyl- or phenyl$C_{1-4}$alkyl- wherein said $C_{1-4}$alkyl, $C_{1-4}$alkyloxy$C_{1-4}$alkyl-, hydroxy$C_{1-4}$alkyl- or phenyl$C_{1-4}$alkyl- is in the S-configuration In a preferred embodiment the compounds of formula (I) are selected from the group consisting of:
3-[(2,6-Dichlorophenyl)methyl]-1-(1-phenylpropyl)-2-pyrrolidinone;
3-[(2,6-Difluorophenyl)methyl]-1-(1-phenylethyl)-2-pyrrolidinone;
3-[(2,6-Dimethylphenyl)methyl]-1-(1-phenylethyl)-2-piperidinone;
3-[(6-Chloro-1,3-benzodioxol-5-yl)methyl]-1-(1-phenylethyl)-2-pyrrolidinone;
3-[1-(2-Methylphenyl)ethyl]-1-(1-phenylethyl)-2-pyrrolidinone;
3-[(2-Chloro-3,4-dimethoxyphenyl)methyl]-1-(1-phenylethyl)-2-pyrrolidinone;
3-[(2,6-Dichlorophenyl)methyl]-1-(2-phenylethyl)-2-pyrrolidinone;
3-[(2,6-Dimethylphenyl)methyl]-1-(1-phenylethyl)-2-piperidinone, or
3-[(2-Methylphenyl)methyl]-1-(1-phenylethyl)-2-pyrrolidinone.

the N-oxides, pharmaceutically acceptable addition salts or a stereochemically isomeric forms thereof.

In a more preferred embodiment the compounds of formula (I) are selected from the group consisting of
3-[(2,6-Dichlorophenyl)methyl]-1-(1-phenylpropyl)-2-pyrrolidinone;
3-[(2,6-Difluorophenyl)methyl]-1-(1-phenylethyl)-2-pyrrolidinone;
3-[(2,6-Dimethylphenyl)methyl]-1-(1-phenylethyl)-2-piperidinone;
3-[(6-Chloro-1,3-benzodioxol-5-yl)methyl]-1-(1-phenylethyl)-2-pyrrolidinone;
3-[1-(2-Methylphenyl)ethyl]-1-(1-phenylethyl)-2-pyrrolidinone;
3-[(2,6-Dichlorophenyl)methyl]-1-(2-phenylethyl)-2-pyrrolidinone;
3-[(2-Methylphenyl)methyl]-1-(1-phenylethyl)-2-pyrrolidinone.

the N-oxides, pharmaceutically acceptable addition salts or a stereochemically isomeric forms thereof.

In a further aspect the present invention provides any of the aforementioned group of compounds for use as a medicine. In particular in the treatment or prevention of parthologies associated with excess cortisol formation such as obesity, diabetes, obesity related cardiovascular diseases and glaucoma.

The 1,3-pyrrolidinine derivatives of the present invention are generally prepared by alkylation of the appropriate lactam (II) with an appropriate alkyl halide (III) in the presence of a base such as for example (diisopropylamino) lithium (LDA) or sec-butyllithium, optionally in the present of a co-solvent such as for example N,N',N''-Hexamethylphosphoramide (HMPA) or a salt such as for example LiBr (Scheme 1). This reaction is usually performed in an inert solvent such as for example diisopropylether, tetrahydrofuran or methylene chloride. The reaction temperature and the reaction time may be altered depending on the starting material or reagents but is usually performed within a couple of hours at low temperatures (−50° C.--90° C.). In some cases the coupling reaction is slow and the mixture has to be kept until completion. In these cases the temperature could be enhanced up to (−10° C.--30° C.).

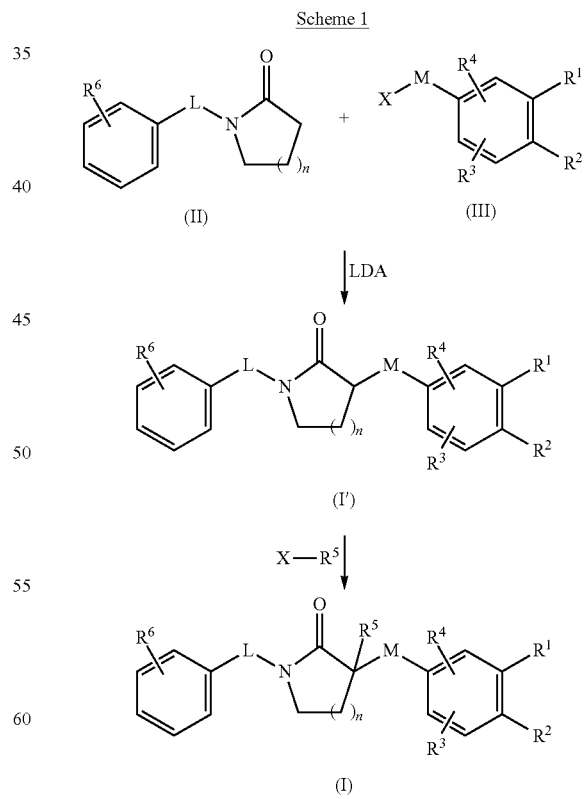

Scheme 1

The appropriate lactam of formula (II) hereinbefore, is generally prepared by reacting the known amines of formula (IV) with either 4-chlorobutanoyl chloride or 5-chloropentanoyl chloride in the presence of a base, such as for example sodium hydroxide, potassium hydroxide, sodiumcarbonate or sodium hydrogen carbonate, in an appropriate solvent such as for example dichloromethane, diisopropylether, tetrahydrofuran or methylene chloride (Scheme 2). The reaction is typically performed in two steps, wherein, in a first step the 4-chlorobutanoyl chloride or 5-chloropentanoyl chloride is added to the amine of formula (IV) under basic conditions, using for example triethylamine in dichloromethane, to form the amide of formula (V). In the second step, upon addition of a strong base such as sodium hydroxide, an internal nucleophilic addition reaction provides the lactam of formula (II).

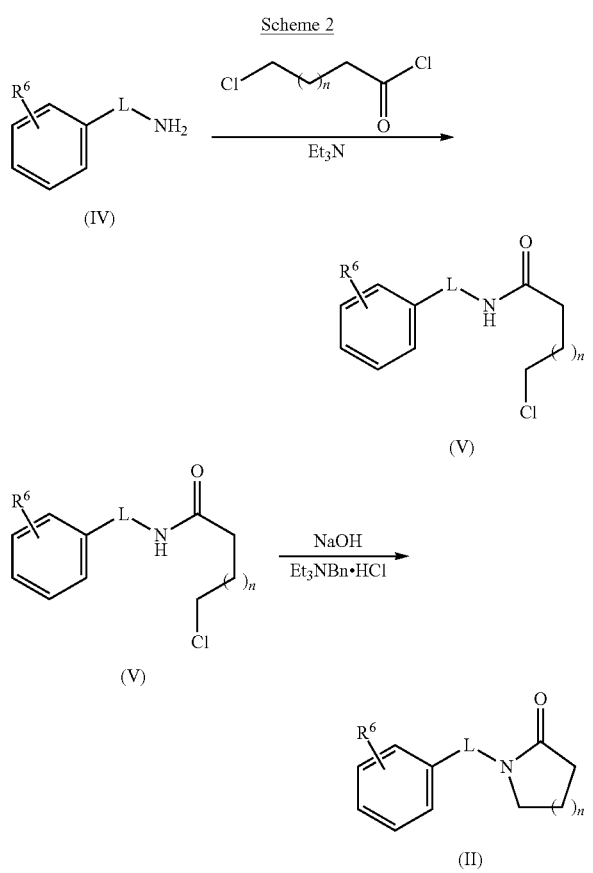

The amines of formula (IV) are generally prepared using art known techniques, see for instance in; "Introduction to organic chemistry" Streitweiser and Heathcock—Macmillan Publishing Co., Inc.—second edition—New York—Section 24.6 p 742-753, and comprise synthesis through indirect alkylation of the appropriate (hetero)aryl 113 halides in particular by the Gabriel synthesis, through reduction of the corresponding nitro or nitrille compounds, through reductive amination using for example the Eschweiler-Clarke reaction and in particular fore those compounds of formula (I) wherein L represents an optionally substituted $C_1$-alkyl, through the reduction of oximes (VI) which may be prepared from aldehydes or ketones (VII) by reaction with hydroxylamine (scheme 3). In this latter case the oximes are reduced by lithium aluminium hydride or catalytic hydrogenation using an appropriate catalysator such as Raney Nickel, said reduction being performed in an inert anhydrous solvent such as ether or tetrahydrofuran (THF).

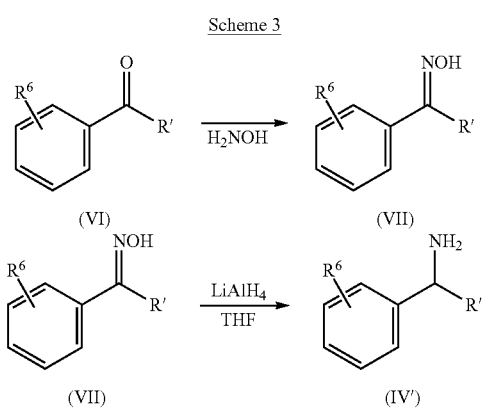

Wherein R' represents a $C_{1-4}$alkyl, $C_{1-3}$alkyloxy-$C_{1-4}$alkyl, hydroxy-$C_{1-4}$alkyl, $C_{1-3}$alkyloxy- or phenyl-$C_{1-4}$alkyl- and $R^6$ is defined as for the compounds of formula (I).

Further examples for the synthesis of compounds of formula (I) using anyone of the above mentioned synthesis methods, are provided in the experimental part hereinafter.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer;

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$alkyl or benzyl esters.

The protection and deprotection of functional groups may take place before or after a reaction step.

The use of protecting groups is fully described in 'Protective Groups in Organic Synthesis' $2^{nd}$ edition, T W Greene & P G M Wutz, Wiley Interscience (1991).

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I), can also be converted into each other following art-known procedures of functional group transformation of which some examples are mentioned hereinabove.

The compounds of formula (I), may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I), may be obtained by the application of art-known procedures. Diastereomers may be separated by physical methods such as selective crystallization and chromatographic techniques, e.g. counter-current distribution, liquid chromatography and the like.

Some of the compounds of formula (I), and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines, in particular to treat pathologies associated with excess cortisol formation such as for example, obesity, diabetes, obesity related cardiovascular diseases, and glaucoma.

As described in the experimental part hereinafter, the inhibitory effect of the present compounds on the 11β-HSD1-reductase activity (conversion of cortison into cortisol) has been demonstrated in vitro, in an enzymatic assay using the recombinant 11b-HSD1 enzyme, by measuring the conversion of cortison into cortisol using HPLC purification and quantification methods. 11β-HSD1-reductase inhibition was also demonstrated in vitro, in a cell based assay comprising contacting the cells, expressing 11β-HSD1 with the compounds to be tested and assessing the effect of said compounds on the formation of cortisol in the cellular medium of these cells. The cells preferably used in an assay of the present invention are selected from the group consisting of mouse fibroblast 3T3-L1 cells, HepG2 cells, pig kidney cell, in particular LCC-PK1 cells and rat hepatocytes.

Accordingly, the present invention provides the compounds of formula (I) and their pharmaceutically acceptable N-oxides, addition salts, quaternary amines and stereochemically isomeric forms for use in therapy. More particular in the treatment or prevention of parthologies associated with excess cortisol formation such as obesity, diabetes, obesity related cardiovascular diseases and glaucoma. The compounds of formula (I) and their pharmaceutically acceptable N-oxides, addition salts, quaternary amines and the stereochemically isomeric forms may hereinafter be referred to as compounds according to the invention.

In view of the utility of the compounds according to the invention, there is provided a method for the treatment of an animal, for example, a mammal including humans, suffering from a pathology associated with excess cortisol formation, which comprises administering an effective amount of a compound according to the present invention. Said method comprising the systemic or topical administration of an effective amount of a compound according to the invention, to warm-blooded animals, including humans.

It is thus an object of the present invention to provide a compound according to the present invention for use as a medicine. In particular to use the compound according to the present invention in the manufacture of a medicament for treating pathologies associated with excess cortisol formation such as for example, obesity, diabetes, obesity related cardiovascular diseases, and glaucoma.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.001 mg/kg to 500 mg/kg body weight, in particular from 0.005 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

EXPERIMENTAL PART

Hereinafter, the term 'RT' means room temperature, 'THF' means tetrahydrofuran, 'Et$_2$O' means diethylether, 'DCM means dichloromethane, 'LDA' means (diisopropylamino)lithium.

A. Preparation of the Intermediates

Example A1

Preparation of Intermediate 1

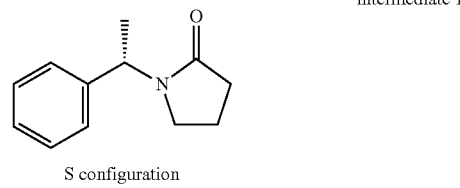

intermediate 1

S configuration

To a stirred solution of alfa-(S)-methyl benzylamine (0.05 mol) and triethylamine (Et$_3$N) (0.055 mol) in DCM (200 ml) was added dropwise a solution of 4-chlorobutanoyl chloride (0.055 mol) in DCM (100 ml) at −10° C. After the addition, the reaction mixture was stirred at room temperature until total conversion (TLC monitoring). The reaction mixture was washed twice with 1N HCl. To the organic phase were added 100 ml of 50% sodium hydroxide solution together with benzyl-triethyl ammonium chloride (0.05 mol). The mixture was stirred vigorously at room temperature overnight. The thus obtained reaction mixture was washed with 1N HCl, 5% NaHCO$_3$ solution, water and brine. The organic phase was separated, dried over magnesium sulphate and concentrated to give 9.5 g of intermediate 1 as colourless oil.

Alternatively intermediate 1 is prepared according to the following reaction scheme;

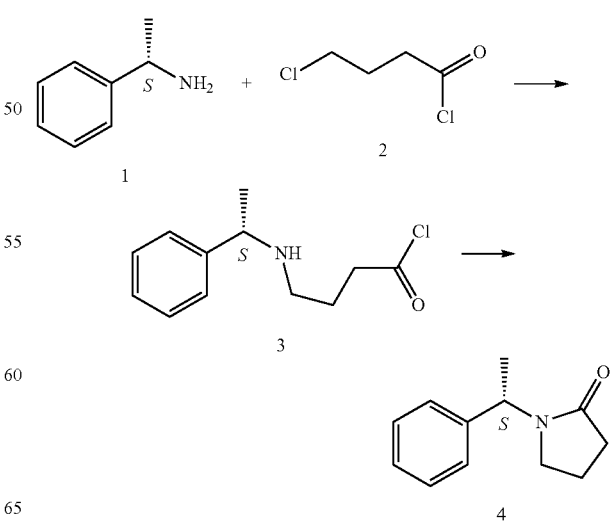

To a stirred solution of 7 ml Et₃N in 300 ml CH₂Cl₂ was introduced dropwise within 0.5 hour a solution of 6.00 g (0.0495 mol) 1 in 100 ml CH₂Cl₂. The mixture was stirred at RT until no starting amine 1 was monitored by TLC (eluted with Et₂O; the formation of the intermediate 2 could be monitored $R_f$=0.5). The mixture was washed with 2N HCl (to remove the Et₃N still present). To the reaction mixture were introduced TEBA (benzyltriethylammonium chloride) 1.13 g (0.00495 mol) and NaOH (aq.) (50 g in 60 ml H₂O). The mixture was stirred overnight, organic layer was separated and acidified with 2N HCl. It was washed with NaHCO₃ (5%), H₂O and dried (NaSO₄). After evaporation of the solvent 10.10 g crude product were isolated. It was chromatographed (column h=260 mm, Ø=46 mm, 195 g silicagel 230-400 mesh, eluent Et₂O) to give 1.43 g of intermediate 3 and 7.28 g of 4 (78%).

NMR data for 4: CDCl3, 1.52 (d, 3H, CH₃); 1.93 (m, 2H, CH₂); 2.42 (m, 2H, CH₂); 2.99 and 3.31 (2×m, $H^A$ and $H^B$, NCH₂); 5.50 (quart, 1H, NCH); 7.32-7.48 (m, 5H-aromatic).

Example A2 a) Preparation of Intermediate 5

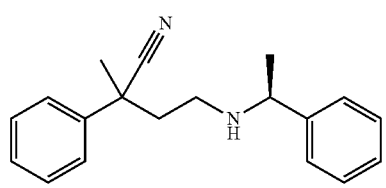

intermediate 5

A mixture of α-methyl-α-(2-oxoethyl)-benzeneacetonitrile (0.0086 mol) and (S)-α-methyl-benzenemethanamine (0.009 mol) in methanol (50 ml) was hydrogenated overnight with palladium on activated carbon (0.5 g) as a catalyst in the presence of a thiophene solution (1 ml). After uptake of hydrogen (1 equiv.), the catalyst was filtered off and the filtrate was evaporated, yielding 2.2 g of intermediate 5.

b) Preparation of Intermediate 6

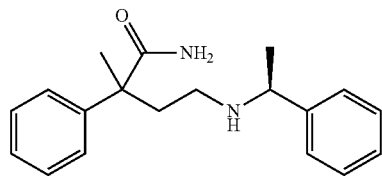

intermediate 6

A mixture of intermediate 5 (0.007 mol) in sulfuric acid (25 ml) was stirred at room temperature over the weekend. The reaction mixture was poured out into ice, then neutralised with a NaOH solution. (50%) and extracted with dichloromethane. The organic layer was separated, washed, dried, filtered and the solvent was evaporated, yielding 1.8 g (85.7%) of intermediate 6.

c) Preparation of Intermediate 7

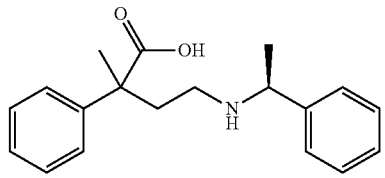

intermediate 7

·HBr

A mixture of intermediate 6 (0.0057 mol) in hydrobromic acid (48%) (50 ml) was stirred and refluxed for 1 hour, then for 3 hours. The reaction mixture was cooled and filtered, yielding 1.4 g of intermediate (7).

B. Preparation of the Compounds

Example B1

Preparation of Compound 1

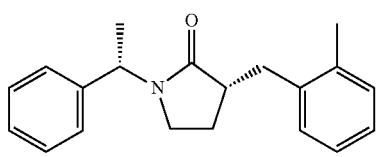

compound 1

And of Compound 2

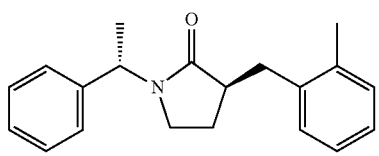

compound 2

To a stirred solution of 0.60 g (3.17 mmol) of intermediate 1 in 15 ml THF, cooled to −80° C., were added 1.2 equivalents of LDA (2M solution in THF/heptane/ethylbenzene) and the mixture was stirred for 30-45 minutes at −80° C. The corresponding benzylhalogenide, i.e. 1-methyl-2-chloromethylbenzene (1.05 equivalents) was added at −80° C. and the reaction mixture was stirred 1 hour at this temperature and for one additional hour at −60° C. The reaction was monitored by TLC and kept at −60° C. until completion. The thus obtained reaction mixture was hydrolized with 2N HCl, extracted with Et₂O, washed with 5% aq. NaHCO₃ and dried over Na₂SO₄. The purification of the diastereoisomers occurred by column chromatography on silica gel (230-400 mesh) with petroleum ether/Et₂O (from 2:1 to 4:1 depending on the corresponding compound), yielding compounds 1 and 2.

Example B2

Preparation of Compound 13 compound 13

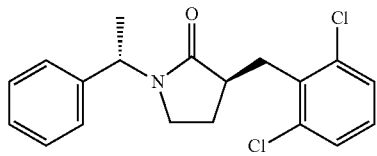

And of Compound 14 compound 14

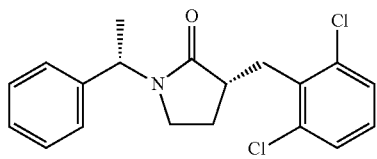

In a flame dried Schlenk-flask 0.80 g (4.23 mmol) of intermediate 1 were dissolved in 5 ml THF and cooled to −80° C. LDA (1.3 equivalent, 2.7 ml, ca. 2M commercial solution in THF/heptane/ethylbenzene) was introduced via syringe and the mixture was stirred for 30 minutes at −80° C. 2,6-Dichlorobenzyl bromide (1.42 g, 5.92 mmol) was introduced in solid form and the reaction mixture was stirred for 30 minutes at −80° C. until completion of the reaction (proved by TLC). The mixture was quenched with 2N HCl, then extracted with $Et_2O$ and the organic layer washed with $NaHCO_3$ (5% aq.), $H_2O$, and dried with $Na_2SO_4$. After evaporation of the solvent 1.81 g of the crude product were isolated. It was chromatographed (column h=580 mm, Ø=32 mm, 180 g silicagel 230-400 mesh, eluent petroleum ether/$Et_2O$=5:1) to give 0.61 g Compound 14 ( ) (colourless crystals m.p. 75-76° C.) and 0.75 g Compound 13 ( ) (colourless crystals m.p. 98-99° C.), corresponds to 93% total yield.

Table 1 lists the compounds that were prepared according to the above Examples.

TABLE 1

| | |
|---|---|
| 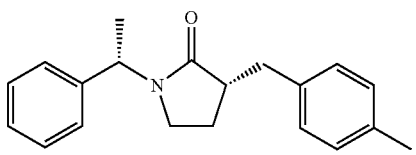 [SMILES: Cc1ccc(C[C@@H]2CCN([C@@H](C)c3ccccc3)C2=O)cc1] | Co. No. 3 |
| 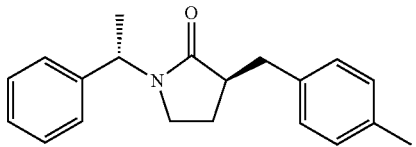 [SMILES: Cc1ccc(C[C@H]2CCN([C@@H](C)c3ccccc3)C2=O)cc1] | Co. No. 4 |
| 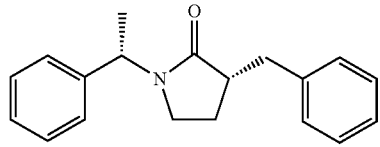 [SMILES: C[C@@H](c1ccccc1)N1CC[C@@H](Cc2ccccc2)C1=O] | Co. No. 5 |
| 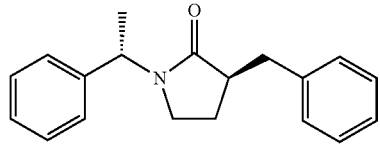 [SMILES: C[C@@H](c1ccccc1)N1CC[C@H](Cc2ccccc2)C1=O] | Co. No. 6 |
| 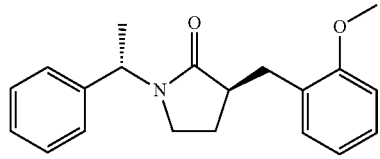 [SMILES: COc1ccccc1C[C@H]1CCN([C@@H](C)c2ccccc2)C1=O] | Co. No. 7 |

TABLE 1-continued
| | |
|---|---|
| 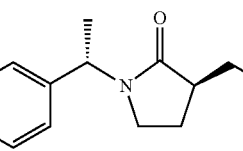 | Co. No. 8 |
| 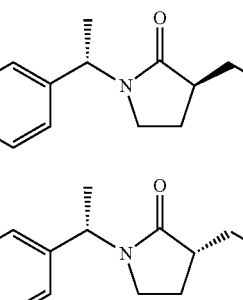 | Co. No. 9 |
| 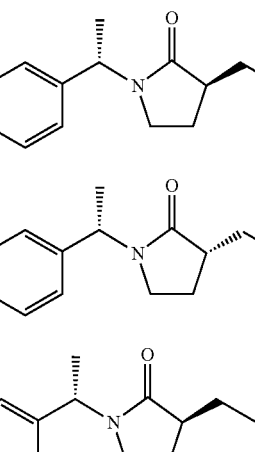 | Co. No. 10 |
| 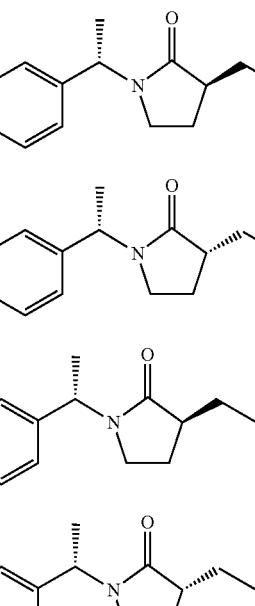 | Co. No. 11 |
| 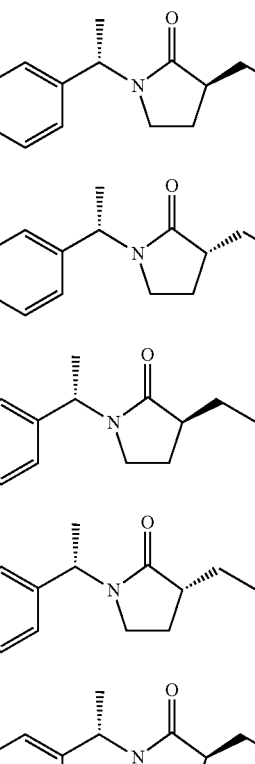 | Co. No. 12 |
| 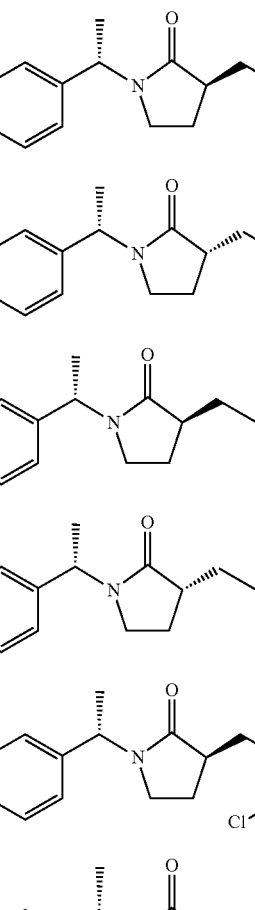 | Co. No. 13 |
| 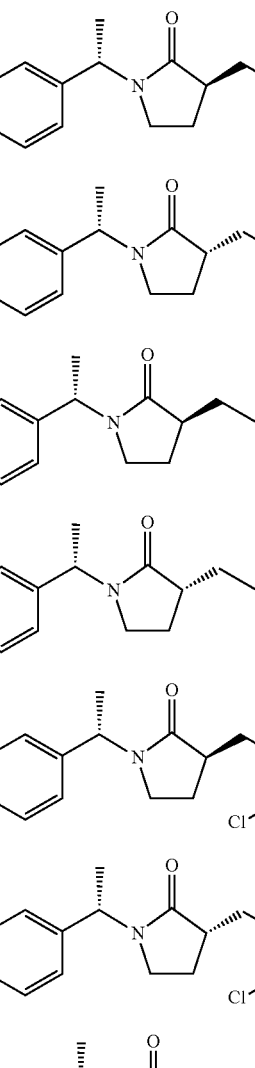 | Co. No. 14 |
| 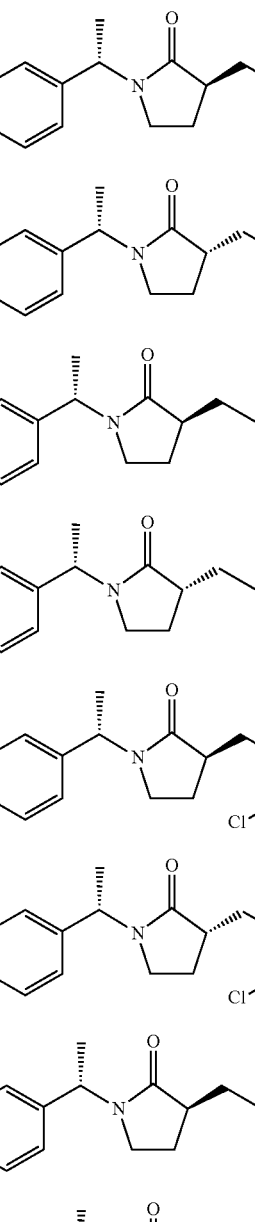 | Co. No. 15 |
| 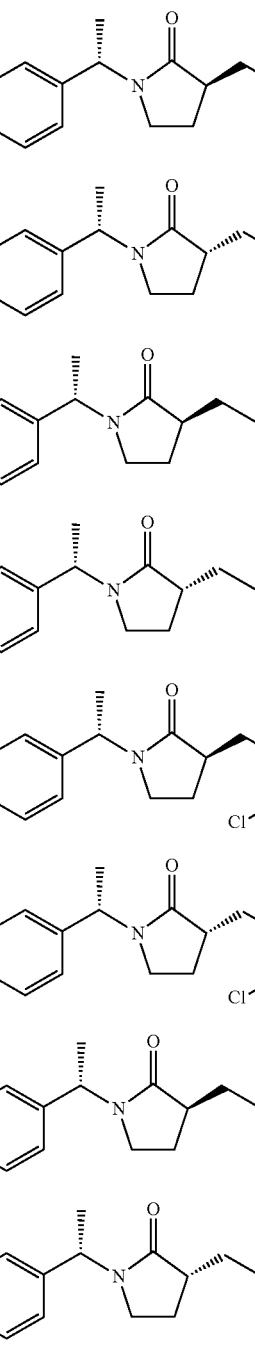 | Co. No. 16 |

TABLE 1-continued
| | |
|---|---|
| 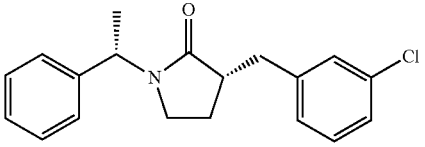 [SMILES: C[C@@H](c1ccccc1)N1CC[C@@H](Cc2cccc(Cl)c2)C1=O] | Co. No. 18 |
| 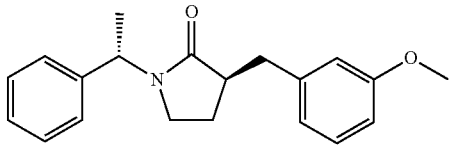 [SMILES: COc1cccc(C[C@H]2CCN([C@@H](C)c3ccccc3)C2=O)c1] | Co. No. 19 |
| 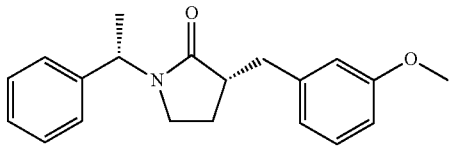 [SMILES: COc1cccc(C[C@@H]2CCN([C@@H](C)c3ccccc3)C2=O)c1] | Co. No. 20 |
| 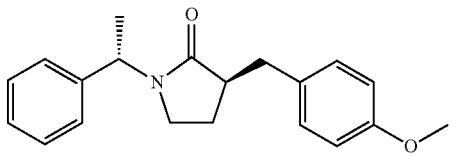 [SMILES: COc1ccc(C[C@H]2CCN([C@@H](C)c3ccccc3)C2=O)cc1] | Co. No. 21 |
| 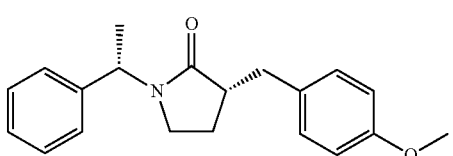 | Co. No. 22 |
| 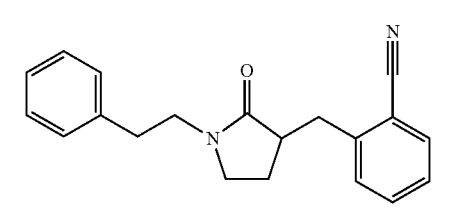 [SMILES: N#Cc1ccccc1CC1CCN(CCc2ccccc2)C1=O] | Co. No. 23 |
| 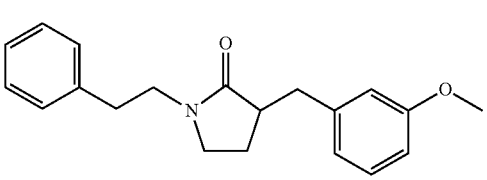 [SMILES: COc1cccc(CC2CCN(CCc3ccccc3)C2=O)c1] | Co. No. 24 |
| 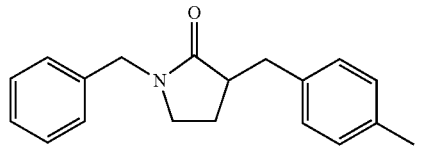 [SMILES: Cc1ccc(CC2CCN(Cc3ccccc3)C2=O)cc1] | Co. No. 25 |
| 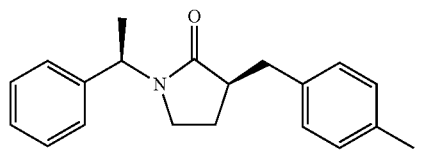 [SMILES: Cc1ccc(C[C@H]2CCN([C@H](C)c3ccccc3)C2=O)cc1] | Co. No. 26 |

TABLE 1-continued
| | |
|---|---|
| 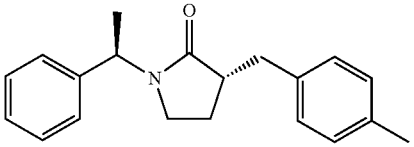 [SMILES: Cc1ccc(C[C@@H]2CCN([C@H](C)c3ccccc3)C2=O)cc1] | Co. No. 27 |
| 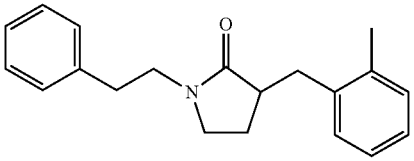 [SMILES: Cc1ccccc1CC1CCN(CCc2ccccc2)C1=O] | Co. No. 28 |
| 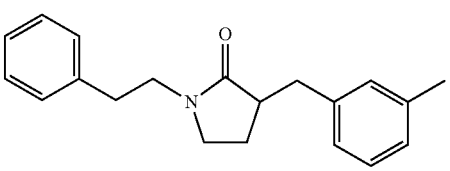 [SMILES: Cc1cccc(CC2CCN(CCc3ccccc3)C2=O)c1] | Co. No. 29 |
| 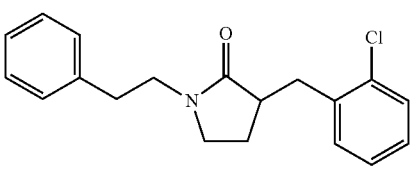 | Co. No. 30 |
| 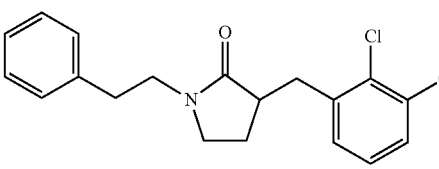 | Co. No. 31 |
| 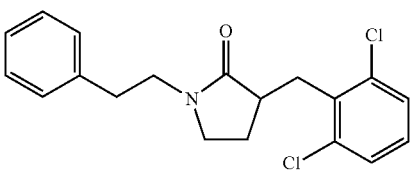 [SMILES: O=C1C(Cc2c(Cl)cccc2Cl)CCN1CCc1ccccc1] | Co. No. 32 |
| 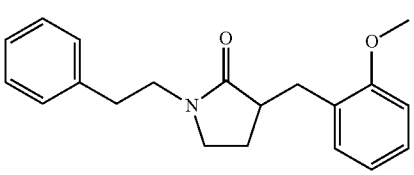 [SMILES: COc1ccccc1CC1CCN(CCc2ccccc2)C1=O] | Co. No. 33 |
| 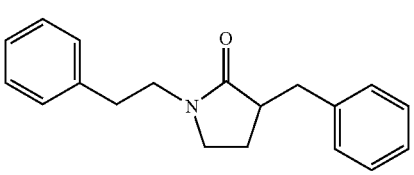 [SMILES: O=C1C(Cc2ccccc2)CCN1CCc1ccccc1] | Co. No. 34 |
| 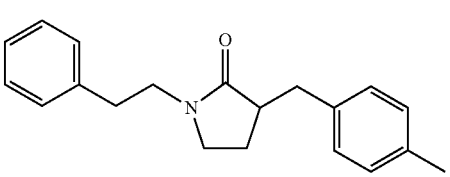 [SMILES: Cc1ccc(CC2CCN(CCc3ccccc3)C2=O)cc1] | Co. No. 35 |

TABLE 1-continued

| Structure | Co. No. |
|---|---|
| (1-phenylethyl)-3-benzyl-pyrrolidin-2-one | Co. No. 36 |
| (1-phenylethyl)-3-benzyl-pyrrolidin-2-one | Co. No. 37 |
| (1-phenylethyl)-3-(2-methoxybenzyl)-pyrrolidin-2-one | Co. No. 38 |
| (1-phenylethyl)-3-(2-methoxybenzyl)-pyrrolidin-2-one | Co. No. 39 |
| (1-phenylethyl)-3-(2-chlorobenzyl)-pyrrolidin-2-one | Co. No. 40 |
| (1-phenylethyl)-3-(2-chlorobenzyl)-pyrrolidin-2-one | Co. No. 41 |
| (1-phenylethyl)-3-(2,3-dichlorobenzyl)-pyrrolidin-2-one | Co. No. 42 |
| (1-phenylethyl)-3-(2,3-dichlorobenzyl)-pyrrolidin-2-one | Co. No. 43 |
| (1-phenylethyl)-3-(2,6-dichlorobenzyl)-pyrrolidin-2-one | Co. No. 44 |
| (1-phenylethyl)-3-(2,6-dichlorobenzyl)-pyrrolidin-2-one | Co. No. 45 |

TABLE 1-continued
| | |
|---|---|
| 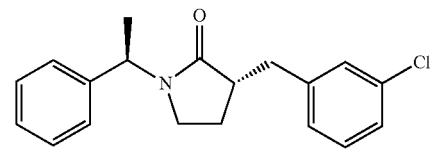 [SMILES: C[C@H](c1ccccc1)N1CC[C@@H](Cc2cccc(Cl)c2)C1=O] | Co. No. 46 |
| 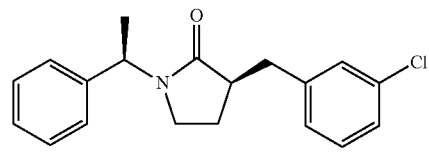 [SMILES: C[C@H](c1ccccc1)N1CC[C@H](Cc2cccc(Cl)c2)C1=O] | Co. No. 47 |
| 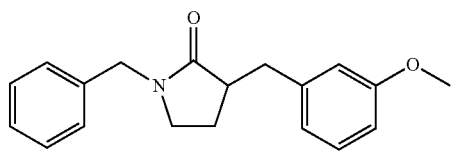 [SMILES: COc1cccc(CC2CCN(Cc3ccccc3)C2=O)c1] | Co. No. 48 |
| 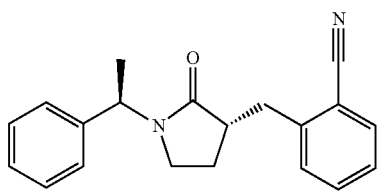 [SMILES: C[C@H](c1ccccc1)N1CC[C@@H](Cc2ccccc2C#N)C1=O] | Co. No. 49 |
| 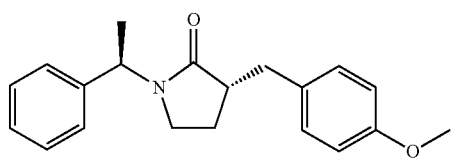 [SMILES: COc1ccc(C[C@@H]2CCN([C@H](C)c3ccccc3)C2=O)cc1] | Co. No. 50 |
| 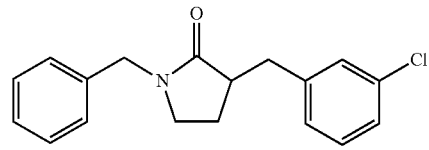 [SMILES: O=C1C(Cc2cccc(Cl)c2)CCN1Cc1ccccc1] | Co. No. 51 |
| 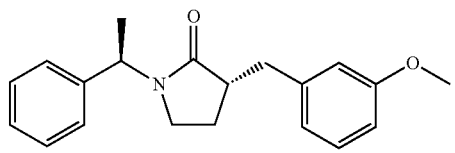 [SMILES: COc1cccc(C[C@@H]2CCN([C@H](C)c3ccccc3)C2=O)c1] | Co. No. 52 |
| 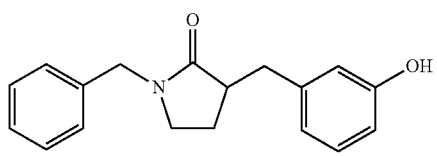 [SMILES: O=C1C(Cc2cccc(O)c2)CCN1Cc1ccccc1] | Co. No. 53 |
| 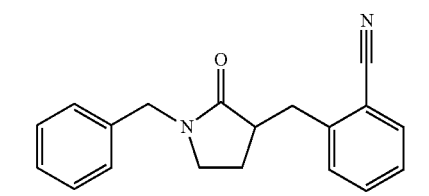 [SMILES: N#Cc1ccccc1CC1CCN(Cc2ccccc2)C1=O] | Co. No. 54 |

TABLE 1-continued
| | |
|---|---|
| 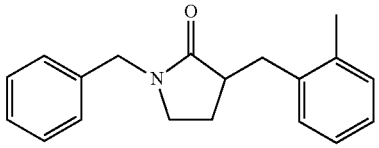 [SMILES: Cc1ccccc1CC1CCN(Cc2ccccc2)C1=O] | Co. No. 55 |
| 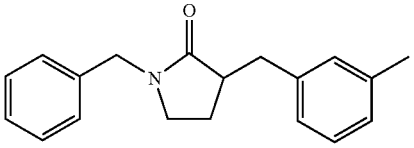 [SMILES: Cc1cccc(CC2CCN(Cc3ccccc3)C2=O)c1] | Co. No. 56 |
| 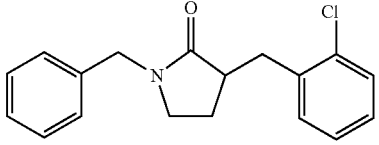 [SMILES: O=C1C(Cc2ccccc2Cl)CCN1Cc1ccccc1] | Co. No. 57 |
| 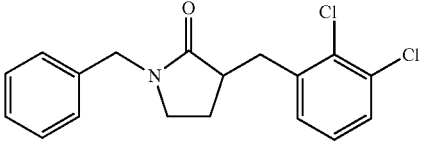 [SMILES: O=C1C(Cc2cccc(Cl)c2Cl)CCN1Cc1ccccc1] | Co. No. 58 |
| 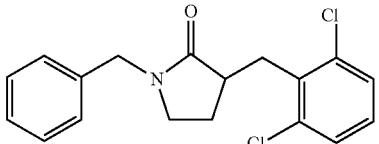 | Co. No. 59 |
| 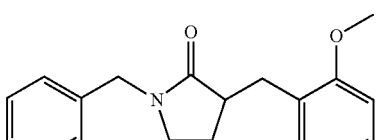 | Co. No. 60 |
| 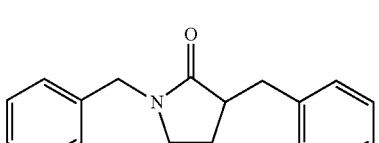 | Co. No. 61 |
| 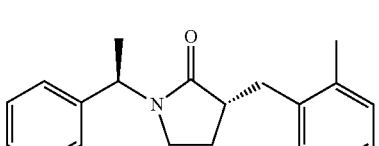 | Co. No. 62 |
| 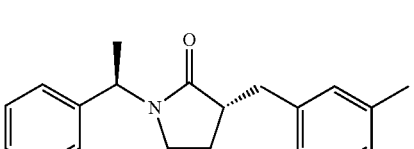 | Co. No. 63 |

TABLE 1-continued

| Structure | Compound |
|---|---|
| | Co. No. 64 |
| | Co. No. 65 |
| | Co. No. 66 |
| | Co. No. 67 |
| | Co. No. 68 |
| | Co. No. 69 |
| | Co. No. 70 |
| | Co. No. 71 |
| | Co. No. 72 |

TABLE 1-continued
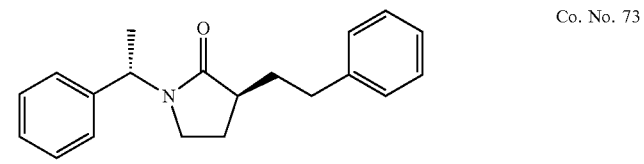 Co. No. 73
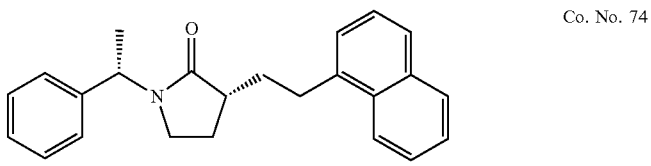 Co. No. 74
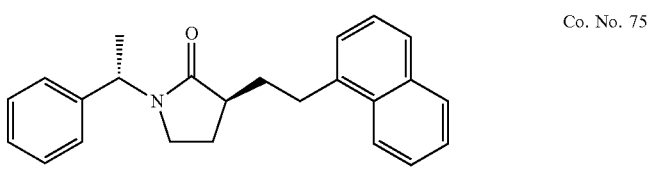 Co. No. 75
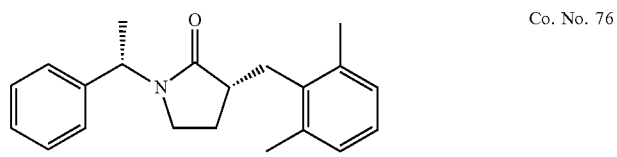 Co. No. 76
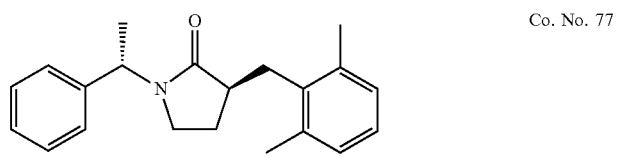 Co. No. 77
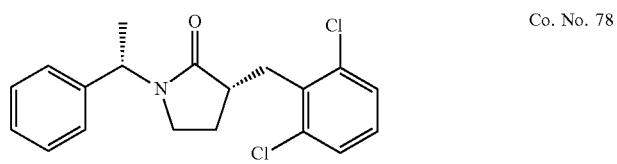 Co. No. 78
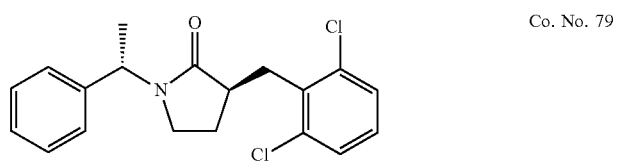 Co. No. 79
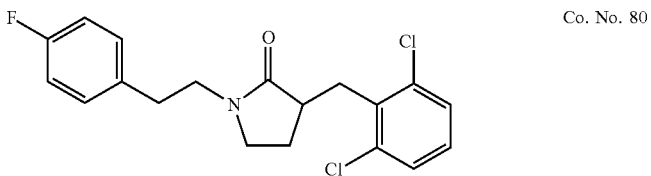 Co. No. 80
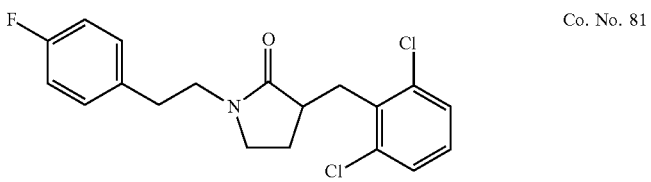 Co. No. 81

TABLE 1-continued
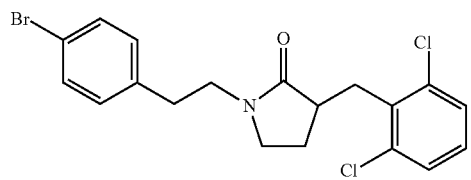 [SMILES: O=C1C(Cc2c(Cl)cccc2Cl)CCN1CCc1ccc(Br)cc1] Co. No. 82
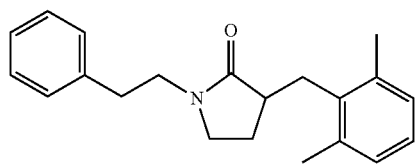 [SMILES: Cc1cccc(C)c1CC1CCN(CCc2ccccc2)C1=O] Co. No. 83
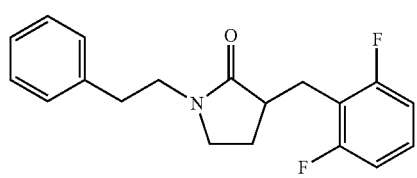 Co. No. 84
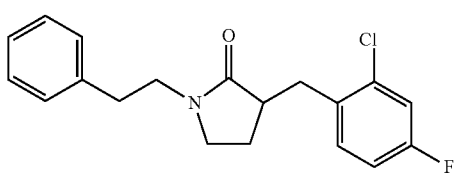 [SMILES: O=C1C(Cc2ccc(F)cc2Cl)CCN1CCc1ccccc1] Co. No. 85
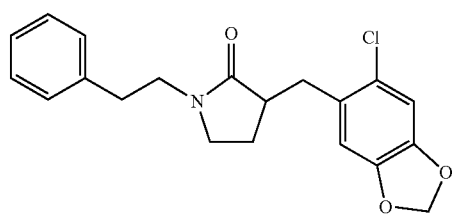 [SMILES: O=C1C(Cc2cc3c(cc2Cl)OCO3)CCN1CCc1ccccc1] Co. No. 86
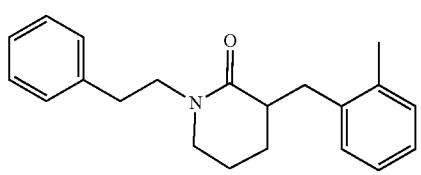 [SMILES: Cc1ccccc1CC1CCCN(CCc2ccccc2)C1=O] Co. No. 87
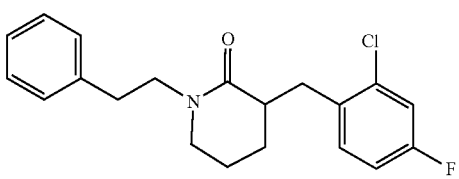 [SMILES: O=C1C(Cc2ccc(F)cc2Cl)CCCN1CCc1ccccc1] Co. No. 88
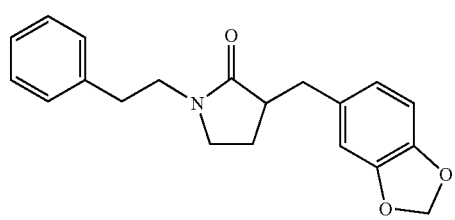 [SMILES: O=C1C(Cc2ccc3c(c2)OCO3)CCN1CCc1ccccc1] Co. No. 89

TABLE 1-continued
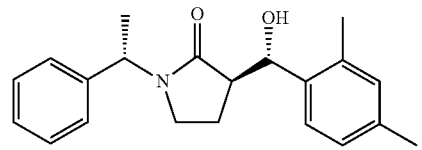 [SMILES: Cc1ccc([C@@H](O)[C@H]2CCN([C@@H](C)c3ccccc3)C2=O)c(C)c1] Co. No. 90
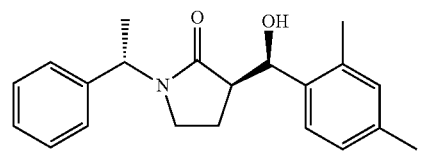 [SMILES: Cc1ccc([C@H](O)[C@H]2CCN([C@@H](C)c3ccccc3)C2=O)c(C)c1] Co. No. 91
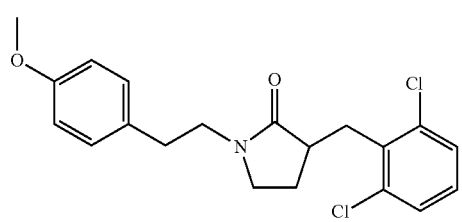 [SMILES: COc1ccc(CCN2CCC(Cc3c(Cl)cccc3Cl)C2=O)cc1] Co. No. 92
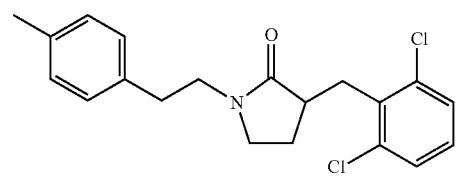 [SMILES: Cc1ccc(CCN2CCC(Cc3c(Cl)cccc3Cl)C2=O)cc1] Co. No. 93
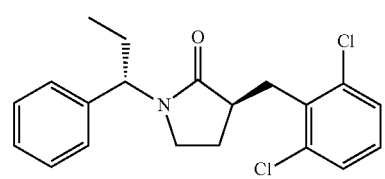 [SMILES: CC[C@@H](c1ccccc1)N1CC[C@H](Cc2c(Cl)cccc2Cl)C1=O] Co. No. 94
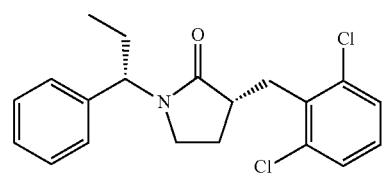 [SMILES: CC[C@@H](c1ccccc1)N1CC[C@@H](Cc2c(Cl)cccc2Cl)C1=O] Co. No. 95
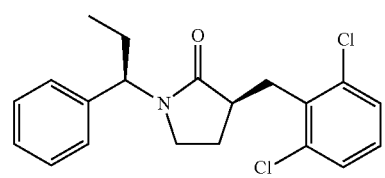 [SMILES: CC[C@H](c1ccccc1)N1CC[C@H](Cc2c(Cl)cccc2Cl)C1=O] Co. No. 96
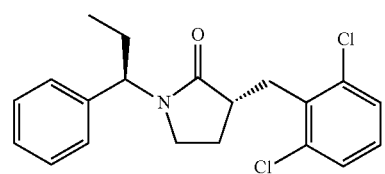 [SMILES: CC[C@H](c1ccccc1)N1CC[C@@H](Cc2c(Cl)cccc2Cl)C1=O] Co. No. 97

TABLE 1-continued
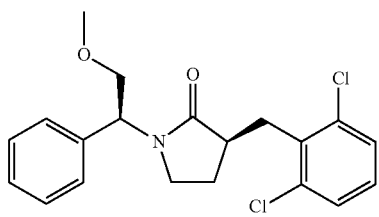 [SMILES: COC[C@H](c1ccccc1)N1CC[C@H](Cc2c(Cl)cccc2Cl)C1=O] Co. No. 98
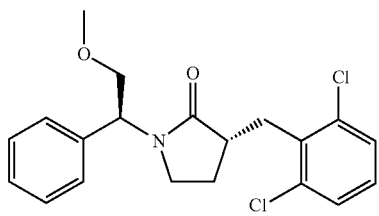 [SMILES: COC[C@H](c1ccccc1)N1CC[C@@H](Cc2c(Cl)cccc2Cl)C1=O] Co. No. 99
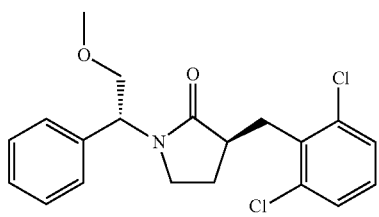 [SMILES: COC[C@@H](c1ccccc1)N1CC[C@H](Cc2c(Cl)cccc2Cl)C1=O] Co. No. 100
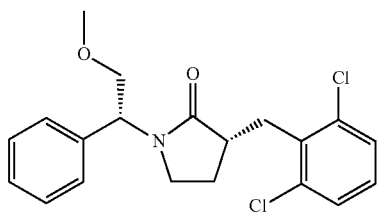 [SMILES: COC[C@@H](c1ccccc1)N1CC[C@@H](Cc2c(Cl)cccc2Cl)C1=O] Co. No. 101
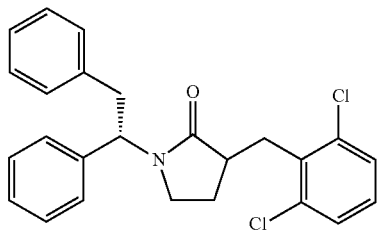 [SMILES: O=C1C(Cc2c(Cl)cccc2Cl)CCN1[C@@H](Cc1ccccc1)c1ccccc1] Co. No. 102
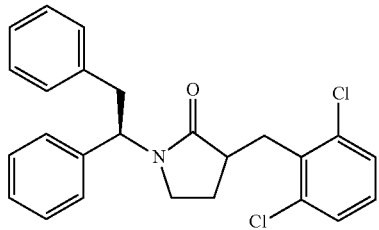 [SMILES: O=C1C(Cc2c(Cl)cccc2Cl)CCN1[C@H](Cc1ccccc1)c1ccccc1] Co. No. 103
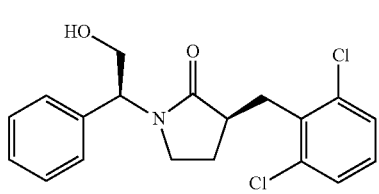 [SMILES: O=C1[C@@H](Cc2c(Cl)cccc2Cl)CCN1[C@H](CO)c1ccccc1] Co. No. 104

TABLE 1-continued
| | |
|---|---|
| 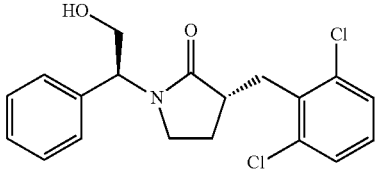 [SMILES: O=C1[C@H](Cc2c(Cl)cccc2Cl)CCN1[C@H](CO)c1ccccc1] | Co. No. 105 |
| 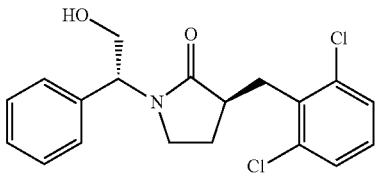 [SMILES: O=C1[C@@H](Cc2c(Cl)cccc2Cl)CCN1[C@@H](CO)c1ccccc1] | Co. No. 106 |
| 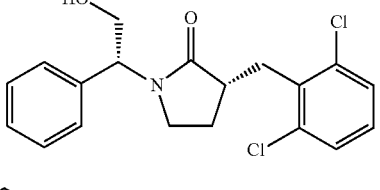 | Co. No. 107 |
| 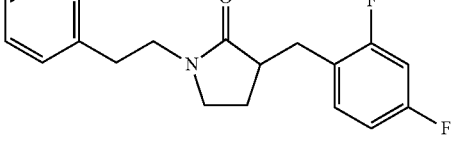 | Co. No. 108 |
| 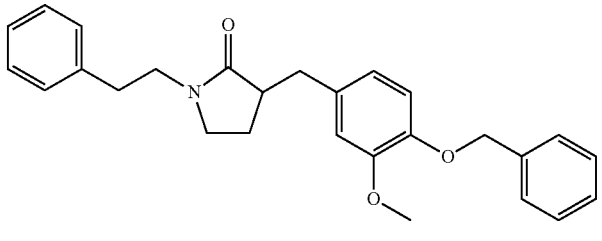 [SMILES: COc1cc(CC2CCN(CCc3ccccc3)C2=O)ccc1OCc1ccccc1] | Co. No. 109 |
| 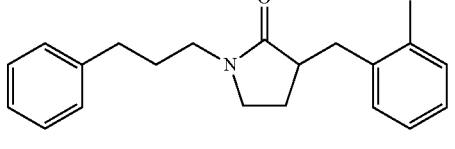 | Co. No. 110 |
| 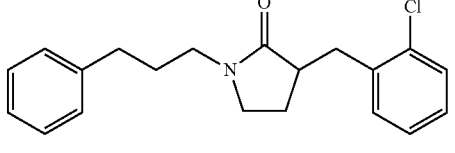 | Co. No. 111 |
| 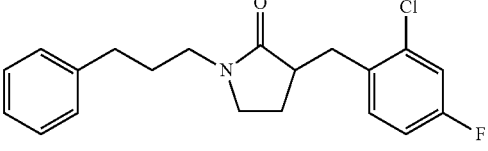 | Co. No. 112 |
| 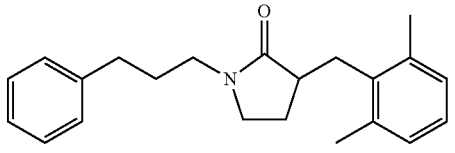 [SMILES: Cc1cccc(C)c1CC1CCN(CCCc2ccccc2)C1=O] | Co. No. 113 |

TABLE 1-continued
| | |
|---|---|
| 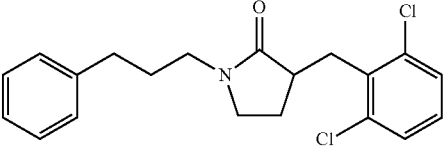 [SMILES: O=C1C(Cc2c(Cl)cccc2Cl)CCN1CCCc1ccccc1] | Co. No. 114 |
| 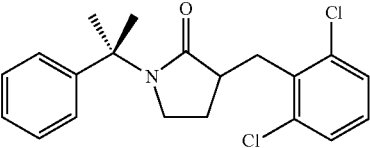 | Co. No. 115 |
| 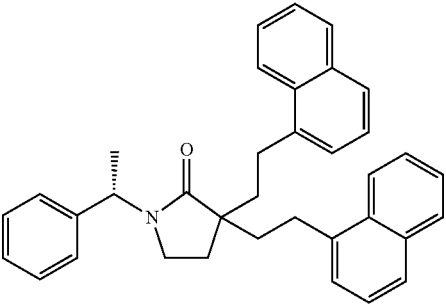 [SMILES: C[C@@H](c1ccccc1)N1CCC(CCc2cccc3ccccc23)(CCc2cccc3ccccc23)C1=O] | Co. No. 116 |
| 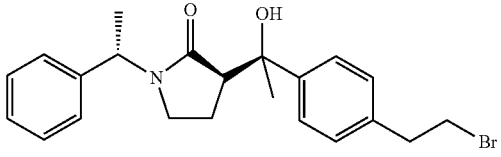 [SMILES: C[C@@H](c1ccccc1)N1CC[C@H]([C@@](C)(O)c2ccc(CCBr)cc2)C1=O] | Co. No. 117 |
| 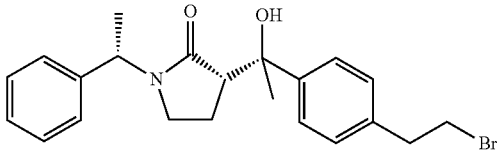 [SMILES: C[C@@H](c1ccccc1)N1CC[C@@H]([C@](C)(O)c2ccc(CCBr)cc2)C1=O] | Co. No. 118 |
| 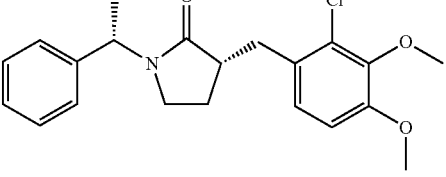 | Co. No. 119 |
| 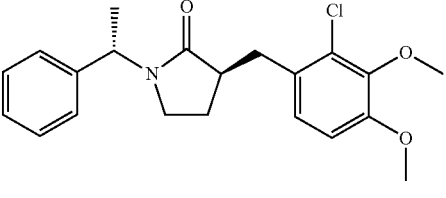 [SMILES: COc1ccc(C[C@H]2CCN([C@@H](C)c3ccccc3)C2=O)c(Cl)c1OC] | Co. No. 120 |
| 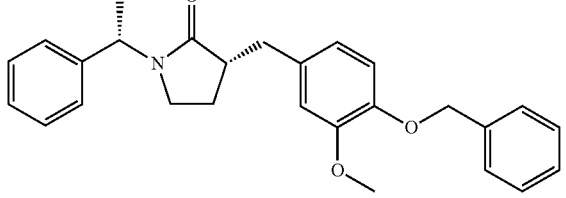 | Co. No. 121 |

TABLE 1-continued
| | |
|---|---|
| 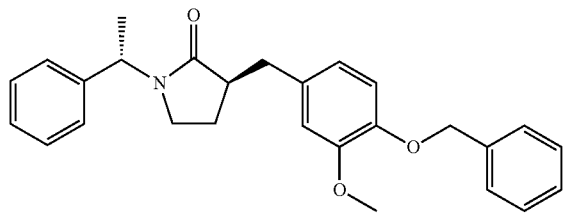 [SMILES: COc1cc(C[C@H]2CCN([C@@H](C)c3ccccc3)C2=O)ccc1OCc1ccccc1] | Co. No. 122 |
| 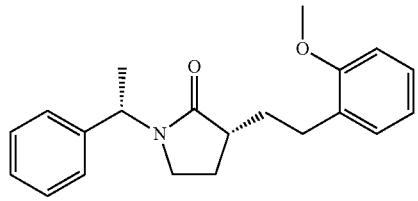 [SMILES: COc1ccccc1CC[C@@H]1CCN([C@@H](C)c2ccccc2)C1=O] | Co. No. 123 |
| 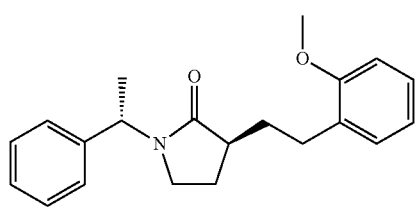 [SMILES: COc1ccccc1CC[C@H]1CCN([C@@H](C)c2ccccc2)C1=O] | Co. No. 124 |
| 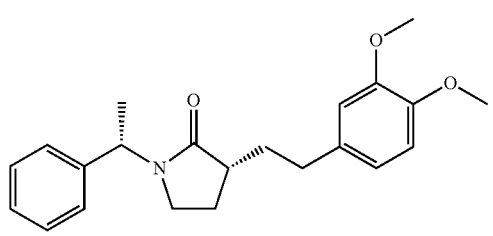 [SMILES: COc1ccc(CC[C@@H]2CCN([C@@H](C)c3ccccc3)C2=O)cc1OC] | Co. No. 125 |
| 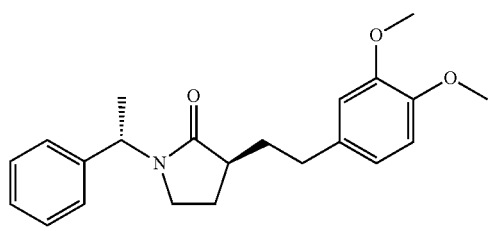 [SMILES: COc1ccc(CC[C@H]2CCN([C@@H](C)c3ccccc3)C2=O)cc1OC] | Co. No. 126 |
| 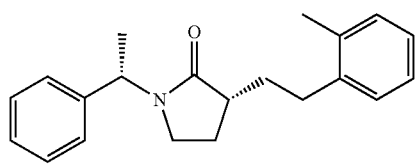 [SMILES: Cc1ccccc1CC[C@@H]1CCN([C@@H](C)c2ccccc2)C1=O] | Co. No. 127 |
| 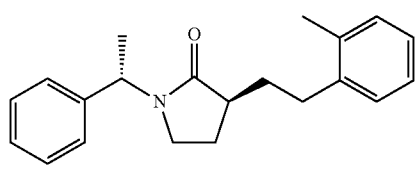 [SMILES: Cc1ccccc1CC[C@H]1CCN([C@@H](C)c2ccccc2)C1=O] | Co. No. 128 |
| 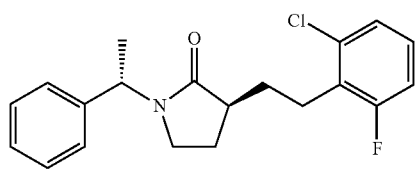 [SMILES: C[C@@H](c1ccccc1)N1CC[C@H](CCc2c(F)cccc2Cl)C1=O] | Co. No. 129 |

TABLE 1-continued
| | |
|---|---|
| 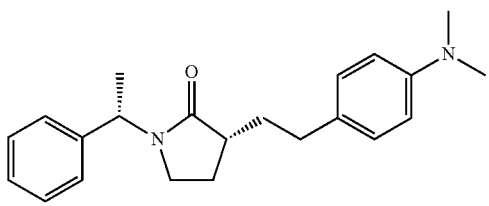 [SMILES: C[C@@H](c1ccccc1)N1CC[C@@H](CCc2ccc(N(C)C)cc2)C1=O] | Co. No. 130 |
| 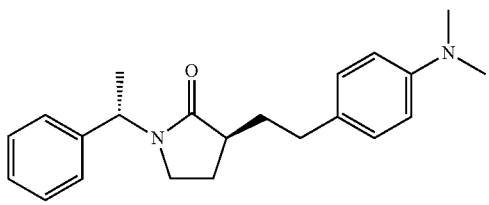 [SMILES: C[C@@H](c1ccccc1)N1CC[C@H](CCc2ccc(N(C)C)cc2)C1=O] | Co. No. 131 |
| 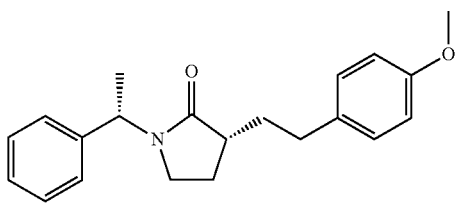 [SMILES: COc1ccc(CC[C@@H]2CCN([C@@H](C)c3ccccc3)C2=O)cc1] | Co. No. 132 |
| 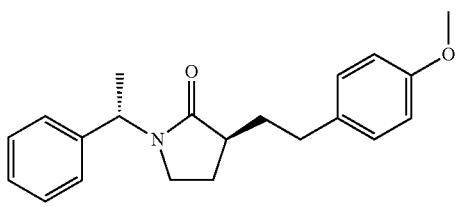 [SMILES: COc1ccc(CC[C@H]2CCN([C@@H](C)c3ccccc3)C2=O)cc1] | Co. No. 133 |
| 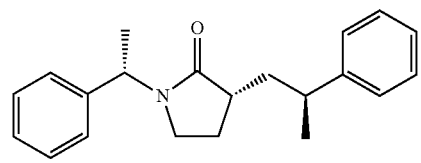 [SMILES: C[C@@H](C[C@@H]1CCN([C@@H](C)c2ccccc2)C1=O)c1ccccc1] | Co. No. 134 |
| 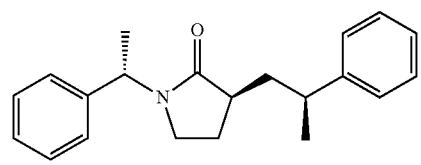 [SMILES: C[C@@H](C[C@H]1CCN([C@@H](C)c2ccccc2)C1=O)c1ccccc1] | Co. No. 135 |
| 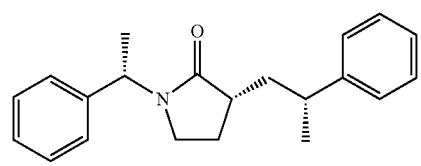 [SMILES: C[C@H](C[C@@H]1CCN([C@@H](C)c2ccccc2)C1=O)c1ccccc1] | Co. No. 136 |
| 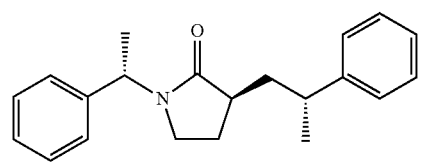 [SMILES: C[C@H](C[C@H]1CCN([C@@H](C)c2ccccc2)C1=O)c1ccccc1] | Co. No. 137 |

TABLE 1-continued
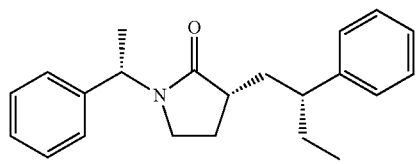 [SMILES: CC[C@H](C[C@@H]1CCN([C@@H](C)c2ccccc2)C1=O)c1ccccc1] Co. No. 138
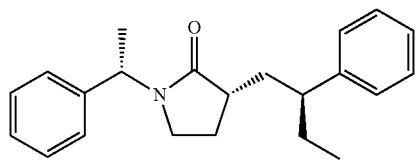 [SMILES: CC[C@@H](C[C@@H]1CCN([C@@H](C)c2ccccc2)C1=O)c1ccccc1] Co. No. 139
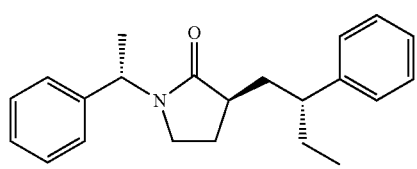 [SMILES: CC[C@H](C[C@H]1CCN([C@@H](C)c2ccccc2)C1=O)c1ccccc1] Co. No. 140
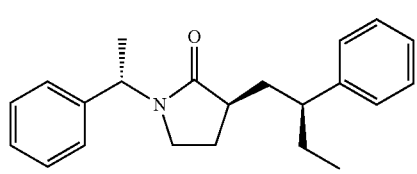 [SMILES: CC[C@@H](C[C@H]1CCN([C@@H](C)c2ccccc2)C1=O)c1ccccc1] Co. No. 141
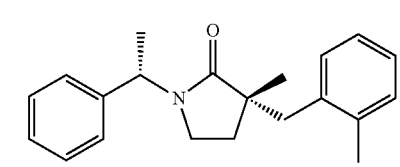 [SMILES: Cc1ccccc1C[C@]1(C)CCN([C@@H](C)c2ccccc2)C1=O] Co. No. 142
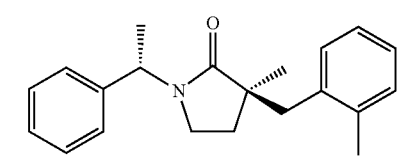 [SMILES: Cc1ccccc1C[C@@]1(C)CCN([C@@H](C)c2ccccc2)C1=O] Co. No. 143
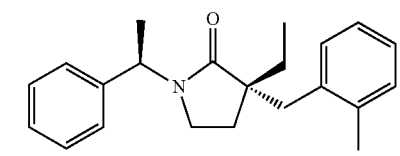 [SMILES: CC[C@@]1(Cc2ccccc2C)CCN([C@H](C)c2ccccc2)C1=O] Co. No. 144
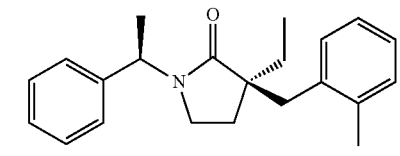 [SMILES: CC[C@]1(Cc2ccccc2C)CCN([C@H](C)c2ccccc2)C1=O] Co. No. 145
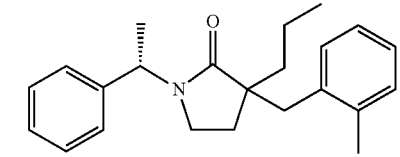 [SMILES: CCCC1(Cc2ccccc2C)CCN([C@@H](C)c2ccccc2)C1=O] Co. No. 146

TABLE 1-continued
| | |
|---|---|
| 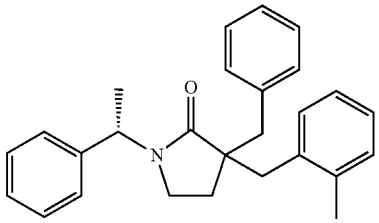 [SMILES: Cc1ccccc1CC1(Cc2ccccc2)CCN([C@@H](C)c2ccccc2)C1=O] | Co. No. 147 |
| 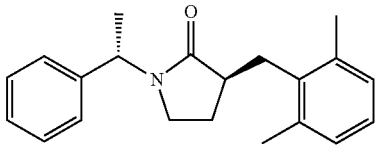 [SMILES: Cc1cccc(C)c1C[C@H]1CCN([C@@H](C)c2ccccc2)C1=O] | Co. No. 148 |
| 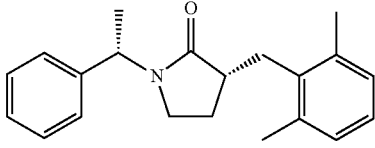 [SMILES: Cc1cccc(C)c1C[C@@H]1CCN([C@@H](C)c2ccccc2)C1=O] | Co. No. 149 |
| 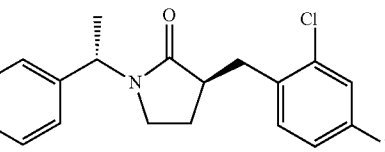 | Co. No. 150 |
| 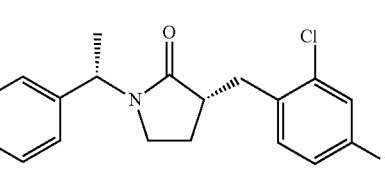 | Co. No. 151 |
| 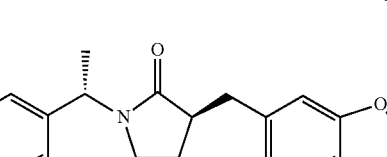 | Co. No. 152 |
| 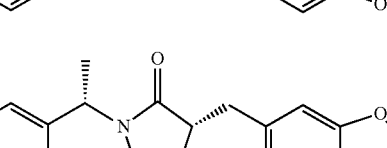 | Co. No. 153 |
| 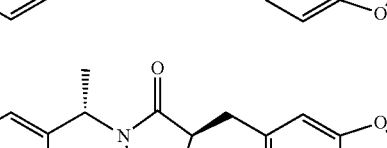 | Co. No. 154 |
| 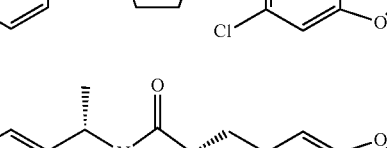 | Co. No. 155 |

TABLE 1-continued
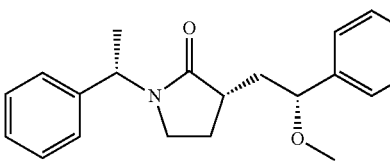 Co. No. 156
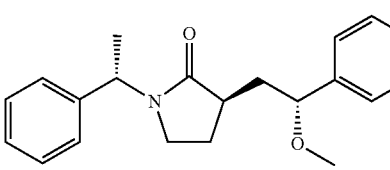 Co. No. 157
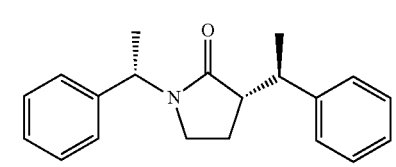 [SMILES: C[C@@H](c1ccccc1)[C@@H]1CCN([C@@H](C)c2ccccc2)C1=O] Co. No. 158
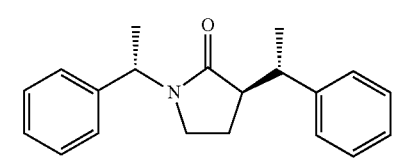 [SMILES: C[C@H](c1ccccc1)[C@H]1CCN([C@@H](C)c2ccccc2)C1=O] Co. No. 159
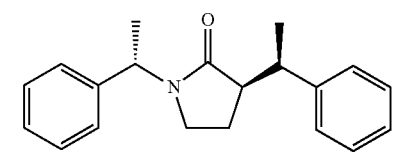 [SMILES: C[C@@H](c1ccccc1)[C@H]1CCN([C@@H](C)c2ccccc2)C1=O] Co. No. 160
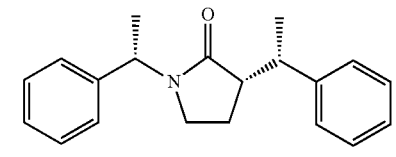 [SMILES: C[C@H](c1ccccc1)[C@@H]1CCN([C@@H](C)c2ccccc2)C1=O] Co. No. 161
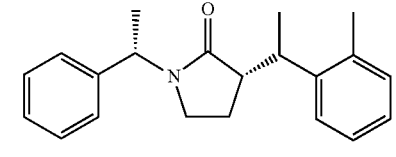 [SMILES: Cc1ccccc1C(C)[C@@H]1CCN([C@@H](C)c2ccccc2)C1=O] Co. No. 162
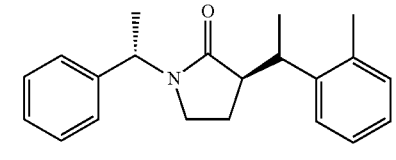 [SMILES: Cc1ccccc1C(C)[C@H]1CCN([C@@H](C)c2ccccc2)C1=O] Co. No. 163
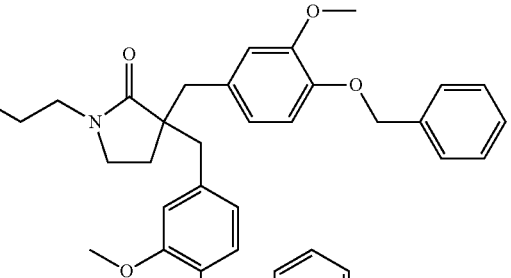 Co. No. 164

TABLE 1-continued

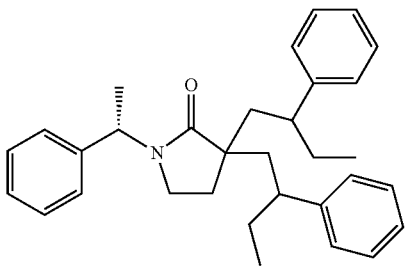 [SMILES: CCC(CC1(CC(CC)c2ccccc2)CCN([C@@H](C)c2ccccc2)C1=O)c1ccccc1]

Co. No. 165

Example B3

Preparation of Compound 166

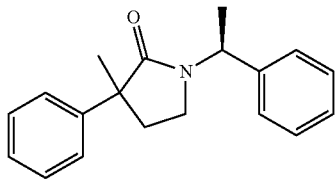

compound 166

A mixture of intermediate 7 (0.00033 mol) in thionyl chloride (2 ml) was stirred and refluxed for 2 hours, then stirred and refluxed over the weekend at room temperature. The solvent was evaporated and the residue was dissolved in dichloromethane, washed with water and filtered through Extrelut, then evaporated. The residue was purified by flash column chromatography on Triconex flash tubes (eluent: $CH_2Cl_2$/EtOAc 95/5). The product fractions were collected and the solvent was evaporated, yielding 0.0588 g (62.5%) of compound 166.

In a Similar Way was Prepared Compound 167

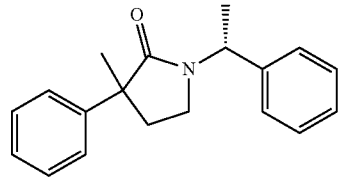

compound 167

| Co. No. | NMR data | melting point (° C.) |
|---|---|---|
| 1 | $CDCl_3$; 1.52 (d, $CH_3$); 1.45-1.67 (m, $H^A$-$CH_2$); 1.91-2.09 (m, $H^B$-$CH_2$); 2.33 (s, $CH_3$); 2.47-2.60 (m, $H^A$-$CH_2$); 2.68-2.83 (m, CH); 2.83-2.97 (dt, $H^A$-$CH_2$); 3.10-3.25 (m, $H^B$-$CH_2$); 3.32-3.43 (dd, $H^B$-$CH_2$); 5.52 (q, CH); 7.03-7.18 (m, 4H-aromatic); 7.20-7.39 (m, 5H-aromatic) | |
| 2 | $CDCl_3$; 1.41 (d, $CH_3$); 1.46-1.62 (m, $H^A$-$CH_2$); 1.72-1.89 (m, $H^B$-$CH_2$); 2.23 (s, $CH_3$); 2.40-2.62 (m, CH, $H^A$-$CH_2$); 2.62-2.75 (m, $H^A$-$CH_2$); 3.00-3.12 (dt, $H^B$-$CH_2$); 3.19-3.30 (dd, $H^B$-$CH_2$); 5.43 (q, CH); 6.93-7.07 (m, 4H-aromatic); 7.08-7.25 (m, 5H-aromatic) | |
| 3 | $CDCl_3$; 1.38 (d, $CH_3$); 1.51-1.69 (m, $H^A$-$CH_2$); 1.79-1.95 (m, $H^B$-$CH_2$); 2.25 (s, $CH_3$); 2.53-2.78 (m, CH, 2x $H^A$-$CH_2$); 2.90-3.03 (dt, $H^B$-$CH_2$); 3.04-3.19 (m, $H^B$-$CH_2$); 5.44 (q, CH); 7.03 (s, 4H-aromatic); 7.12-7.30 (m, 5H-aromatic) | |
| 4 | $CDCl_3$; 1.53 (d, $CH_3$); 1.51-1.70 (m, $H^A$-$CH_2$); 1.92-2.08 (m, $H^B$-$CH_2$); 2.33 (s, $CH_3$); 2.61-2.88 (m, CH, 2x $H^A$-$CH_2$); 3.11-3.27 (m, 2x $H^B$-$CH_2$); 5.52 (q, CH); 7.09 (s, 4H-aromatic); 7.18-7.38 (m, 5H-aromatic) | |
| 5 | $CDCl_3$; 1.45 (d, $CH_3$); 1.59-1.80 (m, $H^A$-$CH_2$); 1.82-2.02 (m, $H^B$-$CH_2$); 2.62-2.88 (m, CH, 2x $H^A$-$CH_2$); 2.91-3.10 (m, $H^B$-$CH_2$); 3.13-3.31 (m, $H^B$-$CH_2$); 5.52 (q, CH); 7.09-7.42 (m, 10H-aromatic) | |
| 6 | $CDCl_3$; 1.50 (d, $CH_3$); 1.48-1.67 (m, $H^A$-$CH_2$); 1.88-2.04 (m, $H^B$-$CH_2$); 2.60-2.87 (m, CH, 2x $H^A$-$CH_2$); 3.08-3.28 (m, 2x $H^B$-$CH_2$); 5.49 (q, CH); 7.10-7.36 (m, 10H-aromatic) | |
| 7 | $CDCl_3$; 1.50 (d, $CH_3$); 1.50-1.65 (m, $H^A$-$CH_2$); 1.82-1.98 (m, $H^B$-$CH_2$); 2.50-2.63 (m, $H^A$-$CH_2$); 2.75-2.92 (m, CH, $H^A$-$CH_2$); 3.07-3.20 (m, $H^B$-$CH_2$); 3.30-3.42 (dd, $H^B$-$CH_2$); 3.79 (s, $CH_3$); 5.51 (q, CH); 6.78-6.90 (m, 2H-aromatic); 7.10-7.19 (m, 2H-aromatic); 7.19-7.37 (m, 5H-aromatic) | |
| 8 | $CDCl_3$; 1.42 (d, $CH_3$); 1.51-1.70 (m, $H^A$-$CH_2$); 1.70-1.86 (m, $H^B$-$CH_2$); 2.47-2.61 (m, $H^A$-$CH_2$); 2.63-2.80 (m, CH, $H^A$-$CH_2$); 2.98-3.12 (dt, $H^B$-$CH_2$); 3.20-3.32 (dd, $H^B$-$CH_2$); 3.73 (s, $CH_3$); 5.45 (q, CH); 6.71-6.85 (m, 2H-aromatic); 7.03-7.30 (m, 7H-aromatic) | |
| 9 | $CDCl_3$; 1.51 (d, $CH_3$); 1.58-1.81 (m, $H^A$-$CH_2$); 1.83-2.00 (m, $H^B$-$CH_2$); 2.71-2.90 (m, CH, 2x $H^A$-$CH_2$); 3.10-3.22 (dt, $H^B$-$CH_2$); 3.33-3.49 (m, $H^B$-$CH_2$); 5.53 (q, CH); 7.09-7.38 (m, 9H-aromatic) | |

| Co. No. | NMR data | melting point (° C.) |
|---|---|---|
| 10 | CDCl$_3$; 1.51 (d, CH$_3$); 1.52-1.68 (m, H$^A$-CH$_2$); 1.90-2.07 (m, H$^B$-CH$_2$); 2.70-2.97 (m, CH, 2x H$^A$-CH$_2$); 3.12-3.25 (m, H$^B$-CH$_2$); 3.37-3.49 (dd, H$^B$-CH$_2$); 5.50 (q, CH); 7.09-7.39 (m, 9H-aromatic) | |
| 11 | CDCl$_3$; 1.46 (d, CH$_3$); 1.50-1.73 (m, H$^A$-CH$_2$); 1.78-1.97 (m, H$^B$-CH$_2$); 2.67-2.86 (m, CH, 2x H$^A$-CH$_2$); 3.03-3.18 (dt, H$^B$-CH$_2$); 3.30-3.48 (m, H$^B$-CH$_2$); 5.46 (q, CH); 7.00-7.32 (m, 8H-aromatic) | |
| 12 | CDCl$_3$; 1.51 (d, CH$_3$); 1.50-1.67 (m, H$^A$-CH$_2$); 1.90-2.07 (m, H$^B$-CH$_2$); 2.75-2.96 (m, CH, 2x H$^A$-CH$_2$); 3.10-3.25 (m, H$^B$-CH$_2$); 3.40-3.51 (dd, H$^B$-CH$_2$); 5.50 (q, CH); 7.02-7.37 (m, 8H-aromatic) | |
| 13 | CDCl$_3$; 1.56 (d, CH$_3$); 1.78-1.92 (m, CH$_2$); 2.76-2.88 (m, H$^A$-CH$_2$); 2.88-3.00 (m, CH); 3.01-3.16 (m, H$^A$-CH$_2$); 3.28-3.38 (m, H$^B$-CH$_2$); 3.43-3.57 (dd, H$^B$-CH$_2$); 5.53 (q, CH); 7.01-7.12 (m, 1H-aromatic); 7.18-7.38 (m, 7H-aromatic) | |
| 14 | CDCl$_3$; 1.52 (d, CH$_3$); 1.68-1.88 (m, H$^A$-CH$_2$); 1.83-1.99 (m, H$^B$-CH$_2$); 2.88-3.08 (m, CH, 2x H$^A$-CH$_2$); 3.08-3.24 (m, H$^B$-CH$_2$); 3.48-3.60 (dd, H$^B$-CH$_2$); 5.51 (q, CH); 7.02-7.13 (m, 1H-aromatic); 7.22-7.42 (m, 7H-aromatic) | |
| 15 | CDCl$_3$; 1.46 (d, CH$_3$); 1.60-1.77 (m, H$^A$-CH$_2$); 1.87-2.02 (m, H$^B$-CH$_2$); 2.32 (s, CH$_3$); 2.61-2.83 (m, CH, 2x H$^A$-CH$_2$); 2.97-3.09 (dt, H$^B$-CH$_2$); 3.11-3.27 (m, H$^B$-CH$_2$); 5.52 (q, CH); 6.95-7.07 (m, 3H-aromatic); 7.11-7.37 (m, 6H-aromatic) | |
| 16 | CDCl$_3$; 1.51 (d, CH$_3$); 1.51-1.63 (m, H$^A$-CH$_2$); 1.90-2.07 (m, H$^B$-CH$_2$); 2.31 (s, CH$_3$); 2.58-2.70 (m, H$^A$-CH$_2$); 2.70-2.89 (m, CH, H$^A$-CH$_2$); 3.09-3.28 (m, 2x H$^B$-CH$_2$); 5.50 (q, CH); 6.93-7.06 (m, 3H-aromatic); 7.09-7.37 (m, 6H-aromatic) | |
| 17 | CDCl$_3$; 1.46 (d, CH$_3$); 1.57-1.73 (m, H$^A$-CH$_2$); 1.88-2.02 (m, H$^B$-CH$_2$); 2.63-2.83 (m, CH, 2x H$^A$-CH$_2$); 2.97-3.09 (dt, H$^B$-CH$_2$); 3.10-3.25 (m, H$^B$-CH$_2$); 5.51 (q, CH); 7.04-7.37 (m, 9H-aromatic) | |
| 18 | CDCl$_3$; 1.50 (d, CH$_3$); 1.46-1.62 (m, H$^A$-CH$_2$); 1.90-2.07 (m, H$^B$-CH$_2$); 2.62-2.87 (m, CH, 2x H$^A$-CH$_2$); 3.09-3.23 (m, 2x H$^B$-CH$_2$); 5.49 (q, CH); 7.00-7.36 (m, 9H-aromatic) | |
| 19 | CDCl$_3$; 1.47 (d, CH$_3$); 1.60-1.78 (m, H$^A$-CH$_2$); 1.87-2.03 (m, H$^B$-CH$_2$); 2.61-2.87 (m, CH, 2x H$^A$-CH$_2$); 3.00-3.13 (dt, H$^B$-CH$_2$); 3.16-3.27 (m, H$^B$-CH$_2$); 3.79 (s, CH$_3$); 5.51 (q, CH); 7.71-7.85 (m, 3H-aromatic); 7.16-7.85 (m, 6H-aromatic) | |
| 20 | CDCl$_3$; 1.51 (d, CH$_3$); 1.51-1.69 (m, H$^A$-CH$_2$); 1.92-2.07 (m, H$^B$-CH$_2$); 2.58-2.90 (m, CH, 2x H$^A$-CH$_2$); 3.10-3.28 (m, 2x H$^B$-CH$_2$); 3.77 (s, CH$_3$); 5.50 (q, CH); 6.70-6.80 (m, 3H-aromatic); 7.11-7.37 (m, 6H-aromatic) | |
| 21 | CDCl$_3$; 1.44 (d, CH$_3$); 1.60-1.77 (m, H$^A$-CH$_2$); 1.87-2.01 (m, H$^B$-CH$_2$); 2.61-2.82 (m, CH, 2x H$^A$-CH$_2$); 2.96-3.08 (dt, H$^B$-CH$_2$); 3.08-3.19 (m, H$^B$-CH$_2$); 3.77 (s, CH$_3$); 5.50 (q, CH); 6.78-6.86 (m, 2H-aromatic); 7.08-7.18 (m, 2H-aromatic); 7.20-7.37 (m, 5H-aromatic) | |
| 22 | CDCl$_3$; 1.49 (d, CH$_3$); 1.50-1.68 (m, H$^A$-CH$_2$); 1.89-2.05 (m, H$^B$-CH$_2$); 2.60-2.82 (m, CH, 2x H$^A$-CH$_2$); 3.05-3.21 (m, 2x H$^B$-CH$_2$); 3.76 (s, CH$_3$); 5.48 (q, CH); 6.71-6.80 (m, 2H-aromatic); 7.01-7.13 (m, 2H-aromatic); 7.14-7.33 (m, 5H-aromatic) | |
| 23 | CDCl$_3$; 1.60-1.78 (m, H$^A$-CH$_2$); 1.93-2.09 (m, H$^B$-CH$_2$); 2.68-2.88 (m, CH, CH$_2$); 2.90-3.21 (m, 2x H$^A$-CH$_2$, H$^B$-CH$_2$); 3.27-3.38 (dd, H$^B$-CH$_2$); 3.42-3.65 (m, CH$_2$); 7.12-7.67 (m, 9H-aromatic) | |
| 24 | CDCl$_3$; 1.47-1.72 (m, H$^A$-CH$_2$); 1.89-2.04 (m, H$^B$-CH$_2$); 2.50-2.75 (m, CH, H$^A$-CH$_2$); 2.76-2.88 (t, CH$_2$); 2.93-3.12 (m, CH$_2$); 3.12-3.21 (dd, H$^B$-CH$_2$); 3.40-3.63 (m, CH$_2$); 3.79 (s, CH$_3$); 6.71-6.80 (m, 3H-aromatic); 7.12-7.33 (m, 6H-aromatic) | |
| 25 | CDCl$_3$; 1.61-1.79 (m, H$^A$-CH$_2$); 1.93-2.08 (m, H$^B$-CH$_2$); 2.32 (s, CH$_3$); 2.62-2.84 (m, CH, H$^A$-CH$_2$); 2.96-3.25 (m, H$^A$-CH$_2$, 2x H$^B$-CH$_2$); 4.44 (dd, CH$_2$); 7.05-7.34 (m, 9H-aromatic) | |
| 26 | CDCl$_3$; 1.45 (d, CH$_3$); 1.58-1.73 (m, H$^A$-CH$_2$); 1.81-1.99 (m, H$^B$-CH$_2$); 2.31 (s, CH$_3$); 2.61-2.82 (m, CH, 2x H$^A$-CH$_2$); 2.75-3.08 (dt, H$^B$-CH$_2$); 3.09-3.23 (m, H$^B$-CH$_2$); 5.52 (q, CH); 7.02-7.14 (m, 4H-aromatic); 7.18-7.37 (m, 5H-aromatic) | |
| 27 | CDCl$_3$; 1.42 (d, CH$_3$); 1.40-1.60 (m, H$^A$-CH$_2$); 1.81-1.99 (m, H$^B$-CH$_2$); 2.23 (s, CH$_3$); 2.50-2.78 (m, CH, 2x H$^A$-CH$_2$); 3.00-3.18 (m, 2x H$^B$-CH$_2$); 5.41 (q, CH); 6.92-7.07 (m, 4H-aromatic); 7.10-7.32 (m, 5H-aromatic) | |
| 28 | CDCl$_3$; 1.53-1.71 (m, H$^A$-CH$_2$); 1.89-2.05 (m, H$^B$-CH$_2$); 2.23 (s, CH$_3$); 2.41-2.55 (m, H$^A$-CH$_2$); 2.59-2.75 (m, CH); 2.80-2.90 (t, CH$_2$); 3.03-3.20 (m, CH$_2$); 3.23-3.35 (dd, H$^B$-CH$_2$); 3.44-3.68 (m, CH2); 7.07-7.34 (m, 9H-aromatic) | |
| 29 | CDCl$_3$; 1.57-1.73 (m, H$^A$-CH$_2$); 1.89-2.04 (m, H$^B$-CH$_2$); 2.32 (s, CH$_3$); 2.50-2.75 (m, CH, H$^A$-CH$_2$); 2.76-2.88 (t, CH$_2$); 2.91-3.21 (m, CH$_2$, H$^B$-CH$_2$); 3.41-3.65 (m, CH$_2$); 6.94-7.08 (m, 3H-aromatic); 7.12-7.33 (m, 6H-aromatic) | |

| Co. No. | NMR data | melting point (° C.) |
|---|---|---|
| 30 | CDCl₃; 1.60-1.76 (m, H$^A$-CH₂); 1.88-2.01 (m, H$^B$-CH₂); 2.68-2.90 (m, CH, CH₂, H$^A$-CH₂); 3.00-3.19 (m, CH₂); 3.27-3.42 (m, H$^B$-CH₂); 3.43-3.67 (m, CH2); 7.10-7.37 (m, 9H-aromatic) | |
| 31 | CDCl₃; 1.53-1.72 (m, H$^A$-CH₂); 1.88-2.03 (m, H$^B$-CH₂); 2.69-2.90 (m, CH, CH₂, H$^A$-CH₂); 3.01-3.20 (m, CH₂); 3.31-3.46 (m, H$^B$-CH₂); 3.46-3.67 (m, CH2); 7.07-7.38 (m, 8H-aromatic) | |
| 32 | CDCl₃; 1.72-1.97 (m, CH₂); 2.80-2.91 (t, CH₂); 2.91-3.27 (m, CH, 2x H$^A$-CH₂, H$^B$-CH₂); 3.38-3.48 (dd, H$^B$-CH₂); 3.48-3.68 (m, CH₂); 7.03-7.35 (m, 8H-aromatic) | |
| 33 | CDCl₃; 1.56-1.72 (m, H$^A$-CH₂); 1.80-1.97 (m, H$^B$-CH₂); 2.47-2.60 (m, H$^A$-CH₂); 2.68-2.80 (m, CH); 2.78-2.88 (t, CH₂); 2.99-3.17 (m, CH₂); 3.23-3.35 (dd, H$^B$-CH₂); 3.42-3.64 (m, CH₂); 3.81 (s, CH₃); 6.80-6.92 (m, 2H-aromatic); 7.10-7.35 (m, 7H-aromatic) | |
| 34 | CDCl₃; 1.55-1.71 (m, H$^A$-CH₂); 1.77-2.02 (m, H$^B$-CH₂); 2.53-2.76 (m, CH, H$^A$-CH₂); 2.77-2.85 (t, CH₂); 2.90-3.02 (dt, H$^A$-CH₂); 3.02-3.14 (m, H$^B$-CH₂); 3.14-3.23 (dd, H$^B$-CH₂); 3.40-3.62 (m, CH₂); 7.12-7.33 (m, 10H-aromatic) | |
| 35 | CDCl₃; 1.56-1.72 (m, H$^A$-CH₂); 1.88-2.02 (m, H$^B$-CH₂); 2.32 (s, CH₃); 2.51-2.73 (m, CH, H$^A$-CH₂); 2.76-2.87 (t, CH₂); 2.90-3.18 (m, CH₂, H$^B$-CH₂); 3.40-3.63 (m, CH₂); 7.03-7.33 (m, 9H-aromatic) | |
| 36 | CDCl₃; 1.38 (d, CH₃); 1.52-1.70 (m, H$^A$-CH₂); 1.79-1.96 (m, H$^B$-CH₂); 2.58-2.77 (m, CH, 2x H$^A$-CH₂); 2.90-3.01 (dt, H$^B$-CH₂); 3.07-3.22 (m, H$^B$-CH₂); 5.44 (q, CH); 7.08-7.29 (m, 10H-aromatic) | |
| 37 | CDCl₃; 1.38 (d, CH₃); 1.40-1.58 (m, H$^A$-CH₂); 1.77-1.92 (m, H$^B$-CH₂); 2.50-2.75 (m, CH, 2x H$^A$-CH₂); 2.94-3.18 (m, 2x H$^B$-CH₂); 5.39 (q, CH); 7.01-7.28 (m, 10H-aromatic) | |
| 38 | CDCl₃; 1.42 (d, CH₃); 1.52-1.70 (m, H$^A$-CH₂); 1.70-1.87 (m, H$^B$-CH₂); 2.47-2.61 (m, H$^A$-CH₂); 2.64-2.80 (m, CH, H$^A$-CH₂); 3.00-3.12 (dt, H$^B$-CH₂); 3.20-3.32 (dd, H$^B$-CH₂); 3.74 (s, CH₃); 5.45 (q, CH); 6.72-6.84 (m, 2H-aromatic); 7.03-7.28 (m, 7H-aromatic) | |
| 39 | CDCl₃; 1.44 (d, CH₃); 1.42-1.59 (m, H$^A$-CH₂); 1.77-1.91 (m, H$^B$-CH₂); 2.42-2.54 (m, H$^A$-CH₂); 2.70-2.87 (m, CH, H$^A$-CH₂); 3.00-3.13 (m, H$^B$-CH₂); 3.22-3.35 (dd, H$^B$-CH₂); 3.72 (s, CH₃); 5.44 (q, CH); 6.71-6.82 (m, 2H-aromatic); 7.02-7.30 (m, 7H-aromatic) | |
| 40 | CDCl₃; 1.38 (d, CH₃); 1.49-1.67 (m, H$^A$-CH₂); 1.69-1.87 (m, H$^B$-CH₂); 2.60-2.77 (m, CH, 2x H$^A$-CH₂); 2.97-3.10 (dt, H$^B$-CH₂); 3.23-3.38 (m, H$^B$-CH₂); 5.41 (q, CH); 6.95-7.26 (m, 9H-aromatic) | |
| 41 | CDCl₃; 1.43 (d, CH₃); 1.38-1.59 (m, H$^A$-CH₂); 1.80-1.99 (m, H$^B$-CH₂); 2.62-2.87 (m, CH, 2x H$^A$-CH₂); 3.01-3.15 (m, H$^B$-CH₂); 3.30-3.41 (dd, H$^B$-CH₂); 5.41 (q, CH); 6.95-7.11 (m, 2H-aromatic); 7.12-7.29 (m, 7H-aromatic) | |
| 42 | CDCl₃; 1.48 (d, CH₃); 1.54-1.73 (m, H$^A$-CH₂); 1.79-1.97 (m, H$^B$-CH₂); 2.68-2.87 (m, CH, 2x H$^A$-CH₂); 3.08-3.22 (m, H$^B$-CH₂); 3.35-3.52 (m, H$^B$-CH₂); 5.49 (q, CH); 7.02-7.23 (m, 8H-aromatic) | |
| 43 | CDCl₃; 1.39 (d, CH₃); 1.32-1.53 (m, H$^A$-CH₂); 1.79-1.96 (m, H$^B$-CH₂); 2.60-2.83 (m, CH, 2x H$^A$-CH₂); 3.00-3.13 (m, H$^B$-CH₂); 3.28-3.42 (m, H$^B$-CH₂); 5.38 (q, CH); 6.91-7.27 (m, 8H-aromatic) | |
| 44 | CDCl₃; 1.45 (d, CH₃); 1.67-1.80 (m, CH₂); 2.64-2.78 (m, H$^A$-CH₂); 2.76-2.89 (m, CH); 2.90-3.03 (m, H$^A$-CH₂); 3.13-3.26 (m, H$^B$-CH₂); 3.37-3.47 (dd, H$^B$-CH₂); 5.43 (q, CH); 6.90-7.00 (m, 1H-aromatic); 7.08-7.26 (m, 7H-aromatic) | |
| 45 | CDCl₃; 1.41 (d, CH₃); 1.57-1.73 (m, H$^A$-CH₂); 1.72-1.88 (m, H$^B$-CH₂); 2.78-3.12 (m, CH, 2x H$^A$-CH₂, H$^B$-CH₂); 3.38-3.48 (dd, H$^B$-CH₂); 5.40 (q, CH); 6.90-7.01 (m, 1H-aromatic); 7.10-7.30 (m, 7H-aromatic) | |
| 46 | CDCl₃; 1.39 (d, CH₃); 1.50-1.68 (m, H$^A$-CH₂); 1.80-1.97 (m, H$^B$-CH₂); 2.56-2.78 (m, CH, 2x H$^A$-CH₂); 2.89-3.03 (dt, H$^B$-CH₂); 3.03-3.18 (m, H$^B$-CH₂); 5.43 (q, CH); 6.97-7.30 (m, 9H-aromatic) | |
| 47 | CDCl₃; 1.39 (d, CH₃); 1.33-1.52 (m, H$^A$-CH₂); 1.79-1.95 (m, H$^B$-CH₂); 2.52-2.77 (m, CH, 2x H$^A$-CH₂); 2.97-3.14 (m, 2x H$^B$-CH₂); 5.38 (q, CH); 6.89-7.27 (m, 9H-aromatic) | |
| 48 | CDCl₃; 1.61-1.79 (m, H$^A$-CH₂); 1.93-2.08 (m, H$^B$-CH₂); 2.61-2.87 (m, CH, H$^A$-CH₂); 2.98-3.18 (m, CH₂); 3.19-3.29 (dd, H$^B$-CH₂); 3.78 (s, CH₃); 4.45 (q, CH₂); 6.72-6.83 (m, 3H-aromatic); 7.13-7.37 (m, 6H-aromatic) | |
| 49 | CDCl₃; 1.43 (d, CH₃); 1.58-1.77 (m, H$^A$-CH₂); 1.85-2.00 (m, H$^B$-CH₂); 2.65-2.82 (m, CH, H$^A$-CH₂); 2.90-3.03 (m, H$^A$-CH₂); 3.05-3.18 (dt, H$^B$-CH₂); 3.28-3.40 (dd, H$^B$-CH₂); 5.43 (q, CH); 7.12-7.30 (m, 6H-aromatic); 7.33-7.58 (m, 3H-aromatic) | |
| 50 | CDCl₃; 1.37 (d, CH₃); 1.52-1.68 (m, H$^A$-CH₂); 1.78-1.93 (m, H$^B$-CH₂); 2.55-2.77 (m, CH, 2x H$^A$-CH₂); 2.89-3.12 (m, 2x H$^B$-CH₂); 3.71 (s, CH₃); 5.43 (q, CH); 6.75 (m, 2H-aromatic); 7.05 (m, 2H-aromatic); 7.12-7.29 (m, 5H-aromatic) | |

| Co. No. | NMR data | melting point (° C.) |
|---|---|---|
| 51 | CDCl$_3$; 1.41-1.60 (m, H$^A$-CH$_2$); 1.77-1.94 (m, H$^B$-CH$_2$); 2.51-2.71 (m, CH, H$^A$-CH$_2$); 2.81-3.14 (m, CH$_2$, H$^B$-CH$_2$); 4.31 (q, CH$_2$); 6.90-7.23 (m, 9H-aromatic) | |
| 52 | CDCl$_3$; 1.46 (d, CH$_3$); 1.60-1.78 (m, H$^A$-CH$_2$); 1.88-2.03 (m, H$^B$-CH$_2$); 2.61-2.85 (m, CH, 2x H$^A$-CH$_2$); 3.00-3.13 (dt, H$^B$-CH$_2$); 3.14-3.28 (m, H$^B$-CH$_2$); 3.79 (s, CH$_3$); 5.51 (q, CH); 6.71-6.83 (m, 3H-aromatic); 7.13-7.38 (m, 6H-aromatic) | |
| 53 | CDCl$_3$; 1.60-1.79 (m, H$^A$-CH$_2$); 1.87-2.05 (m, H$^B$-CH$_2$); 2.60-2.89 (m, CH, H$^A$-CH$_2$); 2.89-3.17 (m, CH$_2$, H$^B$-CH$_2$); 4.42 (q, CH$_2$); 6.60-6.90 (m, 3H-aromatic); 7.01-7.36 (m, 6H-aromatic); 8.32 (s, OH) | |
| 54 | CDCl$_3$; 1.63-1.85 (m, H$^A$-CH$_2$); 1.95-2.16 (m, H$^B$-CH$_2$); 2.75-2.96 (m, CH); 2.98-3.23 (m, CH$_2$, H$^A$-CH$_2$); 3.32-3.53 (dd, H$^B$-CH$_2$); 4.46 (s, CH$_2$); 7.07-7.68 (m, 9H-aromatic) | |
| 55 | CDCl$_3$; 1.60-1.77 (m, H$^A$-CH$_2$); 1.95-2.10 (m, H$^B$-CH$_2$); 2.35 (s, CH$_3$); 2.52-2.68 (m, H$^A$-CH$_2$); 2.68-2.77 (m, CH); 3.09-3.19 (m, CH$_2$); 3.36-3.44 (dd, H$^B$-CH$_2$); 4.49 (s, CH$_2$); 7.08-7.20 (m, 4H-aromatic); 7.20-7.38 (m, 5H-aromatic) | |
| 56 | CDCl$_3$; 1.60-1.78 (m, H$^A$-CH$_2$); 1.92-2.07 (m, H$^B$-CH$_2$); 2.32 (m, CH$_3$); 2.61-2.86 (m, CH, H$^A$-CH$_2$); 2.97-3.27 (m, CH$_2$, H$^B$-CH$_2$); 4.44 (q, CH$_2$); 6.95-7.08 (m, 3H-aromatic); 7.11-7.36 (m, 6H-aromatic) | |
| 57 | CDCl$_3$; 1.52-1.70 (m, H$^A$-CH$_2$); 1.79-1.97 (m, H$^B$-CH$_2$); 2.64-2.86 (m, CH, H$^A$-CH$_2$); 2.95-3.07 (m, H$^A$-CH$_2$, H$^B$-CH$_2$); 3.28-3.42 (m, H$^B$-CH$_2$); 4.37 (s, CH$_2$); 6.99-7.30 (m, 9H-aromatic) | |
| 58 | CDCl$_3$; 1.60-1.79 (m, H$^A$-CH$_2$); 1.93-2.09 (m, H$^B$-CH$_2$); 2.79-2.97 (m, CH, H$^A$-CH$_2$); 3.07-3.19 (m, CH$_2$); 3.41-3.56 (m, H$^B$-CH$_2$); 4.47 (s, CH$_2$); 7.07-7.37 (m, 8H-aromatic) | |
| 59 | CDCl$_3$; 1.77-1.88 (m, CH$_2$); 2.81-3.20 (m, 2x CH$_2$, H$^A$-CH$_2$); 3.32-3.50 (m, H$^B$-CH$_2$); 4.40 (q, CH$_2$); 6.95-7.04 (m, 1H-aromatic); 7.12-7.30 (7H-aromatic) | |
| 60 | CDCl$_3$; 1.62-1.79 (m, H$^A$-CH$_2$); 1.86-2.02 (m, H$^B$-CH$_2$); 2.57-2.68 (m, H$^A$-CH$_2$); 2.79-2.94 (m, CH); 3.03-3.13 (m, CH$_2$); 3.32-3.42 (dd, H$^B$-CH$_2$); 3.81 (s, CH$_3$); 4.46 (s, CH$_2$); 6.80-6.92 (m, 2H-aromatic); 7.11-7.37 (m, 7H-aromatic) | |
| 61 | CDCl$_3$; 1.50-1.68 (m, H$^A$-CH$_2$); 1.82-1.97 (m, H$^B$-CH$_2$); 2.56-2.77 (m, CH, H$^A$-CH$_2$); 2.83-3.07 (m, CH$_2$); 3.08-3.22 (m, H$^B$-CH$_2$); 4.34 (q, CH$_2$); 7.03-7.26 (m, 10H-aromatic) | |
| 62 | CDCl$_3$; 1.46 (d, CH$_3$); 1.52-1.69 (m, H$^A$-CH$_2$); 1.80-1.97 (m, H$^B$-CH$_2$); 2.28 (s, CH$_3$); 2.44-2.58 (m, H$^A$-CH$_2$); 2.58-2.69 (m, CH); 2.69-2.82 (m, H$^A$-CH$_2$); 3.08-3.19 (dt, H$^B$-CH$_2$); 3.24-3.35 (dd, H$^B$-CH$_2$); 5.47 (q, CH); 7.00-7.12 (m, 4H-aromatic); 7.14-7.32 (m, 5H-aromatic) | |
| 63 | CDCl$_3$; 1.39 (d, CH$_3$); 1.52-1.70 (m, H$^A$-CH$_2$); 1.79-1.95 (m, H$^B$-CH$_2$); 2.25 (s, CH$_3$); 2.53-2.77 (m, CH, 2x H$^A$-CH$_2$); 2.90-3.01 (dt, H$^B$-CH$_2$); 3.05-3.20 (m, H$^B$-CH$_2$); 5.45 (q, CH); 6.89-6.98 (m, 3H-aromatic); 7.05-7.30 (m, 6H-aromatic) | |
| 64 | CDCl$_3$; 1.44 (d, CH$_3$); 1.45-1.63 (m, H$^A$-CH$_2$); 1.91-2.08 (m, H$^B$-CH$_2$); 2.71-2.87 (m, CH, H$^A$-CH$_2$); 2.90-3.03 (m, H$^A$-CH$_2$); 3.04-3.19 (m, H$^B$-CH$_2$); 3.27-3.39 (dd, H$^B$-CH$_2$); 5.41 (q, CH); 7.10-7.29 (m, 6H-aromatic); 7.31-7.46 (m, 2H-aromatic); 7.49-7.57 (m, 1H-aromatic) | |
| 65 | CDCl$_3$; 1.43 (d, CH$_3$); 1.47-1.62 (m, H$^A$-CH$_2$); 1.83-1.98 (m, H$^B$-CH$_2$); 2.53-2.77 (m, CH, 2x H$^A$-CH$_2$); 3.01-3.15 (m, 2x H$^B$-CH$_2$); 3.71 (s, CH$_3$); 5.41 (q, CH); 6.67-6.75 (m, 2H-aromatic); 6.98-7.07 (m, 2H-aromatic); 7.09-7.28 (m, 5H-aromatic) | |
| 66 | CDCl$_3$; 1.51 (d, CH$_3$); 1.50-1.67 (m, H$^A$-CH$_2$); 1.91-2.07 (m, H$^B$-CH$_2$); 2.58-2.90 (m, CH, 2x H$^A$-CH$_2$); 3.10-3.27 (m, 2x H$^B$-CH$_2$); 3.77 (s, CH$_3$); 5.49 (q, CH); 6.69-6.80 (m, 3H-aromatic); 7.10-7.34 (m, 6H-aromatic) | |
| 67 | CDCl$_3$; 1.53 (d, CH$_3$); 1.49-1.68 (m, H$^A$-CH$_2$); 1.93-2.10 (m, H$^B$-CH$_2$); 2.35 (s, CH$_3$); 2.50-2.62 (m, H$^A$-CH$_2$); 2.70-2.85 (m, CH); 2.87-2.98 (dt, H$^A$-CH$_2$); 3.13-3.27 (m, H$^B$-CH$_2$); 3.34-3.45 (dd, H$^B$-CH$_2$); 5.53 (q, CH); 7.05-7.20 (m, 4H-aromatic); 7.22-7.40 (m, 5H-aromatic) | |
| 68 | CDCl$_3$; 1.44 (d, CH$_3$); 1.53-1.65 (m, H$^A$-CH$_2$); 1.83-1.99 (m, H$^B$-CH$_2$); 2.23 (s, CH$_3$); 2.49-2.81 (m, CH, 2x H$^A$-CH$_2$); 3.03-3.20 (m, 2x H$^B$-CH$_2$); 5.43 (q, CH); 6.88-6.98 (m, 3H-aromatic); 7.02-7.29 (m, 6H-aromatic) | |
| 69 | CDCl$_3$; 1.37-1.58 (m, H$^A$-CH$_2$); 1.56 (d, CH$_3$); 1.61-1.77 (m, H$^B$-CH$_2$); 2.27 (s, CH$_3$); 2.38 (s, CH$_3$); 2.73-2.93 (m, CH, H$^A$-CH$_2$); 3.12-3.27 (dt, H$^B$-CH$_2$); 4.97 (d, CH); 5.51 (q, CH); 6.90-7.04 (m, 2H-aromatic); 7.20-7.38 (m, 6H-aromatic) | |
| 70 | CDCl$_3$; 1.45 (d, CH$_3$); 1.53-1.72 (m, H$^A$-CH$_2$); 1.77-1.91 (m, H$^B$-CH$_2$); 2.58-2.79 (m, CH, 2x H$^A$-CH$_2$); 3.08-3.30 (m, 2x H$^B$-CH$_2$); | 58-60 |

| Co. No. | NMR data | melting point (° C.) |
|---|---|---|
| | 5.45 (q, CH); 6.69-6.82 (m, 2H-aromatic); 7.00-7.29 (m, 6H-aromatic) | |
| 71 | CDCl$_3$; 1.43 (d, CH$_3$); 1.57-1.63 (m, H$^A$-CH$_2$); 1.80-1.97 (m, H$^B$-CH$_2$); 2.52-2.90 (m, CH, 2x H$^A$-CH$_2$); 3.01-3.17 (m, H$^B$-CH$_2$); 3.19-3.28 (m, H$^B$-CH$_2$); 5.42 (q, CH); 6.68-6.82 (m, 2H-aromatic); 6.98-7.13 (m, 1H-aromatic); 7.16-7.32 (m, 5H-aromatic) | |
| 72 | CDCl$_3$; 1.43 (d, CH$_3$); 1.52-1.68 (m, CH$_2$); 1.94-2.09 (m, H$^A$-CH$_2$); 2.09-2.25 (m, CH); 2.25-2.38 (m, H$^B$-CH$_2$); 2.52-2.76 (m, CH$_2$); 2.74-2.81 (m, H$^A$-CH$_2$); 3.10-3.22 (dt, H$^B$-CH$_2$); 5.43 (q, CH); 7.01-7.28 (m, 10H-aromatic) | |
| 73 | CDCl$_3$; 1.42 (d, CH$_3$); 1.40-1.66 (m, CH$_2$); 1.98-2.26 (m, CH, H$^A$-CH$_2$); 2.27-2.44 (m, H$^B$-CH$_2$); 2.49-2.74 (m, CH$_2$); 2.78-2.90 (dt, H$^A$-CH$_2$); 3.04-3.19 (m, H$^B$-CH$_2$); 5.41 (q, CH); 7.02-7.30 (m, 10H-aromatic) | |
| 74 | CDCl$_3$; 1.44 (d, CH$_3$); 1.51-1.70 (m, H$^A$-CH$_2$); 1.70-1.88 (m, H$^B$-CH$_2$); 1.97-2.13 (m, H$^A$-CH$_2$); 2.17-2.32 (m, CH); 2.34-2.50 (m, H$^B$-CH$_2$); 2.70-2.85 (q, H$^A$-CH$_2$); 3.04-3.25 (m, CH$_2$, H$^B$-CH$_2$); 5.45 (q, CH); 7.08-7.31 (m, 7H-aromatic); 7.31-7.48 (m, 2H-aromatic); 7.62 (m, 1H-aromatic); 7.75 (m, 1H-aromatic); 8.02 (m, 1H-aromatic) | |
| 75 | CDCl$_3$; 1.44 (d, CH$_3$); 1.48-1.66 (m, H$^A$-CH$_2$); 1.67-1.83 (m, H$^B$-CH$_2$); 2.02-2.20 (m, H$^A$-CH$_2$); 2.20-2.32 (m, CH); 2.40-2.57 (m, H$^B$-CH$_2$); 2.80-2.93 (dt, H$^A$-CH$_2$); 3.02-3.22 (m, CH$_2$, H$^B$-CH$_2$); 5.43 (q, CH); 7.08-7.31 (m, 7H-aromatic); 7.32-7.49 (m, 2H-aromatic); 7.63 (m, 1H-aromatic); 7.77 (m, 1H-aromatic); 8.01 (m, 1H-aromatic) | |
| 76 | CDCl$_3$; 1.39-1.83 (m, 2x CH$_2$); 1.53 (d, CH$_3$); 2.38 (s, 2x CH$_3$); 2.50-2.67 (m, CH); 2.69-2.88 (m, 2x H$^A$-CH$_2$); 3.05-3.19 (m, H$^B$-CH$_2$); 2.55-2.67 (dd, H$^B$-CH$_2$); 6.18 (q, CH); 7.00 (s, 3H-aromatic); 7.17-7.34 (m, 5H-aromatic) | |
| 77 | CDCl$_3$; 1.51 (d, CH$_3$); 1.38-1.84 (m, 2x CH$_2$); 2.38 (s, 2xCH$_3$); 2.50-2.67 (m, CH); 2.70-2.87 (m, 2x H$^A$-CH$_2$); 3.03-3.16 (m, H$^B$-CH$_2$); 3.51-3.62 (dd, H$^B$-CH$_2$); 6.17 (q, CH); 7.01 (s, 3H-aromatic); 7.22-7.40 (m, 5H-aromatic) | 100-104 |
| 78 | CDCl$_3$; 1.53 (d, CH$_3$); 1.37-1.88 (m, 2x CH$_2$); 2.77-2.99 (m, CH, H$^A$-CH$_2$); 3.06-3.20 (m, H$^A$-CH$_2$, H$^B$-CH$_2$); 3.72-3.85 (dd, H$^B$-CH$_2$); 6.17 (q, CH); 7.01-7.13 (m, 1H-aromatic); 7.18-7.40 (m, 7H-aromatic) | |
| 79 | CDCl$_3$; 1.45 (d, CH$_3$); 1.39-1.79 (m, 2x CH$_2$); 2.63-2.92 (m, CH, H$^A$-CH$_2$); 2.96-3.14 (m, H$^A$-CH$_2$, H$^B$-CH$_2$); 3.62-3.78 (dd, H$^B$-CH$_2$); 6.08 (q, CH); 6.98-7.07 (m, 1H-aromatic); 7.14-7.33 (m, 7H-aromatic) | 121-125 |
| 80 | CDCl$_3$; 1.73-1.97 (m, CH$_2$); 2.78-3.06 (m, CH, CH$_2$, H$^A$-CH$_2$); 3.07-3.28 (m, CH$_2$); 3.37-3.67 (m, CH$_2$, H$^B$-CH$_2$); 6.90-7.32 (m, 7H-aromatic) | |
| 81 | CDCl$_3$; 1.73-1.98 (m, CH$_2$); 2.77-3.27 (m, CH, 2x CH$_2$, H$^A$-CH$_2$); 3.37-3.67 (m, CH$_2$, H$^B$-CH$_2$); 7.02-7.38 (m, 7H-aromatic) | |
| 82 | CDCl$_3$; 1.70-1.99 (m, CH$_2$); 2.73-3.25 (m, CH, 2x CH$_2$, H$^A$-CH$_2$); 3.34-3.63 (m, CH$_2$, H$^B$-CH$_2$); 7.08 (m, 2H-aromatic); 7.27 (m, 2H-aromatic); 7.40 (m, 2H-aromatic) | |
| 83 | CDCl$_3$; 1.48-1.63 (m, H$^A$-CH$_2$); 1.76-1.92 (m, H$^B$-CH$_2$); 2.24 (s, 2x CH$_3$); 2.43-2.60 (m, CH, H$^A$-CH$_2$); 2.78 (t, CH$_2$); 2.95-3.25 (m, CH$_2$, H$^B$-CH$_2$); 3.37-3.61 (m, CH$_2$); 6.92 (s, 3H-aromatic); 7.08-7.27 (m, 5H-aromatic) | |
| 84 | CDCl$_3$; 1.57-1.75 (m, H$^A$-CH$_2$); 1.83-2.00 (m, H$^B$-CH$_2$); 2.55-2.90 (m, CH, CH$_2$, H$^A$-CH$_2$); 3.08-3.29 (m, CH$_2$, H$^B$-CH$_2$); 3.38-3.67 (m, CH$_2$); 6.77-6.91 (m, 2H-aromatic); 7.08-7.34 (m, 6H-aromatic) | |
| 85 | CDCl$_3$; 1.52-1.70 (m, H$^A$-CH$_2$); 1.95-2.01 (m, H$^B$-CH$_2$); 2.63-2.78 (m, CH, H$^A$-CH$_2$); 2.83 (t, CH$_2$); 2.99-3.19 (m, CH$_2$); 3.20-3.34 (m, H$^B$-CH$_2$); 3.41-3.65 (m, CH$_2$); 6.83-6.93 (dt, 1H-aromatic); 7.08 (dd, 1H-aromatic); 7.13-7.32 (m, 6H-aromatic) | 70-71 |
| 86 | CDCl$_3$; 1.48-1.63 (m, H$^A$-CH$_2$); 1.79-1.96 (m, H$^B$-CH$_2$); 2.53-2.67 (m, CH, H$^A$-CH$_2$); 2.70-2.81 (t, CH$_2$); 2.92-3.20 (m, CH$_2$, H$^B$-CH$_2$); 3.34-3.58 (m, CH$_2$); 5.85 (s, CH$_2$); 6.66 (s, 1H-aromatic); 6.73 (s, 1H-aromatic); 7.07-7.25 (m, 5H-aromatic) | |
| 87 | CDCl$_3$; 1.25-1.77 (m, 2x CH$_2$); 2.29 (s, CH$_3$); 2.33-2.50 (m, CH, H$^A$-CH$_2$); 2.81 (dt, CH$_2$); 2.95-3.12 (m, CH$_2$); 3.40-3.57 (m, CH$_2$, H$^B$-CH$_2$); 6.98-7.27 (m, 9H-aromatic) | |
| 88 | CDCl$_3$; 1.22-1.78 (m, 2x CH$_2$); 2.43-2.59 (m, CH); 2.60-2.74 (m, H$^A$-CH$_2$); 2.74-2.88 (t, CH$_2$); 2.93-3.09 (m, CH$_2$); 3.37-3.55 (m, CH$_2$, H$^B$-CH$_2$); 6.82 (dt, 1H-aromatic); 7.00 (dd, 1H-aromatic); 7.08-7.27 (m, 6H-aromatic) | 104-105 |
| 89 | CDCl$_3$; 1.53-1.70 (m, H$^A$-CH$_2$); 1.88-2.02 (m, H$^B$-CH$_2$); 2.49-2.68 (m, CH, H$^A$-CH$_2$); 2.80 (t, CH$_2$); 2.91-3.13 (m, CH$_2$, H$^B$-CH$_2$); | 87.5-89.5 |

| Co. No. | NMR data | melting point (° C.) |
|---|---|---|
| | 3.39-3.62 (m, CH$_2$); 5.90 (s, CH$_2$); 6.58-6.73 (m, 3H-aromatic); 7.12-7.32 (m, 5H-aromatic) | |
| 90 | mixture of 2 diastereoisomers | |
| 91 | CDCl$_3$; 1.52 (d, CH$_3$); 2.45-2.66 (m, H$^A$-CH$_2$); 2.00-2.21 (m, H$^B$-CH$_2$); 2.28 (s, 2x CH$_3$); 2.67-2.87 (m, CH, H$^A$-CH$_2$); 3.19-3.31 (dt, H$^B$-CH$_2$); 3.46-3.62 (m, CH); 5.51 (q, CH); 5.57 (s, OH); 6.92 (s, 1H-aromatic); 6.99 (d, 1H-aromatic); 7.19-7.38 (m, 5H-aromatic) 7.43 (d, 1H-aromatic) | |
| 92 | CDCl$_3$; 1.72-1.97 (m, CH$_2$); 2.75-3.26 (m, CH, 2x CH$_2$, H$^A$-CH$_2$); 3.39-3.62 (m, CH$_2$, H$^B$-CH$_2$); 3.78 (s, CH$_3$); 6.84 (m. 2H-aromatic); 7.08-7.19 (m, 3H-aromatic); 7.28 (d, 2H-aromatic) | |
| 93 | CDCl$_3$; 1.72-1.90 (m, CH$_2$); 2.30 (s, CH$_3$); 2.75-2.88 (t, CH$_2$); 2.88-3.27 (m, CH, CH$_2$, H$^A$-CH$_2$); 3.38-3.48 (dd, H$^B$-CH$_2$); 3.48-3.60 (m, CH$_2$); 7.00-7.16 (m, 5H-aromatic); 7.25 (d, 2H-aromatic) | |
| 94 | CDCl$_3$; 0.89 (t, CH$_3$); 1.66-1.99 (m, CH$_2$, H$^A$-CH$_2$, H$^B$-CH$_2$); 2.69-2.89 (m, CH, H$^A$-CH$_2$); 2.99 (m, H$^A$-CH$_2$); 3.19 (m, H$^B$-CH$_2$); 3.43 (dd, H$^B$-CH$_2$); 5.15 (t, CH); 6.98 (t, 1H-aromatic); 7.22 (7H-aromatic) | |
| 95 | CDCl$_3$; 0.94 (t, CH$_3$); 1.64-2.11 (m, 2x CH$_2$); 2.90-3.08 (m, CH, 2x H$^A$-CH$_2$); 3.08-3.21 (m, H$^B$-CH$_2$); 3.42-3.58 (m, H$^B$-CH$_2$); 5.23 (q, CH); 7.07 (t, 1H-aromatic); 7.20-7.38 (m, 7H-aromatic) | |
| 96 | CDCl$_3$; 0.91 (t, CH$_3$); 1.70-1.82 (m, CH$_2$); 1.82-2.01 (m, CH$_2$); 2.71-2.92 (m, CH, H$^A$-CH$_2$); 2.94-3.08 (m, H$^A$-CH$_2$); 3.16-3.28 (m, H$^B$-CH$_2$); 3.40-3.50 (dd, H$^B$-CH$_2$); 5.17 (q, CH); 7.00 (t, 1H-aromatic); 7.12-7.27 (m, 7H-aromatic) | |
| 97 | CDCl$_3$; 0.85 (t, CH$_3$); 1.57-2.00 (m, 2x CH$_2$); 2.82-2.99 (m, CH, 2x H$^A$-CH$_2$); 2.99-3.11 (m, H$^B$-CH$_2$); 3.32-3.49 (m, H$^B$-CH$_2$); 5.14 (q, CH); 6.98 (t, 1H-aromatic); 7.11-7.29 (m, 7H-aromatic) | |
| 98 | CDCl$_3$; 1.81-1.96 (m, CH$_2$); 2.85-3.17 (m, CH, 2x H$^A$-CH$_2$); 3.37-3.55 (m, 2x H$^B$-CH$_2$); 3.44 (s, CH$_3$); 3.77-3.87 (m, H$^A$-CH$_2$); 3.89-4.00 (m, H$^B$-CH$_2$); 5.50 (q, CH); 7.09 (t, 1H-aromatic); 7.20-7.38 (m, 7H-aromatic) | |
| 99 | CDCl$_3$, 1.73-2.00 (m, H$^A$-CH$_2$, H$^B$-CH$_2$); 2.92-3.34 (m, CH, CH$_2$, H$^A$-CH$_2$); 3.40 (s, CH$_3$); 3.42-3.60 (m, H$^B$-CH$_2$); 3.76-3.97 (m, CH$_2$); 5.49 (dd, CH); 7.02-7.11 (m, 1H-aromatic); 7.21-7.40 (m, 7H-aromatic) | |
| 100 | CDCl$_3$; 1.81-1.97 (m, CH$_2$); 2.85-3.18 (m, CH, 2x H$^A$-CH$_2$); 3.38-3.57 (m, 2x H$^B$-CH$_2$); 3.43 (s, CH$_3$); 3.77-3.88 (m, H$^A$-CH$_2$); 3.90-4.01 (m, H$^B$-CH$_2$); 5.50 (q, CH); 7.07 (t, 1H-aromatic); 7.20-7.39 (m, 7H-aromatic) | |
| 101 | CDCl$_3$; 1.73-2.02 (m, CH$_2$); 2.95-3.60 (m, CH, 2x H$^A$-CH$_2$, 2x H$^B$-CH$_2$); 3.40 (s, CH$_3$); 3.74-3.85 (m, H$^A$-CH$_2$); 3.88-3.98 (m, H$^B$-CH$_2$); 5.50 (q, CH); 7.07 (t, 1H-aromatic); 7.21-7.40 (m, 7H-aromatic) | |
| 102 | contains 10% from isomer LIB-90-B CDCl$_3$; 1.60-1.86 (m, CH$_2$); 2.62-3.50 (m, CH, 3x H$^A$-CH$_2$, 3x H$^B$-CH$_2$); 5.67 (q, CH); 7.02 (t, 1H-aromatic); 7.11-7.43 (m, 12H-aromatic) | |
| 103 | mixture of diastereoisomers A and B CDCl$_3$; 1.50-1.83 (m, CH$_2$); 2.48-3.45 (m, CH, 3x H$^A$-CH$_2$, 3x H$^B$-CH$_2$); 5.61-5.80 (m, CH); 7.00 (t, 1H-aromatic); 7.11-7.43 (m, 12H-aromatic) | |
| 104 | CDCl$_3$; 1.83-1.98 (m, CH$_2$); 2.92-3.20 (m, CH, 2x H$^A$-CH$_2$); 3.29-3.42 (m, H$^B$-CH$_2$); 3.42-3.58 (m, H$^B$-CH$_2$); 3.72 (s, OH); 3.98-4.12 (m, H$^A$-CH$_2$); 4.12-4.26 (m, H$^B$-CH$_2$); 5.02 (q, CH); 7.08 (t, 1H-aromatic); 7.22-7.40 (m, 7H-aromatic) | |
| 105 | CDCl$_3$; 1.80 (m, CH$_2$); 2.97-3.33 (m, H$^A$-CH$_2$, CH, CH$_2$), 3.41-3.58 (m, H$^B$-CH$_2$); 3.91 (t, OH); 3.98-4.21 (m, CH$_2$), 5.04 (q, CH), 7.08 (t, 1H-aromatic); 7.19-7.42 (m, 7H-aromatic) | |
| 106 | CDCl$_3$; 1.82-2.01 (m, CH$_2$); 2.93-3.20 (m, CH, 2x H$^A$-CH$_2$); 3.27-3.40 (m, H$^B$-CH$_2$); 3.46-3.61 (m, OH, H$^B$-CH$_2$); 3.98-4.11 (m, H$^A$-CH$_2$); 4.12-4.27 (m, H$^B$-CH$_2$); 4.97 (q, CH); 7.10 (t, 1H-aromatic); 7.21-7.42 (m, 7H-aromatic) | |
| 107 | CDCl$_3$; 1.78-2.04 (m, CH$_2$); 2.96-3.34 (m, CH, 2x H$^A$-CH$_2$, H$^B$-CH$_2$); 3.41-3.59 (m, H$^B$-CH$_2$); 3.84-3.97 (m, OH); 3.08-4.21 (m, CH$_2$); 5.05 (q, CH); 7.09 (t, 1H-aromatic); 7.18-7.42 (m, 7H-aromatic) | |
| 108 | CDCl$_3$; 1.50-1.70 (m, H$^A$-CH$_2$); 1.88-2.05 (m, H$^B$-CH$_2$); 2.56-2.73 (m, CH, H$^A$-CH$_2$); 2.73-2.88 (t, CH$_2$); 2.94-3.23 (m, H$^A$-CH$_2$, 2x H$^B$-CH$_2$); 3.39-3.63 (m, CH$_2$); 6.68-6.85 (m, 2H-aromatic); 7.07-7.32 (m, 6H-aromatic) | |
| 109 | CDCl$_3$; 1.52-1.70 (m, H$^A$-CH$_2$); 1.85-2.01 (m, H$^B$-CH$_2$); 2.50-2.69 (m, CH, H$^A$-CH$_2$); 2.72-2.85 (t, CH$_2$); 2.86-2.99 (dt, H$^A$-CH$_2$); 2.99-3.13 (m, 2x H$^B$-CH$_2$); 3.41-3.58 (m, CH$_2$); 3.85 (s, CH$_3$); 5.11 (s, CH$_2$); 6.62 (dd, 1H-aromatic); 6.77 (d, 2H-aromatic); 7.10-7.46 (m, 10H-aromatic) | |

| Co. No. | NMR data | melting point (° C.) |
|---|---|---|
| 110 | CDCl$_3$; 1.58-1.77 (m, H$^A$-CH$_2$); 1.80-1.96 (m, CH$_2$); 1.96-2.11 (m, H$^B$-CH$_2$); 2.36 (s, CH$_3$); 2.47-2.79 (m, CH, CH$_2$, H$^A$-CH$_2$); 3.18-3.29 (m, H$^A$-CH$_2$, H$^B$-CH$_2$); 3.30-3.43 (m, CH$_2$, H$^B$-CH$_2$); 7.08-7.34 (m, 9H-aromatic) | |
| 111 | CDCl$_3$; 1.60-2.07 (m, CH$_2$, H$^A$-CH$_2$, H$^B$-CH$_2$); 2.56-2.68 (t, CH$_2$); 2.71-2.88 (m, CH, H$^A$-CH$_2$); 3.13-3.27 (m, H$^A$-CH$_2$, H$^B$-CH$_2$); 3.29-3.48 (m, CH$_2$, H$^B$-CH$_2$); 7.08-7.40 (m, 9H-aromatic) | |
| 112 | CDCl$_3$; 1.57-1.74 (m, H$^A$-CH$_2$); 1.76-1.92 (m, CH$_2$); 1.92-2.08 (m, H$^B$-CH$_2$); 2.61 (t, CH$_2$); 2.68-2.87 (m, CH, H$^A$-CH$_2$); 3.13-3.27 (m, H$^A$-CH$_2$, H$^B$-CH$_2$); 3.28-3.42 (m, CH$_2$, H$^B$-CH$_2$); 6.82-6.96 (dt, 1H-aromatic); 7.03-7.33 (m, 7H-aromatic) | |
| 113 | CDCl$_3$; 1.61-1.79 (m, H$^A$-CH$_2$); 1.81-2.08 (m, CH$_2$, H$^B$-CH$_2$); 2.38 (s, 2x CH$_3$); 2.58-2.73 (m, CH, CH$_2$, H$^A$-CH$_2$); 3.15-3.46 (m, CH$_2$, H$^A$-CH$_2$, 2x H$^B$-CH$_2$); 7.04 (s, 3H-aromatic); 7.13-7.35 (m, 5H-aromatic) | |
| 114 | CDCl$_3$; 1.76-2.00 (m, 2x CH$_2$); 2.63 (t, CH$_2$); 2.82-3.55 (m, CH, 3x CH$_2$); 7.01-7.36 (m, 8H-aromatic) | |
| 115 | CDCL$_3$; 1.77 (s, CH$_3$); 1.79 (s, CH$_3$); 1.88 (m, CH$_2$); 2.82-2.97 (m, CH); 3.05 (t, H$^A$-CH$_2$); 3.18-3.40 (m, CH$_2$); 3.45 (dd, H$^B$-CH$_2$); 7.07 (t, 1H-aromatic); 7.17-7.39 (m, 7H-aromatic) | |
| 116 | CDCl$_3$; 1.52 (d, CH$_3$); 1.78-2.17 (m, 3x CH$_2$); 2.82-3.19 (m, 2x CH$_2$, H$^A$-CH$_2$); 3.20-3.37 (m, H$^B$-CH$_2$); 5.62 (q, CH); 7.10-7.50 (m, 13H-aromatic); 7.55-7.67 (m, 2H-aromatic); 7.69-7.80 (m, 2H-aromatic); 7.93 (d, 1H-aromatic); 8.01 (d, 1H-aromatic) | |
| 117 | mixture of 2 diastereoisomers CDCl$_3$; 1.10 (d, 0.4x CH$_3$); 1.45 (d, 0.6x CH$_3$); 1.55 (s, 0.6x CH$_3$); 1.62 (s, 0.4x CH$_3$); 1.50-1.97 (m, CH$_2$); 2.48-3.66 (m, CH, 3x CH$_2$); 4.70-5.19 (OH); 5.26 (q, 0.4 CH); 5.43 (q, 0.6x CH); 6.97-7.44 (m, 9H-aromatic) | |
| 118 | 2 diastereoisomers | |
| 119 | CDCl$_3$; 1.51 (d, CH$_3$); 1.60-1.79 (m, HA -CH$_2$); 1.85-2.00 (m, H$^B$-CH$_2$); 2.68-2.89 (m, CH, 2x H$^A$-CH$_2$); 3.17 (dt, H$^B$-CH$_2$); 3.36 (d, H$^B$-CH$_2$); 3.85 (s, 2x CH$_3$); 5.52 (q, CH); 6.78 (d, 1H-aromatic); 7.00 (d, 1H-aromatic); 7.29 (m, 5H-aromatic) | |
| 120 | CDCl$_3$; 1.51 (d, CH$_3$); 1.60 (m, H$^A$-CH$_2$); 1.98 (m, H$^B$-CH$_2$); 2.68-2.93 (m, CH, 2x H$^A$-CH$_2$); 3.16 (m, H$^B$-CH$_2$); 3.40 (dd, H$^B$-CH$_2$); 3.84 (s, 2x CH$_3$); 5.49 (q, CH); 6.72 (d, 1H-aromatic); 6.97 (d, 1H-aromatic); 7.28 (m, 5H-aromatic) | |
| 121 | CDCl$_3$; 1.50 (d, CH$_3$); 1.55-1.70 (m, H$^A$-CH$_2$); 1.91-2.08 (m, H$^B$-CH$_2$); 2.60-2.89 (m, CH, 2x H$^A$-CH$_2$); 3.06-3.23 (m, H$^B$-CH$_2$); 3.84 (s, CH$_3$); 5.12 (s, CH$_2$); 5.49 (q, CH); 6.58-6.68 (dd, 1H-aromatic); 6.71-6.82 (m, 2H-aromatic); 7.16-7.48 (m, 10H-aromatic) | |
| 122 | CDCl$_3$; 1.43 (d, CH$_3$); 1.59-1.77 (m, H$^A$-CH$_2$); 1.83-2.01 (m, H$^B$-CH$_2$); 2.61-2.83 (m, CH, 2x H$^A$-CH$_2$); 2.93-3.20 (m, 2x H$^B$-CH$_2$); 3.87 (s, CH$_3$); 5.12 (s, CH$_2$); 5.51 (q, CH); 6.61-6.72 (dd, 1H-aromatic); 6.73-6.83 (m, 2H-aromatic); 7.17-7.45 (m, 10H-aromatic) | |
| 123 | CDCl$_3$; 1.50 (d, CH$_3$); 1.56-1.86 (m, CH$_2$); 2.02-2.47 (m, CH, CH$_2$); 2.59-2.90 (m, H$^A$-CH$_2$, CH$_2$); 3.18-3.31 (dt, H$^B$-CH$_2$); 3.79 (s, CH$_3$); 5.51 (q, CH); 6.87-6.91 (m, 2H-aromatic); 7.08-7.36 (m, 7H-aromatic) | |
| 124 | CDCl$_3$; 1.49 (d, CH$_3$); 1.52-1.69 (m, CH$_2$); 2.08-2.33 (m, CH, H$^A$-CH$_2$); 2.37-2.52 (m, H$^B$-CH$_2$); 2.58-2.79 (m, CH$_2$); 2.83-2.98 (dt, H$^A$-CH$_2$); 3.12-3.27 (m, H$^B$-CH$_2$); 3.78 (s, CH$_3$); 5.49 (q, CH); 6.74-6.90 (m, 2H-aromatic); 7.08-7.38 (m, 7H-aromatic) | |
| 125 | CDCl$_3$; 1.43 (d, CH$_3$); 1.48-1.68 (m, CH$_2$); 1.93-2.22 (m, CH, H$^A$-CH$_2$); 2.23-2.39 (m, H$^B$-CH$_2$); 2.48-2.70 (m, CH$_2$); 2.70-2.82 (m, H$^A$-CH$_2$); 3.10-3.22 (dt, H$^B$-CH$_2$); 3.75 (s, CH$_3$); 3.78 (s, CH$_3$); 5.42 (q, CH); 6.60-6.72 (m, 3H-aromatic); 7.10-7.27 (m, 5H-aromatic) | |
| 126 | CDCl$_3$; 1.48 (d, CH$_3$); 1.45-1.70 (m, CH$_2$); 2.04-2.38 (m, CH, H$^A$-CH$_2$); 2.35-2.51 (m, H$^B$-CH$_2$); 2.52-2.74 (m, CH$_2$); 2.85-2.97 (dt, H$^A$-CH$_2$); 3.12-3.26 (m, H$^B$-CH$_2$); 3.81 (s, CH$_3$); 3.84 (s, CH$_3$); 5.46 (q, CH); 6.67-6.79 (m, 3H-aromatic); 7.17-7.35 (m, 5H-aromatic) | |
| 127 | CDCl$_3$; 1.56 (d, CH$_3$); 1.60-1.79 (m, CH$_2$); 2.08-2.29 (m, CH, H$^A$-CH$_2$); 2.37 (s, CH$_3$); 2.39-2.54 (m, H$^B$-CH$_2$); 2.69-2.80 (t, CH$_2$); 2.82-2.97 (m, H$^A$-CH$_2$); 3.23-3.36 (dt, H$^B$-CH$_2$); 5.56 (q, CH); 7.07-7.22 (m, 4H-aromatic); 7.22-7.40 (m, 5H-aromatic) | |
| 128 | CDCl$_3$; 1.55 (d, CH$_3$); 1.55-1.75 (m, CH$_2$); 2.10-2.30 (m, CH, H$^A$-CH$_2$); 2.35 (s, CH$_3$); 2.46-2.61 (m, H$^B$-CH$_2$); 2.66-2.78 (t, CH$_2$); 2.90-3.03 (dt, H$^A$-CH$_2$); 3.18-3.32 (m, H$^B$-CH$_2$); 5.55 (q, CH); 7.04-7.22 (m, 4H-aromatic); 7.23-7.40 (m, 5H-aromatic) | |
| 129 | CDCl$_3$; 1.44 (d, CH$_3$); 1.33-1.62 (m, CH$_2$); 2.06-2.24 (m, CH, H$^A$-CH$_2$); 2.33-2.44 (dq, H$^B$-CH$_2$); 2.71-2.92 (m, CH$_2$, H$^A$-CH$_2$); | |

| Co. No. | NMR data | melting point (° C.) |
|---|---|---|
| | 3.09-3.22 (m, H$^B$-CH$_2$); 5.41 (q, CH); 6.80-6.92 (m, 1H-aromatic); 6.93-7.11 (m, 2H-aromatic); 7.13-7.30 (m, 5H-aromatic) | |
| 130 | CDCl$_3$; 1.53 (d, CH$_3$); 1.56-1.76 (m, CH$_2$); 2.02-2.19 (m, H$^A$-CH$_2$); 2.19-2.32 (m, CH); 2.32-2.49 (m, H$^B$-CH$_2$); 2.53-2.78 (m, CH$_2$); 2.78-2.93 (m, H$^A$-CH$_2$); 2.92 (s, 2x CH$_3$); 3.20-3.32 (dt, H$^B$-CH$_2$); 5.54 (q, CH); 6.71 (d, 2H-aromatic); 7.11 (d, 2H-aromatic); 7.22-7.39 (m, 5H-aromatic) | |
| 131 | CDCl$_3$; 1.51 (d, CH$_3$); 1.50-1.71 (m, CH$_2$); 2.08-2.33 (m, CH, H$^A$-CH$_2$); 2.38-2.53 (m, H$^B$-CH$_2$); 2.53-2.76 (m, CH$_2$); 2.85-2.99 (m, H$^A$-CH$_2$); 2.92 (s, 2x CH$_3$); 3.13-3.28 (m, H$^B$-CH$_2$); 5.51 (q, CH); 6.70 (d, 2H-aromatic); 7.10 (d, 2H-aromatic); 7.21-7.39 (m, 5H-aromatic) | |
| 132 | CDCl$_3$; 1.52 (d, CH$_3$); 1.56-1.73 (m, CH$_2$); 2.01-2.17 (m, H$^A$-CH$_2$); 2.17-2.29 (m, CH); 2.30-2.46 (m, H$^B$-CH$_2$); 2.54-2.77 (m, CH$_2$); 2.78-2.90 (m, H$^A$-CH$_2$); 3.19-3.31 (dt, H$^B$-CH$_2$); 3.77 (s, CH$_3$); 5.52 (q, CH); 6.82 (d, 2H-aromatic); 7.13 (d, 2H-aromatic); 7.20-7.38 (m, 5H-aromatic) | |
| 133 | CDCl$_3$; 1.49 (d, CH$_3$); 1.48-1.69 (m, CH$_2$); 2.04-2.32 (m, CH, H$^A$-CH$_2$); 2.33-2.50 (m, H$^B$-CH$_2$); 2.51-2.76 (m, CH$_2$); 2.84-2.97 (dt, H$^A$-CH$_2$); 3.11-3.26 (m, H$^B$-CH$_2$); 3.75 (s, CH$_3$); 5.48 (q, CH); 6.81 (d, 2H-aromatic); 7.11 (d, 2H-aromatic); 7.18-7.37 (m, 5H-aromatic) | |
| 134 | CDCL$_3$; 1.31 (d, CH$_3$); 1.52 (d, CH$_3$); 1.61 (m, CH$_2$); 1.98-2.16 (m, CH, H$^A$-CH$_2$); 2.36 (dt, H$^B$-CH$_2$); 2.68-2.90 (m, CH, H$^A$-CH$_2$); 3.22 (dt, H$^B$-CH$_2$); 5.50 (q, CH); 7.12-7.38 (m, 10H-aromatic) | |
| 135 | CDCl$_3$; 1.19 (d, CH$_3$); 1.24 (m, H$^A$-CH$_2$); 1.39 (d, CH$_3$); 1.45 (m, H$^B$-CH$_2$); 1.77 (m, H$^A$-CH$_2$); 2.10-2.21 (m, H$^B$-CH$_2$); 2.25-2.39 (m, CH); 2.74 (dt, H$^A$-CH$_2$); 2.87 (m, CH); 3.02 (m, H$^B$-CH$_2$); 5.39 (q, CH); 7.03-7.27 (m, 10H aromatic) | |
| 136 | CDCl$_3$; 1.28 (d, CH$_3$); 1.37-1.65 (m, CH$_2$); 1.49 (d, CH$_3$); 1.73-1.92 (m, H$^A$-CH$_2$); 2.17-2.43 (m, CH, H$^B$-CH$_2$); 2.68-2.81 (m, H$^A$-CH$_2$); 2.85-3.02 (m, CH); 3.09-3.21 (dt, H$^B$-CH$_2$); 5.50 (q, CH); 7.12-7.37 (m, 10H-aromatic) | |
| 137 | CDCl$_3$; 1.30 (d, CH$_3$), 1.44 (d, CH$_3$); 1.5 (m, CH$_2$); 2.01-2.21 (m, CH, H$^A$-CH$_2$); 2.27-2.42 (dt, H$^B$-CH$_2$); 2.68-2.82 (m, CH); 2.83-2.95 (dt, H$^A$-CH$_2$), 3.05-3.19 (m, H$^B$-CH$_2$); 5.46 (q, CH); 7.15-7.38 (m, 10H-aromatic) | |
| 138 | CDCl$_3$; 0.77 (t, CH$_3$); 1.20-1.85 (m, 2x CH$_2$, H$^A$-CH$_2$); 1.48 (d, CH$_3$); 2.19-2.39 (m, CH, H$^B$-CH$_2$); 2.61-2.79 (m, CH, H$^A$-CH$_2$); 3.03-3.18 (m, H$^B$-CH$_2$); 5.48 (q, CH); 7.11-7.37 (m, 10H-aromatic) | |
| 139 | CDCl$_3$; 0.80 (t, CH$_3$); 1.51 (d, CH$_3$); 1.51-1.78 (m, 2x CH$_2$); 2.01 (m, CH, H$^A$-CH$_2$); 2.35 (dt, H$^B$-CH$_2$); 2.47 (m, CH); 2.72 (m, H$^A$-CH$_2$); 3.20 (dt, H$^B$-CH$_2$); 5.49 (q, CH); 7.13-7.32 (10H-aromatic) | |
| 140 | mixture of 3 diastereoisomers CDCL$_3$, 0.70-0.84 (m, CH$_3$); 1.18-1.84 (m, 2x CH$_2$, CH$_3$); 1.93-2.18 (m, H$^A$-CH$_2$, 0.6x CH); 2.23-2.55 (m, H$^B$-CH$_2$, 0.4x CH, 0.7x CH); 2.67-3.94 (m, H$^A$-CH$_2$, 0.3x CH); 3.00-3.26 (m, H$^B$-CH$_2$); 5.39-5.55 (m, CH); 7.10-7.40 (m, 10H-aromatic) | |
| 141 | CDCl$_3$; 0.79 (t, CH$_3$); 1.17-1.82 (m, 2x CH$_2$); 1.43 (d, CH$_3$); 1.98-2.08 (m, CH, H$^A$-CH$_2$); 2.25-2.52 (m, CH, H$^B$-CH$_2$); 2.82-2.95 (m, H$^A$-CH$_2$); 3.00-3.18 (m, H$^B$-CH$_2$); 5.45 (q, CH); 7.12-7.39 (m, 10H-aromatic) | |
| 142 | CDCl$_3$; 1.12 (s, CH$_3$); 1.27 (d, CH$_3$); 1.43-1.60 (m, H$^A$-CH$_2$); 1.79-1.92 (m, H$^B$-CH$_2$); 2.27 (s, CH$_3$); 2.51-2.62 (m, CH$_2$); 2.73 (d, H$^A$-CH$_2$); 2.96 (d, H$^B$-CH$_2$); 5.40 (q, CH); 6.97-7.24 (m, 9H-aromatic) | |
| 143 | CDCl$_3$; 1.16 (s, CH$_3$); 1.39 (d, CH$_3$); 1.49-1.61 (m, H$^A$-CH$_2$); 1.65-1.80 (m, H$^B$-CH$_2$); 2.19 (s, CH$_3$); 2.41-2.52 (dt, H$^A$-CH$_2$); 2.70 (d, H$^A$-CH$_2$); 2.96 (d, H$^B$-CH$_2$); 2.97-3.09 (m, H$^A$-CH$_2$); 5.36 (q, CH); 6.88-7.22 (m, 9H-aromatic) | |
| 144 | CDCl$_3$; 0.81 (t, CH$_3$); 1.20 (d, CH$_3$); 1.40-1.78 (m, 2x CH$_2$); 2.25 (s, CH$_3$); 2.27-2.39 (m, H$^A$-CH$_2$); 2.43-2.57 (m, H$^B$-CH$_2$); 2.72 (d, H$^A$-CH$_2$); 2.97 (d, H$^B$-CH$_2$); 5.41 (q, CH); 6.94-7.27 (m, 9H-aromatic) | |
| 145 | CDCl$_3$; 0.97 (t, CH$_3$); 1.46 (d, CH$_3$); 1.52-1.89 (m, 2x CH$_2$); 2.25 (s, CH$_3$); 2.30-2.47 (m, H$^A$-CH$_2$); 2.74 (d, H$^A$-CH$_2$); 2.98-3.13 (m, H$^B$-CH$_2$); 3.10 (d, H$^B$-CH$_2$); 5.48 (q, CH); 6.90-7.27 (m, 9H-aromatic) | |
| 146 | mixture of 2 diastereoisomers CDCl$_3$; 0.79-0.93 (m, CH$_3$); 1.19 (d, 0.7x CH$_3$); 1.38 (d, 0.3x CH$_3$); 1.08-1.79 (m, 3x CH$_2$); 2.17 (s, 0.3x CH$_3$); 2.25 (s, 0.7x CH$_3$); 2.27-2.38 (m, H$^A$-CH$_2$); 2.43-2.57 (m, H$^B$-CH$_2$); 2.60-2.77 (m, H$^A$-CH$_2$); 2.89-3.07 (m, H$^B$-CH$_2$); 5.40 (q, CH); 6.92-7.28 (m, 9H-aromatic) | |
| 147 | mixture of 2 diastereoisomers | |
| 148 | CDCl$_3$; 1.48 (d, CH$_3$); 1.53-1.69 (m, H$^A$-CH$_2$); 1.74-1.90 (m, H$^B$-CH$_2$); 2.29 (s, 2x CH$_3$); 2.49-2.78 (m, CH, 2x H$^A$-CH$_2$); | |

| Co. No. | NMR data | melting point (° C.) |
|---|---|---|
| | 3.12-3.31 (m, 2x $H^B$-$CH_2$); 5.47 (q, CH); 6.93 (s, 3H-aromatic); 7.11-7.30 (m, 5H-aromatic) | |
| 149 | $CDCl_3$; 1.44 (d, $CH_3$); 1.40-1.60 (m, $H^A$-$CH_2$); 1.80-1.96 (m, $H^B$-$CH_2$); 2.25 (s, 2x $CH_3$); 2.49-2.67 (m, CH, $H^A$-$CH_2$); 2.81-2.92 (dt, $H^A$-$CH_2$); 3.00-3.13 (m, $H^B$-$CH_2$); 3.21-3.36 (m, $H^B$-$CH_2$); 5.43 (q, CH); 6.91 (s, 3H-aromatic); 7.13-7.32 (m, 5H-aromatic) | |
| 150 | $CDCl_3$; 1.51 (d, $CH_3$); 1.59-1.78 (m, $H^A$-$CH_2$); 1.87-2.02 (m, $H^B$-$CH_2$); 2.70-2.89 (m, CH, 2x $H^A$-$CH_2$); 3.10-3.23 (dt, $H^B$-$CH_2$); 3.28-3.43 (m, $H^B$-$CH_2$); 5.51 (q, CH); 6.87-6.98 (dt, 1H-aromatic); 7.10 (dd, 1H-aromatic); 7.21-7.38 (m, 6H-aromatic) | |
| 151 | $CDCl_3$; 1.50 (d, $CH_3$); 1.50-1.67 (m, $H^A$-$CH_2$); 1.92-2.08 (m, $H^B$-$CH_2$); 2.73-2.93 (m, CH, 2x $H^A$-$CH_2$); 3.12-3.25 (m, $H^B$-$CH_2$); 3.28-3.44 (m, $H^B$-$CH_2$); 5.49 (q, CH); 6.80-6.91 (dt, 1H-aromatic); 7.08 (dd, 1H-aromatic); 7.19-7.38 (m, 6H-aromatic) | |
| 152 | $CDCl_3$; 1.46 (d, $CH_3$); 1.59-1.76 (m, $H^A$-$CH_2$); 1.87-2.02 (m, $H^B$-$CH_2$); 2.59-2.86 (m, CH, 2x $H^A$-$CH_2$); 2.99-3.18 (m, 2x $H^B$-$CH_2$); 5.51 (q, CH); 5.91 (s, $CH_2$); 6.60-6.75 (m, 3H-aromatic); 7.19-7.38 (m, 5H-aromatic) | |
| 153 | contains 8% from isomer LIB-59-A<br>$CDCl_3$; 1.50 (d, $CH_3$); 1.48-1.67 (m, $H^A$-$CH_2$); 1.89-2.08 (m, $H^B$-$CH_2$); 2.58-2.87 (m, CH, 2x $H^A$-$CH_2$); 3.04-3.22 (m, 2x $H^B$-$CH_2$); 5.49 (q, CH); 5.90 (s, $CH_2$); 6.59-7.75 (m, 3H-aromatic); 7.18-7.37 (m, 5H-aromatic) | |
| 154 | $CDCl_3$; 1.43 (d, $CH_3$); 1.55-1.72 (m, $H^A$-$CH_2$); 1.78-1.93 (m, $H^B$-$CH_2$); 2.60-2.81 (m, CH, 2x $H^A$-$CH_2$); 3.04-3.28 (m, 2x $H^B$-$CH_2$); 5.44 (q, CH); 5.86 (s, $CH_2$); 6.69 (s, 1H-aromatic); 6.73 (s, 1H-aromatic); 7.12-7.30 (m, 5H-aromatic) | |
| 155 | $CDCl_3$; 1.43 (d, $CH_3$); 1.45-1.58 (m, $H^A$-$CH_2$); 1.83-1.99 (m, $H^B$-$CH_2$); 2.58-2.86 (m, CH, 2x $H^A$-$CH_2$); 3.03-3.18 (m, $H^B$-$CH_2$); 3.18-3.27 (dd, $H^B$-$CH_2$); 5.41 (q, CH); 5.85 (s, $CH_2$); 6.69 (s, 1H-aromatic); 6.71 (s, 1H-aromatic); 7.11-7.29 (m, 5H-aromatic) | |
| 156 | $CDCl_3$; 1.51 (d, $CH_3$); 1.55-1.72 (m, $CH_2$); 1.91-2.08 (m, $H^A$-$CH_2$); 2.37-2.57 (m, CH, $H^B$-$CH_2$); 2.72-2.87 (m, $H^A$-$CH_2$); 3.14-3.28 (m, $H^B$-$CH_2$); 3.19 (s, $CH_3$); 4.34 (m, CH); 5.50 (q, CH); 7.20-7.39 (m, 10H-aromatic) | |
| 157 | $CDCl_3$; 1.50 (d, $CH_3$); 1.51-1.68 (m, $H^A$-$CH_2$); 1.72-1.88 (m, $H^B$-$CH_2$); 2.10-2.23 (m, CH, $H^A$-$CH_2$); 2.43-2.58 (m, $H^B$-$CH_2$); 2.85-2.95 (dt, $H^A$-$CH_2$); 3.12-3.23 (m, $H^B$-$CH_2$); 3.21 (s, $CH_3$); 4.43 (dd, CH); 5.46 (q, CH); 7.19-7.38 (m, 10H-aromatic) | |
| 158 | $CDCl_3$; 1.23 (d, $CH_3$); 1.35 (d, $CH_3$); 1.73 (m, $CH_2$); 2.65 (m, CH, $H^A$-$CH_2$); 2.91 (m, $H^B$-$CH_2$); 3.37 (m, CH); 5.44 (q, CH); 7.18 (m, 10H-aromatic) | |
| 159 | $CDCl_3$; 1.14 (d, $CH_3$); 1.35 (d, $CH_3$); 1.50-1.65 (m, $H^A$-$CH_2$); 1.65-1.80 (m, $H^B$-$CH_2$), 2.39-2.62 (m, CH, $CH_2$); 3.23-3.38 (m, CH); 5.33 (q, CH); 7.05-7.23 (m, 10H-aromatic) | |
| 160 | $CDCl_3$; 1.15 (d, $CH_3$); 1.41 (d, $CH_3$); 1.63-1.78 (m, $CH_2$); 2.68-2.80 (m, CH, $H^A$-$CH_2$); 3.00-3.13 (m, $H^B$-$CH_2$); 3.38-3.50 (m, CH); 5.44 (q, CH); 7.03-7.30 (m, 10H-aromatic) | |
| 161 | $CDCl_3$; 1.36 (d, $CH_3$); 1.37 (d, $CH_3$); 1.41-1.59 (m, $H^A$-$CH_2$); 1.72-1.90 (m, $H^B$-$CH_2$); 2.32-2.47 (dt, CH); 2.57-2.70 (m, $H^A$-$CH_2$); 2.89-3.02 (m, $H^B$-$CH_2$); 3.25-3.39 (m, CH); 5.32 (q, CH); 6.82-6.94 (m, 2H-aromatic); 7.01-7.20 (m, 8H-aromatic) | |
| 162 | $CDCl_3$; 1.27 (d, 0.65x $CH_3$); 1.44 (d, 0.35x $CH_3$); 1.52 (d, 0.35x $CH_3$); 1.55 (d, 0.65x $CH_3$); 1.65-2.02 (m, $CH_2$); 2.38 (s, 0.35x $CH_3$); 2.43 (s, 0.65x $CH_3$); 2.62-2.87 (m, CH, $H^A$-$CH_2$); 2.97-3.08 (m, 0.35x $H^B$-$CH_2$); 3.13-3.26 (m, 0.65x $H^B$-$CH_2$); 3.27-3.39 (m, 0.35x CH); 3.74-3.88 (m, 0.65x CH); 5.47-5.62 (m, CH); 7.05-7.39 (m, 9H-aromatic) | |
| 163 | $CDCl_3$; 1.09 (d, 0.8x $CH_3$); 1.40 (d, 0.2x $CH_3$); 1.42 (d, $CH_3$); 1.57-1.87 (m, $CH_2$); 2.19 (s, 0.2x $CH_3$); 2.32 (s, 0.8x $CH_3$); 2.57-2.70 (m, CH, 0.2x $H^A$-$CH_2$); 2.74-2.87 (dt, 0.8x $H^A$-$CH_2$); 2.92-3.20 (m, 0.2x CH, $H^B$-$CH_2$); 3.66-3.78 (m, 0.8x CH); 5.32-5.51 (m, CH); 6.90-7.29 (m, 9H-aromatic) | |
| 164 | $CDCl_3$; 1.84 (m, $CH_2$); 2.15 (m, $CH_2$); 2.43-2.59 (m, 2x $CH_2$); 3.05-3.27 (m, 2x $CH_2$); 3.86 (s, 2x $CH_3$); 5.12 (s, 2x $CH_2$); 6.66 (dd, 2H-aromatic); 6.73-6.84 (m, 4H-aromatic); 6.89-6.99 (m, 2H-aromatic) 7.11-7.46 (m, 13H-aromatic) | |
| 165 | mixture of diastereoisomers | |
| 166 | $CDCl_3$; 1.54 (d, 3H, $CH_3$); 1.60 (s, 3H, $CH_3$); 1.96-2.14 (m, 1H, $H^A$-$CH_2$); 2.28-2.41 (m, 1H, $H^B$-$CH_2$); 2.84-2.93 (m, 1H, $H^A$-$NCH_2$); 3.12-3.31 (m, $H^B$-$NCH_2$); 5.58 (m, CH); 7.28-7.54 (m, 10H-aromatic) | |

-continued

| Co. No. | NMR data | melting point (° C.) |
|---|---|---|
| 167 | CDCl$_3$; 1.54 (d, 3H, CH$_3$); 1.60 (s, 3H, CH$_3$); 1.96-2.14 (m, 1H, H$^A$-CH$_2$); 2.28-2.41 (m, 1H, H$^B$-CH$_2$); 2.84-2.93 (m, 1H, H$^A$-NCH$_2$); 3.12-3.31 (m, H$^B$-NCH$_2$); 5.58 (m, CH); 7.28-7.54 (m, 10H-aromatic) | |

C. Pharmacological Examples

Example C.1: Enzymatic Assays to Test the Effect of Compounds on 11b-Hydroxysteroid Dehydrogenase Type 1 and Type 2

The effects of compounds on 11b-HSD1 dependent conversion of cortisone into cortisol (reductase activity) was studied in a reaction mixture containing 30 mM Tris-HCl buffer pH 7.2, 180 µM NADPH, 1 mM EDTA, 2 µM cortisone, 1 µl drug and/or solvent and 11 µg recombinant protein in a final volume of 100 µl.

The effect on the 11b-HSD1-dehydrogenase activity (conversion of cortisol into cortisone) was measured in a reaction mixture containing 0.1M sodium phosphate buffer pH 9.0, 300 µM NADP, 25 µM cortisol, 1 µl drug and/or solvent and 3.5 µg recombinant protein in a final volume of 100 µl.

The effects on the 11b-HSD2 dependent dehydrogenase activity was studied in a reaction mixture containing 0.1M sodium phosphate buffer pH 7.5, 300 µM NAD, 100 nM cortisol (of which 2 nM is 3H-radio labelled), 1 µl drug and/or solvent and 2.5 µg recombinant protein in a final volume of 100 µl.

All incubations were performed for 45 min at 37 C in a water bath. The reaction was stopped by adding 100 µl acetonitrile containing 20 µg corticosterone as internal standard. After centrifugation, the product formation was analysed in the supernatant by HPLC on a Hypersyl BDS-C18 column using 0.05 mM ammonium acetate/methanol (50/50) as solvent. In all of the aforementioned assays, the drugs to be tested were taken from a stock solution and tested at a final concentration ranging from $-10^{-5}$M to $3.10^{-9}$M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below. (in this table NT stands for Not Tested).

Example C2: Cellular Assays to Test the Effect of Compounds on 11b-Hydroxysteroid Dehydrogenase Type 1 and Type 2

The effects on 11b-HSD1 activity was measured in differentiated 3T3-L1 cells and rat hepatocytes.

Mouse fibroblast 3T3-L1 cells (ATCC-CL-173) were seeded at a density of 16500 cells/ml in 12 well plates and grown for 7 days in DMEM medium (supplemented with 10% heat inactivated foetal calf serum, 2 mM glutamine and 25 mg gentamycin) at 37 C in a humidified 5% CO2 atmosphere. Medium was refreshed twice a week. Fibroblasts were differentiated into adipocytes at 37 C in a 5% CO2 humidified atmosphere in growth medium containing 2 µg/ml insulin, 55 µg/ml IBMX and 39.2 µg/ml dexamethasone.

Primary hepatocytes from male rats were seeded on BD-Biocoat Matrigel matrix multiwell plates at a density of 250000 cells/well and incubated for 10 days at 37 C in a 5% CO2 humidified atmosphere in DMEM-HAM's F12 medium containing 5% Nu-serum, 100 U/ml penicillin, 100 µg/ml streptomycin, 0.25 µg/ml amphotericin B, 50 µg/ml gentamycin sulfate, 5 µg/ml insulin and 392 ng/ml dexamethasone. Medium was refreshed 3 times a week.

Following a 4 hour pre-incubation with test compound, 0.5 µCi $^3$H-cortisone or dehydrocorticosterone, was added to the cultures. One hour later, the medium was extracted on Extrelut$^3$-columns with 15 ml diethyl ether and the extract was analysed by HPLC as described above.

The effects on 11b-HSD2 activity was studied in HepG2 and LCC-PK1-cells HepG2-cells (ATCC HB-8065) were seeded in 12 well plates at a density of 100,000 cells/ml and grown at 37 C in a humidified 5% CO2 atmosphere in MEM-Rega-3 medium supplemented with 10% heat inactivated foetal calf serum, 2 mM L-glutamine and sodium bicarbonate). Medium was refreshed twice a week.

Pig kidney cells (LCC-PK1, ATCC CRL-1392) were seeded at a density of 150,000 cells/ml in 12 well plates and grown at 37 C in a humidified 5% CO2 atmosphere in Medium 199 supplemented with Earls modified salt solution, 100 U/ml penicillin, 100 µg/ml streptomycin and 10% foetal calf serum. Medium was refreshed twice a week. Twenty four hours prior to the onset of the experiment, medium was changed by medium containing 10% charcoal stripped foetal calf serum.

Following a 4 hour pre-incubation with test compound, 0.5 µCi $^3$H-cortisol or corticosterone, was added to the cultures. One hour later, the medium was extracted on Extrelut$^3$-columns with 15 ml diethyl ether and the extract was analysed by HPLC as described above.

As for the enzymatic assays, the compounds to be tested were taken from a stock solution and tested at a final concentration ranging from $-10^{-5}$M to $3.10^{-9}$M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below (in this table NT stands for Not Tested).

| Compound Number | [C1] HSD1-prot Reduct Score | [C1] HSD2 prot Dehydro Score | [C2] HSD1 cellular 3T3-L1 Score | [C2] HSD2 cellular HepG2 Score |
|---|---|---|---|---|
| 1 | 3 | 1 | 3 | 1 |
| 2 | 2 | NT | 2 | 1 |
| 3 | 3 | NT | 2 | 1 |
| 4 | 1 | NT | 2 | 1 |
| 5 | 2 | NT | 2 | 1 |
| 6 | 2 | NT | 2 | 1 |
| 7 | 2 | 1 | 3 | 1 |
| 8 | 2 | NT | 2 | NT |
| 9 | 2 | 1 | 3 | 1 |
| 10 | 3 | 1 | 3 | 1 |
| 11 | 3 | NT | 2 | NT |
| 12 | 2 | NT | 2 | NT |

-continued

| Compound Number | [C1] HSD1-prot Reduct Score | [C1] HSD2 prot Dehydro Score | [C2] HSD1 cellular 3T3-L1 Score | [C2] HSD2 cellular HepG2 Score |
|---|---|---|---|---|
| 13 | 3 | 1 | 3 | 1 |
| 14 | 3 | 1 | 3 | 1 |
| 15 | 2 | NT | 2 | NT |
| 16 | 1 | NT | 2 | NT |
| 17 | 2 | NT | 2 | NT |
| 18 | 2 | NT | 2 | NT |
| 19 | 2 | NT | 3 | NT |
| 20 | 1 | NT | 1 | NT |
| 21 | 2 | NT | 3 | NT |
| 22 | 1 | NT | 2 | NT |
| 23 | 2 | NT | 3 | NT |
| 24 | 2 | NT | 1 | NT |
| 25 | 1 | NT | 3 | NT |
| 26 | 1 | NT | 2 | NT |
| 27 | 1 | 1 | 3 | 1 |
| 28 | 1 | 1 | 3 | 1 |
| 29 | 2 | NT | 2 | NT |
| 30 | 3 | 1 | 3 | 1 |
| 31 | 2 | 1 | 3 | 1 |
| 32 | 3 | 1 | 3 | 1 |
| 33 | 1 | NT | 3 | NT |
| 34 | 1 | NT | 2 | NT |
| 35 | 1 | 1 | 3 | 1 |
| 36 | 1 | NT | 2 | NT |
| 37 | 1 | NT | 2 | NT |
| 38 | 1 | NT | 2 | NT |
| 39 | 1 | NT | 2 | NT |
| 40 | 2 | NT | 3 | NT |
| 41 | 2 | 1 | 3 | 1 |
| 42 | 1 | NT | 2 | NT |
| 43 | 2 | NT | 2 | NT |
| 44 | 1 | NT | 2 | NT |
| 45 | 3 | 1 | 3 | 1 |
| 46 | 1 | NT | 1 | NT |
| 47 | 1 | NT | 2 | NT |
| 48 | 1 | NT | 2 | NT |
| 49 | 2 | NT | 3 | NT |
| 50 | 1 | NT | 2 | NT |
| 51 | 1 | NT | 2 | NT |
| 52 | 1 | NT | 2 | NT |
| 53 | 1 | NT | 2 | NT |
| 54 | 1 | NT | 2 | NT |
| 55 | 1 | NT | 2 | NT |
| 56 | 1 | NT | 2 | NT |
| 57 | 2 | 1 | 3 | 1 |
| 58 | 2 | NT | 2 | NT |
| 59 | 2 | 1 | 3 | 1 |
| 60 | 1 | NT | 2 | NT |
| 61 | 1 | NT | 2 | NT |
| 62 | 1 | NT | 2 | NT |
| 63 | 1 | NT | 2 | NT |
| 64 | 1 | NT | 2 | NT |
| 65 | 1 | 1 | 3 | 1 |
| 66 | 1 | NT | 2 | NT |
| 67 | 2 | NT | 3 | NT |
| 68 | 1 | NT | 2 | NT |
| 69 | 2 | NT | 3 | 1 |
| 70 | 1 | NT | 3 | 1 |
| 71 | 3 | NT | 3 | 1 |
| 72 | 1 | NT | 2 | NT |
| 73 | 3 | NT | 2 | NT |
| 74 | 2 | NT | 2 | NT |
| 75 | 3 | NT | 2 | NT |
| 76 | 3 | NT | 2 | NT |
| 77 | 3 | NT | 3 | 1 |
| 78 | 3 | NT | 3 | NT |
| 79 | 3 | NT | 3 | NT |
| 80 | 3 | NT | 3 | 1 |
| 81 | 1 | NT | 3 | NT |
| 82 | 3 | NT | 2 | NT |
| 83 | 3 | NT | 1 | NT |
| 84 | 2 | NT | 3 | NT |
| 85 | 2 | NT | 1 | NT |
| 86 | 2 | NT | 3 | NT |
| 87 | 1 | NT | 2 | NT |
| 88 | 2 | NT | 2 | NT |
| 89 | 1 | NT | 2 | NT |
| 90 | 1 | NT | 2 | NT |
| 91 | 2 | NT | 3 | NT |
| 92 | 3 | NT | 2 | NT |
| 93 | 1 | NT | 1 | NT |
| 94 | 1 | NT | 3 | NT |
| 95 | 3 | NT | 2 | NT |
| 96 | 2 | NT | 1 | NT |
| 97 | 3 | 2 | 1 | 1 |
| 98 | 1 | NT | 2 | NT |
| 99 | 3 | NT | 3 | NT |
| 100 | 2 | NT | 1 | NT |
| 101 | 1 | NT | 1 | NT |
| 102 | 1 | NT | 1 | NT |
| 103 | 1 | NT | 1 | NT |
| 104 | 1 | NT | 2 | NT |
| 105 | 3 | NT | 3 | NT |
| 106 | 2 | NT | 1 | NT |
| 107 | 2 | NT | 1 | NT |
| 108 | 2 | NT | 2 | NT |
| 109 | 1 | NT | 2 | NT |
| 110 | 2 | NT | 2 | NT |
| 111 | 2 | NT | 2 | NT |
| 112 | 2 | NT | 2 | NT |
| 113 | 2 | NT | 2 | NT |
| 114 | 1 | NT | 3 | NT |
| 115 | 1 | NT | 2 | NT |
| 116 | 1 | NT | 1 | NT |
| 117 | 3 | NT | 3 | NT |
| 118 | 1 | NT | 2 | NT |
| 119 | 3 | 2 | 3 | 1 |
| 120 | 2 | NT | 3 | NT |
| 121 | 1 | NT | 1 | NT |
| 122 | 2 | NT | 2 | NT |
| 123 | 2 | NT | 2 | NT |
| 124 | 2 | NT | 2 | NT |
| 125 | 1 | NT | 1 | NT |
| 126 | 1 | NT | 1 | NT |
| 127 | 2 | NT | 2 | NT |
| 128 | 2 | NT | 2 | NT |
| 129 | 2 | NT | 2 | NT |
| 130 | 1 | NT | 2 | NT |
| 131 | 1 | NT | 2 | NT |
| 132 | 2 | NT | 2 | NT |
| 133 | 1 | NT | 2 | NT |
| 134 | 3 | NT | 3 | NT |
| 135 | 1 | NT | 3 | NT |
| 136 | 2 | NT | 2 | NT |
| 137 | 3 | NT | 3 | NT |
| 138 | 2 | NT | 2 | NT |
| 139 | 3 | NT | 3 | NT |
| 140 | 1 | NT | 3 | NT |
| 141 | 3 | NT | 1 | NT |
| 142 | 1 | NT | 2 | NT |
| 143 | 1 | NT | 2 | NT |
| 144 | 1 | NT | 1 | NT |
| 145 | 1 | NT | 1 | NT |
| 146 | 1 | NT | 1 | NT |
| 147 | 1 | NT | 1 | NT |
| 148 | 1 | NT | 3 | 1 |
| 149 | 1 | NT | 3 | 1 |
| 150 | 3 | NT | 3 | NT |
| 151 | 3 | NT | 3 | NT |
| 152 | 2 | NT | 3 | NT |
| 153 | 2 | NT | 2 | NT |
| 154 | 1 | NT | 3 | 2 |
| 155 | 3 | NT | 3 | NT |
| 156 | 2 | NT | 2 | NT |
| 157 | 2 | NT | 3 | NT |
| 158 | 3 | NT | 3 | NT |
| 159 | 3 | NT | 3 | NT |
| 160 | 3 | NT | 1 | NT |

-continued

| Compound Number | [C1] HSD1-prot Reduct Score | [C1] HSD2 prot Dehydro Score | [C2] HSD1 cellular 3T3-L1 Score | [C2] HSD2 cellular HepG2 Score |
|---|---|---|---|---|
| 161 | 2 | NT | 1 | NT |
| 162 | 3 | 2 | 3 | 1 |
| 163 | 3 | 2 | 3 | 1 |
| 164 | 1 | NT | 1 | NT |
| 165 | 1 | NT | 1 | NT |
| 166 | NT | NT | 2 | NT |
| 167 | NT | NT | 1 | NT |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D.1: Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A method for treating obesity, diabetes, obesity related cardiovascular diseases, dementia, cognition, osteoporosis and glaucoma, comprising administering an effective amount of a compound having formula

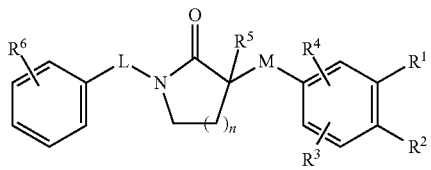

(I)

the N-oxide forms, the pharmaceutically acceptable addition salts and the stereochemically isomeric forms thereof, wherein n is 2;
L represents a $C_{1-3}$alkyl linker optionally substituted with one or two substituents selected from $C_{1-4}$alkyl, $C_{1-3}$alkloxy-$C_{1-4}$alkyl-, hydroxy-$C_{1-4}$alkyl, hydroxy, $C_{1-3}$alkyloxy- or phenyl-$C_{1-4}$alkyl;
M represents a direct bond or a $C_{1-3}$alkyl linker optionally substituted with one or two substituents selected from hydroxy, $C_{1-4}$alkyl or $C_{1-4}$alkyloxy;
$R^1$ and $R^2$ each independently represent hydrogen, halo, cyano, hydroxy,
$C_{1-4}$alkyl optionally substituted with halo,
$C_{1-4}$alkyloxy- optionally substituted with one or where possible two or three substituents selected from hydroxy, $Ar^1$ and halo;
or $R^1$ and $R^2$ taken together with the phenyl ring to which they are attached form naphtyl or 1,3-benzodioxolyl, wherein said naphtyl or 1,3-benzodioxolyl are optionally substituted with halo;
$R^3$ represents hydrogen, halo, $C_{1-4}$alkyl, $C_{1-4}$alkyloxy-, cyano or hydroxy;
$R^4$ represents hydrogen, halo, $C_{1-4}$alkyl, $C_{1-4}$alkyloxy-, cyano or hydroxy;
$R^5$ represents hydrogen, $C_{1-4}$alkyl or $Ar^2$—$C_{1-4}$alky-;
$R^6$ represents hydrogen, halo, $C_{1-4}$alkyl or $C_{1-4}$alkyoxy-;
$Ar^1$ and $Ar^2$ each independently represent phenyl or naphtyl wherein said phenyl and naphtyl are optionally substituted with $C_{1-4}$alkyl, $C_{1-4}$alkyloxy-, or phenyl-$C_{1-4}$alkyl, wherein the effective amount of the compound having formula (I) treats obesity, diabetes, obesity related cardiovascular diseases, dementia, cognition, osteoporosis and glaucoma.

2. The method of claim 1 wherein;
n is 2;
L represents a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl, hydroxy, $C_{1-3}$alkyloxy- or phenyl-$C_{1-4}$alkyl; in particular L represents a $C_1$-linker optionally substituted with $C_{1-4}$alkyl; preferably L represents a $C_1$-linker substituted with $C_{1-4}$alkyl, more preferably a $C_1$-linker substituted with methyl;
M represents a direct bond or a $C_{1-2}$alkyl optionally substituted with one or two substituents selected from hydroxy, $C_{1-4}$alkyl or $C_{1-4}$alkyloxy-; preferably M represents a $C_1$-linker optionally substituted with $C_{1-4}$alkyl;
$R^1$ represents hydrogen, hydroxy, halo, $C_{1-4}$alkyl, $C_{1-4}$alkyloxy-, or $C_{1-4}$alkyloxy substituted with halo;
$R^2$ represents hydrogen, halo, $C_{1-4}$ alkyl, $C_{1-4}$alkyloxy- or $Ar^1$—$C_{1-4}$ alkyloxy-;
$R^3$ represents hydrogen, halo, $C_{1-4}$alkyl, $C_{1-4}$alkyloxy- or cyano;
$R^4$ represents hydrogen, halo, $C_{1-4}$alkyl or $C_{1-4}$alkyloxy-;
$R^5$ represents hydrogen, $C_{1-4}$alkyl or $Ar^2$—$C_{1-4}$alkyl; in particular hydrogen;
$R^6$ represents hydrogen, halo, or $C_{1-4}$alkyloxy; in particular hydrogen, chloro, fluoro, bromo or methoxy;
$Ar^1$ represents phenyl;
$Ar^2$ represents phenyl or naphtyl.

3. The method of claim 1, wherein $R^6$ is at the para position, L represents a $C_2$-alkyl linker and M represents a $C_1$-linker.

4. The method of claim 1, wherein L represents a $C_1$-linker substituted with a $C_{1-4}$alkyl, $C_{1-4}$alkyloxy$C_{1-4}$alkyl-, hydroxy$C_{1-4}$alkyl- or phenyl$C_{1-4}$alkyl- wherein said $C_{1-4}$alkyl, $C_{1-4}$alkyloxy$C_{1-4}$alkyl-, hydroxy$C_{1-4}$alkyl- or phenyl$C_{1-4}$alkyl-is in the S-configuration.

5. The method of claim 1, wherein the administering comprises a pharmaceutical composition comprising a pharmaceutically acceptable carrier and an effective 11β-HSD1 inhibitory amount of the compound having formula (I).

6. The method of claim 5, wherein the pharmaceutical composition is prepared by mixing a pharmaceutically acceptable carrier with an effective 11β-HSD1 inhibitory amount of the compound having formula (I).

* * * * *